US012551692B2

(12) United States Patent
Kaib et al.

(10) Patent No.: US 12,551,692 B2
(45) Date of Patent: Feb. 17, 2026

(54) GARMENTS FOR WEARABLE MEDICAL DEVICES

(71) Applicant: ZOLL Medical Corporation, Chelmsford, MA (US)

(72) Inventors: Thomas E Kaib, Irwin, PA (US); Shane S Volpe, Saltsburg, PA (US); Gregory R Frank, Mt. Lebanon, PA (US); Gary A Freeman, Waltham, MA (US); Mark Jerome Owens, Wexford, PA (US)

(73) Assignee: ZOLL Medical Corporation, Chelmsford, MA (US)

( * ) Notice: Subject to any disclaimer, the term of this patent is extended or adjusted under 35 U.S.C. 154(b) by 0 days.

(21) Appl. No.: 17/215,803

(22) Filed: Mar. 29, 2021

(65) Prior Publication Data

US 2021/0212397 A1 Jul. 15, 2021

Related U.S. Application Data

(63) Continuation of application No. 16/911,920, filed on Jun. 25, 2020, now Pat. No. 12,337,168, which is a (Continued)

(51) Int. Cl.

*A61N 1/04* (2006.01)
*A61N 1/362* (2006.01)

(Continued)

(52) U.S. Cl.

CPC ......... *A61N 1/0484* (2013.01); *A61N 1/0456* (2013.01); *A61N 1/046* (2013.01);

(Continued)

(58) Field of Classification Search

CPC .... A61N 1/0484; A61N 1/0456; A61N 1/046; A61N 1/0476; A61N 1/3625;

(Continued)

(56) References Cited

U.S. PATENT DOCUMENTS 4,094,310 A 6/1978 Mceachern et al.
4,432,368 A 2/1984 Russek (Continued)

FOREIGN PATENT DOCUMENTS

CN 2693794 Y 4/2005
CN 101031334 9/2007

(Continued)

OTHER PUBLICATIONS

International Search Report and Written Opinion for PCT Application No. PCT/US2016/063078, Feb. 8, 2017, 9 pages.

(Continued)

*Primary Examiner* — Catherine M Voorhees
(74) *Attorney, Agent, or Firm* — ZOLL Medical Corporation

(57) ABSTRACT

According to an aspect, an improved modular wearable medical device for monitoring a patient's ECG signals and providing therapeutic shocks in the event of a cardiac arrhythmia is provided. The device includes a garment, a plurality of ECG sensing electrodes that are permanently coupled at first predetermined locations on the garment, at least one pocket or receptacle disposed on the garment and configured to removably secure a module with device electronics within a housing to the garment, a plurality of wires or cables permanently integrated into the garment and operably coupling the plurality of permanently coupled ECG sensing electrodes with the sensor interface module, a plurality of therapy electrodes removably coupled to second predetermined locations on the garment, gel deployment circuitry, one or more capacitors, and a therapy control module configured to control the provision of the therapeutic shocks.

17 Claims, 22 Drawing Sheets

Related U.S. Application Data continuation of application No. 15/357,297, filed on Nov. 21, 2016, now Pat. No. 10,729,910.

(60) Provisional application No. 62/258,666, filed on Nov. 23, 2015.

(51) Int. Cl.

| | |
|---|---|
| ***A61N 1/365*** | (2006.01) |
| ***A61N 1/39*** | (2006.01) |
| *A41D 13/12* | (2006.01) |
| *A41D 31/102* | (2019.01) |
| *A41D 31/12* | (2019.01) |
| *A61B 5/00* | (2006.01) |
| *A61B 5/021* | (2006.01) |
| *A61B 5/0537* | (2021.01) |
| *A61B 5/08* | (2006.01) |
| *A61B 5/11* | (2006.01) |
| *A61B 5/145* | (2006.01) |
| *A61B 7/00* | (2006.01) |

(52) U.S. Cl.

CPC ......... *A61N 1/0476* (2013.01); *A61N 1/3625* (2013.01); *A61N 1/36585* (2013.01); *A61N 1/3925* (2013.01); *A61N 1/3968* (2013.01); *A61N 1/3987* (2013.01); *A41D 13/1281* (2013.01); *A41D 31/102* (2019.02); *A41D 31/12* (2019.02); *A61B 5/021* (2013.01); *A61B 5/0537* (2013.01); *A61B 5/0816* (2013.01); *A61B 5/1118* (2013.01); *A61B 5/14542* (2013.01); *A61B 5/4839* (2013.01); *A61B 5/6804* (2013.01); *A61B 5/6805* (2013.01); *A61B 7/00* (2013.01); *A61B 7/003* (2013.01)

(58) Field of Classification Search

CPC .............. A61N 1/36585; A61N 1/3925; A61N 1/3968; A61N 1/3987; A41D 13/1281; A41D 31/102; A41D 31/12; A41D 31/14; A61B 5/021; A61B 5/0537; A61B 5/0816; A61B 5/1118; A61B 5/14542; A61B 5/4839; A61B 5/6804; A61B 5/6805; A61B 7/00; A61B 7/003; A61B 5/0205

See application file for complete search history.

(56) References Cited

U.S. PATENT DOCUMENTS

| | | | | |
|---|---|---|---|---|
| 4,632,122 | A | 12/1986 | Johansson et al. | |
| 4,698,848 | A | 10/1987 | Buckley | |
| 4,928,690 | A | 5/1990 | Heilman et al. | |
| 4,978,926 | A | 12/1990 | Zerod et al. | |
| 5,062,834 | A | 11/1991 | Gross et al. | |
| 5,078,134 | A * | 1/1992 | Heilman | A61N 1/046 607/142 |
| 5,176,380 | A | 1/1993 | Evans et al. | |
| 5,330,505 | A | 7/1994 | Cohen | |
| 5,348,008 | A | 9/1994 | Bornn et al. | |
| 5,353,793 | A | 10/1994 | Bornn | |
| 5,357,696 | A | 10/1994 | Gray et al. | |
| 5,365,932 | A | 11/1994 | Greenhut | |
| 5,564,429 | A | 10/1996 | Bornn et al. | |
| 5,662,689 | A | 9/1997 | Elsberry et al. | |
| 5,718,242 | A | 2/1998 | McClure et al. | |
| 5,738,102 | A | 4/1998 | Lemelson | |
| 5,741,306 | A | 4/1998 | Glegyak et al. | |
| 5,758,443 | A | 6/1998 | Pedrazzini | |
| 5,792,190 | A | 8/1998 | Olson et al. | |
| 5,929,601 | A | 7/1999 | Kaib et al. | |
| 5,944,669 | A | 8/1999 | Kaib | |
| 6,016,445 | A | 1/2000 | Baura | |
| 6,045,503 | A | 4/2000 | Grabner et al. | |
| 6,065,154 | A | 5/2000 | Hulings et al. | |
| 6,097,982 | A | 8/2000 | Glegyak et al. | |
| 6,097,987 | A | 8/2000 | Milani | |
| 6,148,233 | A * | 11/2000 | Owen | A61N 1/0476 607/5 |
| 6,169,387 | B1 | 1/2001 | Kaib | |
| 6,169,397 | B1 | 1/2001 | Steinbach et al. | |
| 6,253,099 | B1 | 6/2001 | Oskin et al. | |
| 6,280,461 | B1 | 8/2001 | Glegyak et al. | |
| 6,280,471 | B1 | 8/2001 | Peyman et al. | |
| 6,390,996 | B1 | 5/2002 | Halperin et al. | |
| 6,406,426 | B1 | 6/2002 | Reuss et al. | |
| 6,666,830 | B1 | 12/2003 | Lehrman et al. | |
| 6,681,003 | B2 | 1/2004 | Linder et al. | |
| 6,690,969 | B2 | 2/2004 | Bystrom et al. | |
| 6,790,178 | B1 | 9/2004 | Mault et al. | |
| 6,804,554 | B2 | 10/2004 | Ujhelyi et al. | |
| 6,827,695 | B2 | 12/2004 | Palazzolo et al. | |
| 6,865,413 | B2 | 3/2005 | Halperin et al. | |
| 6,908,437 | B2 | 6/2005 | Bardy | |
| 6,990,373 | B2 | 1/2006 | Jayne et al. | |
| 7,074,199 | B2 | 7/2006 | Halperin et al. | |
| 7,108,665 | B2 | 9/2006 | Halperin et al. | |
| 7,118,542 | B2 | 10/2006 | Palazzolo et al. | |
| 7,122,014 | B2 | 10/2006 | Palazzolo et al. | |
| 7,149,579 | B1 | 12/2006 | Koh et al. | |
| 7,177,684 | B1 | 2/2007 | Kroll et al. | |
| 7,220,235 | B2 | 5/2007 | Geheb et al. | |
| 7,277,752 | B2 | 10/2007 | Matos | |
| 7,295,871 | B2 | 11/2007 | Halperin et al. | |
| 7,340,296 | B2 | 3/2008 | Stahmann et al. | |
| 7,427,921 | B2 | 9/2008 | Van Woudenberg | |
| 7,453,354 | B2 | 11/2008 | Reiter et al. | |
| 7,476,206 | B2 | 1/2009 | Palazzolo et al. | |
| 7,488,293 | B2 | 2/2009 | Marcovecchio et al. | |
| 7,702,390 | B1 | 4/2010 | Min | |
| 7,810,172 | B2 | 10/2010 | Williams | |
| 7,831,303 | B2 | 11/2010 | Rueter et al. | |
| 7,974,689 | B2 | 7/2011 | Volpe et al. | |
| 8,121,683 | B2 | 2/2012 | Bucher et al. | |
| 8,140,154 | B2 | 3/2012 | Donnelly et al. | |
| 8,271,082 | B2 | 9/2012 | Donnelly et al. | |
| 8,308,489 | B2 | 11/2012 | Lee et al. | |
| 8,369,944 | B2 | 2/2013 | Macho et al. | |
| 8,600,486 | B2 | 12/2013 | Kaib et al. | |
| 8,649,861 | B2 | 2/2014 | Donnelly et al. | |
| 8,706,215 | B2 | 4/2014 | Kaib et al. | |
| 8,904,214 | B2 | 12/2014 | Volpe et al. | |
| 8,909,335 | B2 | 12/2014 | Radzelovage | |
| 9,008,801 | B2 | 4/2015 | Kaib et al. | |
| 9,135,398 | B2 | 9/2015 | Kaib et al. | |
| 9,398,859 | B2 | 7/2016 | Volpe et al. | |
| 10,729,910 | B2 * | 8/2020 | Kaib | A61N 1/0476 |
| 10,828,007 | B1 | 11/2020 | Telfort et al. | |
| 2002/0107435 | A1 | 8/2002 | Swetlik et al. | |
| 2003/0004547 | A1 | 1/2003 | Owen et al. | |
| 2003/0023277 | A1 | 1/2003 | Owen et al. | |
| 2003/0032988 | A1 | 2/2003 | Fincke | |
| 2003/0095648 | A1 | 5/2003 | Kaib et al. | |
| 2003/0149462 | A1 | 8/2003 | White et al. | |
| 2003/0158593 | A1 | 8/2003 | Heilman et al. | |
| 2003/0174049 | A1 | 9/2003 | Beigel et al. | |
| 2003/0195567 | A1 | 10/2003 | Jayne et al. | |
| 2003/0212311 | A1 | 11/2003 | Nova et al. | |
| 2003/0233129 | A1 | 12/2003 | Matos | |
| 2004/0007970 | A1 | 1/2004 | Ma et al. | |
| 2004/0049233 | A1 | 3/2004 | Edwards | |
| 2004/0143297 | A1 | 7/2004 | Ramsey, III | |
| 2005/0049515 | A1 | 3/2005 | Misczynski et al. | |
| 2005/0054941 | A1 | 3/2005 | Ting et al. | |
| 2005/0131465 | A1 | 6/2005 | Freeman et al. | |
| 2006/0036292 | A1 | 2/2006 | Smith et al. | |
| 2006/0085049 | A1 | 4/2006 | Cory et al. | |
| 2006/0129067 | A1 | 6/2006 | Grajales et al. | |
| 2006/0178706 | A1 | 8/2006 | Lisogurski et al. | |
| 2006/0220809 | A1 | 10/2006 | Stigall et al. | |
| 2006/0264776 | A1 | 11/2006 | Stahmann et al. | |
| 2006/0270952 | A1 | 11/2006 | Freeman et al. | |

(56) References Cited

U.S. PATENT DOCUMENTS

2007/0073120 A1 3/2007 Li et al.
2007/0089800 A1 4/2007 Sharma
2007/0118056 A1 5/2007 Wang et al.
2007/0129769 A1* 6/2007 Bourget ............... A61B 5/4815 607/45
2007/0161913 A1 7/2007 Farrell et al.
2007/0166503 A1 7/2007 Hannigan
2007/0169364 A1 7/2007 Townsend et al.
2007/0239220 A1 10/2007 Greenhut et al.
2007/0265671 A1 11/2007 Roberts et al.
2007/0299474 A1 12/2007 Brink
2008/0004536 A1 1/2008 Baxi et al.
2008/0015454 A1 1/2008 Gal
2008/0030656 A1 2/2008 Watson et al.
2008/0031270 A1 2/2008 Tran et al.
2008/0033495 A1 2/2008 Kumar
2008/0045815 A1 2/2008 Derchak et al.
2008/0046015 A1 2/2008 Freeman et al.
2008/0058884 A1 3/2008 Matos
2008/0221631 A1 9/2008 Dupelle
2008/0249591 A1 10/2008 Gaw et al.
2008/0287770 A1* 11/2008 Kurzweil ................. A61B 5/01 600/388
2008/0306562 A1 12/2008 Donnelly et al.
2008/0312520 A1 12/2008 Rowlandson et al.
2008/0312709 A1 12/2008 Volpe et al.
2009/0073991 A1 3/2009 Landrum et al.
2009/0076336 A1 3/2009 Mazar et al.
2009/0076340 A1 3/2009 Libbus et al.
2009/0076341 A1 3/2009 James et al.
2009/0076342 A1 3/2009 Amurthur et al.
2009/0076343 A1 3/2009 James et al.
2009/0076344 A1 3/2009 Libbus et al.
2009/0076345 A1 3/2009 Manicka et al.
2009/0076346 A1 3/2009 James et al.
2009/0076348 A1 3/2009 Manicka et al.
2009/0076349 A1 3/2009 Libbus et al.
2009/0076350 A1 3/2009 Bly et al.
2009/0076363 A1 3/2009 Bly et al.
2009/0076364 A1 3/2009 Libbus et al.
2009/0076397 A1 3/2009 Libbus et al.
2009/0076405 A1 3/2009 Amurthur et al.
2009/0076410 A1 3/2009 Libbus et al.
2009/0076559 A1 3/2009 Libbus et al.
2009/0082691 A1 3/2009 Denison et al.
2009/0093687 A1 4/2009 Telfort et al.
2009/0138059 A1 5/2009 Ouwerkerk
2009/0177100 A1 7/2009 Ternes
2009/0234410 A1 9/2009 Libbus et al.
2009/0264792 A1 10/2009 Mazar
2009/0275848 A1 11/2009 Brockway et al.
2009/0287120 A1 11/2009 Ferren et al.
2009/0292194 A1 11/2009 Libbus et al.
2009/0306730 A1 12/2009 Roso
2010/0041975 A1 2/2010 Chen et al.
2010/0056881 A1 3/2010 Libbus et al.
2010/0069735 A1 3/2010 Berkner
2010/0076513 A1 3/2010 Warren et al.
2010/0076533 A1 3/2010 Dar et al.
2010/0083968 A1 4/2010 Wondka et al.
2010/0179438 A1 7/2010 Heneghan et al.
2010/0234715 A1 9/2010 Shin et al.
2010/0234716 A1 9/2010 Engel
2010/0295674 A1 11/2010 Hsieh et al.
2010/0298899 A1 11/2010 Donnelly et al.
2010/0312297 A1 12/2010 Volpe et al.
2011/0077728 A1 3/2011 Li et al.
2011/0196220 A1 8/2011 Storm
2011/0202101 A1 8/2011 Tan et al.
2011/0288604 A1* 11/2011 Kaib .................... A61N 1/3987 607/149
2011/0288605 A1 11/2011 Kaib et al.
2012/0011382 A1 1/2012 Volpe et al.
2012/0112903 A1 5/2012 Kaib et al.
2012/0144551 A1 6/2012 Guldalian
2012/0146797 A1* 6/2012 Oskin .................. A61N 1/0484 340/573.1
2012/0158074 A1 6/2012 Hall
2012/0158075 A1* 6/2012 Kaib ...................... A61N 1/046 607/7
2013/0237861 A1 9/2013 Margarida et al.
2013/0325078 A1 12/2013 Whiting et al.
2013/0325096 A1 12/2013 Dupelle et al.
2014/0046393 A1 2/2014 Sullivan
2014/0163334 A1 6/2014 Volpe et al.
2014/0200426 A1* 7/2014 Taub .................. A61B 5/14532 600/347
2014/0207201 A1 7/2014 Piha et al.
2014/0249613 A1 9/2014 Kaib
2014/0371806 A1* 12/2014 Raymond .............. A61N 1/046 607/5
2015/0005588 A1 1/2015 Herken
2015/0039053 A1 2/2015 Kaib et al.
2015/0040282 A1* 2/2015 Longinotti-Buitoni ...................... A61B 5/742 2/69
2015/0067943 A1 3/2015 Scheffler et al.
2015/0196076 A1* 7/2015 Billingslea ........... A41D 27/205 2/114
2015/0217121 A1* 8/2015 Subramanian ......... A61N 1/046 607/7
2015/0231403 A1 8/2015 Kaib et al.
2015/0320994 A1 11/2015 Buchanan et al.
2016/0143585 A1 5/2016 Donnelly et al.
2018/0271380 A1* 9/2018 Gregg .................. A61B 5/7278
2020/0390172 A1* 12/2020 Kaib .................... A61N 1/0484

FOREIGN PATENT DOCUMENTS

| | | |
|---|---|---|
| CN | 101657229 | 2/2010 |
| CN | 101848677 | 9/2010 |
| CN | 201734710 U | 2/2011 |
| CN | 102975402 | 3/2013 |
| CN | 103002800 | 3/2013 |
| CN | 103315722 A | 9/2013 |
| CN | 103347440 | 10/2013 |
| CN | 103405851 | 11/2013 |
| DE | 2644236 | 4/1978 |
| EP | 0295497 | 9/1993 |
| EP | 0335356 | 3/1996 |
| EP | 0948972 | 10/1999 |
| EP | 1642616 | 4/2006 |
| EP | 1455640 | 1/2008 |
| EP | 1720446 | 7/2010 |
| EP | 2433561 | 3/2012 |
| JP | S6368135 | 3/1988 |
| JP | 5115450 | 5/1993 |
| JP | H07541 | 1/1995 |
| JP | H1028679 | 2/1998 |
| JP | H11319119 | 11/1999 |
| JP | 2002102361 | 4/2002 |
| JP | 2002514107 | 5/2002 |
| JP | 2002200059 | 7/2002 |
| JP | 2002534231 | 10/2002 |
| JP | 2003235997 | 8/2003 |
| JP | 2004538066 | 12/2004 |
| JP | 2005275606 | 10/2005 |
| JP | 2007531592 | 11/2007 |
| JP | 2008302228 | 12/2008 |
| JP | 2009510276 | 3/2009 |
| JP | 2009518057 | 5/2009 |
| JP | 2009528909 | 8/2009 |
| JP | 2010508128 | 3/2010 |
| JP | 2010530114 | 9/2010 |
| WO | 200002484 | 1/2000 |
| WO | 2004054656 | 7/2004 |
| WO | 2004067083 | 8/2004 |
| WO | 2005082454 | 9/2005 |
| WO | 2006050235 | 5/2006 |
| WO | 2007019325 | 2/2007 |
| WO | 2007057169 | 5/2007 |
| WO | 2007077997 | 7/2007 |
| WO | 2008137286 | 11/2008 |

(56) References Cited

FOREIGN PATENT DOCUMENTS

| | | | |
|---|---|---|---|
| WO | 2009034506 | | 3/2009 |
| WO | 2009153730 | | 12/2009 |
| WO | 2010014497 | | 2/2010 |
| WO | 2010025432 | | 3/2010 |
| WO | 2011146448 | | 11/2011 |
| WO | 2013033238 | A1 | 3/2013 |
| WO | 2015127466 | | 8/2015 |
| WO | 2017091502 | | 6/2017 |

OTHER PUBLICATIONS

Extended European Search Report for Appl. No. 20166728.4, dated Jun. 2020, 9 pages.

American Journcal of Respiratory and Critical Care Medicine, vol. 166, pp. 111-117 (2002), American Thoracic Society, ATS Statement: Guidelines for the Six-Minute Walk Test, available at http://www.atsjournals.org/doi/pdf/10.1164/ajrccm.166.1.at1102.

De Bock et al., "Captopril treatment of chronic heart failure in the very old", J. Gerontol. (1994) 49: M148-M152.

Harnett, P.R. et al., "A Survey and Comparison of Laboratory Test Methods for Measuring Wicking", Textile Research Journal, Jul. 1984.

O'Keefe et al., "Reproducibility and responsiveness of quality of life assessment and six minute walk test in elderly heart failure patients," Heart (1998) 80:377-382.

Chinese Office Action and Search Report for Chinese Application No. 201680060591.9 dated Sep. 21, 2020, 8 pages.

European Extended Search Report for European application No. 24201750.7, mailed on Dec. 19, 2024, 9 pages.

Wikipedia, "Wearable Cardioverter Defibrillator", version of Feb. 3, 2014, retrieved from URL: <https://en.wikipedia/org/w/index.php?title=Wearable_cardioverter_defibrillator&oldid=594230885>; retrieved on Mar. 29, 2024, 3 pages.

Wadsworth, Larry C. et al., "New Level 4 Cotton-Comfortable Medical Barrier Fabrics Made With Cotton, Spunbond and Breathable Coatings", INDA & AATCC, Sep. 19, 2005, 62 pages.

Ramkumar, Seshadri et al., "Relationship Between Cotton Varieties and Moisture Vapor Transport of Knitted Fabrics", Journal of Engineered Fibers and Fabrics, vol. 2, Issue 4, 2007, 9 pages.

Das, A. et al., "Study on Moisture Vapor Transmission Characteristics of Woven Fabrics From Cotton-Acrylic Bulked Yarns", Journal of the Textile Institute, vol. 104, No. 3, 2013, pp. 322-329.

Y.J. Ren et al., "Water Vapour Transfer in Wet Waterproof Breathable Fabrics", Journal of Industrial Textiles, vol. 32, No. 3, Jan. 2003, pp. 165-175.

Kar Fung Yi, "Effect of Heat and Moisture Transfer Properties of T-Shirts on Comfort Sensations", Master Thesis, Hong Kong Polytechnic University, 2006, 311 pages.

Wikipedia, "Defibrillation", version of Nov. 12, 2015, retrieved from URL: <https://en.wikipedia.org/w/index.php?title=Defibrillation&oldid=690325051>, retrieved on May 31, 2023, 12 pages.

Wikipedia, "Moisture Vapor Transmission Rate", version of Jul. 23, 2015, retrieved from URL: <https://en.wikipedia.org/w/index.php?title=Moisture_vapor_transmission_rate&oldid=672692352>, retrieved on May 31, 2023, 3 pages.

Lubnin, A. et al., "Novel, 'Breathable' Polyurethane Dispersions", PCI Magazine, Jan. 1, 2005, 19 pages.

Macleay, Alicia, "Mountain Hardwear's Dry. Q Enters Waterproof-Breathable Battle", Trailspace Blog, Feb. 8, 2011, retrieved from URL: <https://web.archive.org/web/20110210025249/http://www.trailspace.com:80/articles/2011/02/08/mountain-hardwear-dry-q.html>, retrieved on Jun. 29, 2023, 5 pages.

ZOLL Lifecor Corporation, LifeVest System Model WCD 3100 Operator's Manual, Copyright 2006, 48 pages.

U.S. Food and Drug Administration, P010030 Lifecor, Inc. WCD 2000 System—Summary of Safety and Effectiveness Data, decision date: Dec. 18, 2001, 17 pages.

D.P. Zipes et al., "Cardiac Electrophysiology—From Cell to Bedside", second edition, Chapter 118 titled "External Direct Current Cardioversion-Defibrillation", 1995, 10 pages.

Bronzino, Joseph D., "The Biomedical Engineering Handbook", Chapter 81 titled "External Defibrillators", 1995, 11 pages.

D.P. Zipes et al., "Cardiac Electrophysiology—From Cell to Bedside", second edition, Chapter 91 titled "Ambulatory (Holter) Electrocardiogramacordings", 1995, 9 pages.

"Tegaderm High Performance Foam Adhesive Dressing", 3M Health Care, 2010, 8 pages.

* cited by examiner

GARMENTS FOR WEARABLE MEDICAL DEVICES

CROSS-REFERENCE TO RELATED APPLICATION

This application claims priority under 35 U.S.C. § 120 as a continuation of U.S. application Ser. No. 16/911,920 titled "GARMENTS FOR WEARABLE MEDICAL DEVICES," filed Jun. 25, 2020, which claims priority under 35 U.S.C. § 120 as a continuation of U.S. application Ser. No. 15/357,297 titled "GARMENTS FOR WEARABLE MEDICAL DEVICES," filed Nov. 21, 2016, now U.S. Pat. No. 10,729,910, which claims priority under 35 U.S.C. § 119(e) to U.S. Provisional Application Ser. No. 62/258,666 titled "GARMENTS FOR WEARABLE MEDICAL DEVICES," filed Nov. 23, 2015, each of which is hereby incorporated herein by reference in its entirety for all purposes.

BACKGROUND

Technical Field

This disclosure relates to garments for wearable medical devices including, for example, wearable monitoring devices and/or wearable treatment devices.

Discussion

There are a wide variety of electronic and mechanical devices for monitoring and treating patients' medical conditions. In some examples, depending on the underlying medical condition being monitored or treated, medical devices such as cardiac pacemakers or defibrillators may be surgically implanted or connected externally to the patient. In some cases, physicians may use medical devices alone or in combination with drug therapies to treat patient medical conditions.

One of the most deadly cardiac arrhythmias is ventricular fibrillation, which occurs when normal, regular electrical impulses are replaced by irregular and rapid impulses, causing the heart muscle to stop normal contractions and to begin to quiver. Normal blood flow ceases, and organ damage or death can result in minutes if normal heart contractions are not restored. Because the victim has no perceptible warning of the impending fibrillation, death often occurs before the necessary medical assistance can arrive. Other cardiac arrhythmias can include excessively slow heart rates known as bradycardia.

Implantable or external pacemakers and defibrillators (such as automated external defibrillators or AEDs) have significantly improved the ability to treat these otherwise life-threatening conditions. Such devices operate by applying corrective electrical pulses directly to the patient's heart. For example, bradycardia can be corrected through the use of an implanted or external pacemaker device. Ventricular fibrillation can be treated by an implanted or external defibrillator.

External pacemakers, defibrillators and other medical monitors designed for ambulatory and/or long-term use have further improved the ability to timely detect and treat life-threatening conditions. For example, certain medical devices operate by continuously or substantially continuously monitoring the patient's heart through one or more sensing electrodes for treatable arrhythmias and, when such is detected, the device applies corrective electrical pulses directly to the heart through one or more therapy electrodes.

SUMMARY

According to at least one aspect, a wearable cardiac device is provided. The wearable cardiac device includes a garment worn about a torso of a patient, the garment having at least an anterior portion and a posterior portion, at least one sensing electrode configured to monitor a cardiac activity of the patient, at least one therapy electrode configured to provide a treatment to the patient, and a controller. The controller may be configured to detect a cardiac condition of the patient based on the monitored cardiac activity of the patient and provide a treatment to the patient based on the detected cardiac condition, the controller comprising a plurality of modules configured to be integrated into and distributed about the garment. It is appreciated that at least one of the at least one sensing electrode and the at least one therapy electrode may be configured to be integrated into the garment.

In some examples, the garment includes at least one of: a vest worn about an upper body of the patient, a wrap-around garment, and shoulder straps. In some examples, the garment includes a one-shoulder garment configured to be worn about one shoulder and wrap around an upper torso of the patient.

In some examples, the garment is configured to be machine washable. In some examples, the garment is configured to be water resistant. In some examples, the garment includes a low-skin irritation material.

In some examples, the plurality of modules are distributed by weight about the garment for an even weight distribution. In some examples, one or more of the plurality of modules is permanently secured into the garment. In some examples, one or more of the plurality of modules is configured to be removably secured into the garment. In some examples, one or more of the plurality of modules is configured to be secured within corresponding one or more pockets provided in the garment. In some examples, one or more of the plurality of modules is configured to be movably secured to the garment. In some examples, one or more of the plurality of modules is configured to be slidably secured to the garment.

In some examples, the wearable cardiac device further includes one or more sensors configured to monitor one or more of patient activity, patient motion, heart sounds, lung sounds, tissue fluids, lung fluid, blood oxygen levels, blood pressure. In some examples, the wearable cardiac device further includes one or more components for delivering a drug therapy to the patient.

In some examples, at least two of the plurality of modules are electrically coupled by conductive thread integrated into the garment. In some examples, at least two of the plurality of modules are operably coupled by optical fiber integrated into the garment.

In some examples, the plurality of modules comprises at least one low-voltage module and at least one high-voltage module. In some examples, the at least one low-voltage module comprises circuitry for controlling at least one of user interactions, cardiac signal acquisition and monitoring, cardiac arrhythmia detection, synchronization of defibrillation pulses with cardiac signals, treatment sequence, patient alerts, data communications, and data storage. In some examples, the at least one high-voltage module comprises at least one of a therapy control module and an energy storage module.

In some examples, the plurality of modules comprises an operations module to monitor cardiac data received from the at least one electrode and direct administration of treatment to the patient. In some examples, the plurality of modules comprises a communications module configured to communicate with at least one external system.

In some examples, the plurality of modules comprises an energy storage module to store energy for at least one therapeutic pulse. In some examples, the energy storage module comprises a plurality of capacitors and at least one non-rechargeable battery to provide power to the plurality of capacitors. In some examples, the energy storage module is coupled to a therapy control module to control at least a discharge of energy from the energy storage module.

In some examples, the plurality of modules includes a first energy storage module to store energy for a first portion of a therapeutic pulse and a second energy storage module, distinct from the first energy storage module, to store energy for a second portion of the therapeutic pulse. In some examples, the plurality of modules includes a first energy storage module integrated into a front portion of the garment and a second energy storage module integrated into a rear portion of the garment. In some examples, the plurality of modules includes a plurality of capacitors distributed about and integrated into the garment.

In some examples, at least one of the plurality of modules removably couples to a rechargeable battery. In some examples, the garment removably couples to a rechargeable battery.

In some examples, the wearable cardiac device includes at least one therapy electrode integrated into the garment. In some examples, the wearable cardiac device includes at least one user interface module integrated into the garment. In some examples, the wearable cardiac device includes at least one user interface module communicatively coupled to at least one of the plurality of modules.

According to at least one aspect, a wearable cardiac monitoring device is provided. The wearable cardiac monitoring device includes a garment worn about a torso of a patient, the garment being configured to removably couple to at least one treatment module, at least one sensing electrode configured to be integrated into the garment and monitor a cardiac activity of the patient, and a plurality of cardiac monitoring modules distributed about and integrated into the garment for an ergonomic fit on the patient.

In some examples, at least two of the plurality of monitoring modules are electrically coupled by conductive thread integrated into the garment. In some examples, at least two of the plurality of monitoring modules are operably coupled by optical fiber integrated into the garment.

In some examples, the garment includes at least one of: hook-and-loop fasteners, magnets, and snaps to removably couple the at least one treatment module to the garment. In some examples, the garment is configured to electrically couple to the at least one treatment module using at least one of conductive thread, conductive snaps, and conductive contacts. In some examples, the garment is configured to operatively couple to the at least one treatment module using at least one of a capacitive coupling, an IR coupling, and an inductive coupling.

In some examples, the plurality of monitoring modules comprises at least one low-voltage module and the at least one treatment module comprises at least one high-voltage module.

In some examples, at least one treatment module comprises an energy storage module to store energy for at least one therapeutic pulse. In some examples, the energy storage module comprises a plurality of capacitors and at least one non-rechargeable battery to provide power to the plurality of capacitors. In some examples, at least one treatment module comprises a therapy control module coupled to the energy storage module to control at least a discharge of energy from the energy storage module.

According to at least one aspect, a wearable cardiac device is provided. The wearable cardiac device includes a garment worn about a torso of a patient, at least one sensing electrode configured to monitor cardiac activity of the patient, at least one therapy electrode configured to provide treatment to the patient, and a controller. The controller may be configured to detect a cardiac condition of the patient based on the monitored cardiac activity of the patient and provide at least one therapeutic pulse to the patient based on the detected cardiac condition. The controller may include a plurality of separate and distinct modules distributed about the garment. The plurality of separate and distinct modules may include at least one high-voltage module and at least one low-voltage module. The high-voltage module includes one or more high-voltage components operating at one or more high-voltage levels and the low-voltage module includes one or more low-voltage components operating at below the one or more high-voltage levels. It is appreciated that conductive thread may be integrated into the garment to electrically couple at least two of the plurality of modules.

In some examples, at least one low-voltage module comprises circuitry for controlling at least one of user interactions, cardiac signal acquisition and monitoring, cardiac arrhythmia detection, synchronization of defibrillation pulses with cardiac signals, treatment sequence, patient alerts, data communications, and data storage. In some examples, the one or more high voltage levels comprises at least one of 100 volts, 1000 volts, and 1,500 volts.

In some examples, at least one low-voltage module comprises an operations module to monitor cardiac data received from the at least one electrode and direct administration of treatment to the patient. In some examples, at least one low-voltage module comprises a communications module configured to communicate with at least one external system. In some examples, at least one high voltage module includes at least one energy storage device to store energy for the at least one therapeutic pulse. In some examples, at least one high voltage module includes at least one power control device to control one or more characteristics of the at least one therapeutic pulse.

In some examples, one or more modules of the plurality of modules is permanently coupled to the garment. In some examples, one or more modules of the plurality of modules is configured to be removably secured into the garment. In some examples, one or more modules of the plurality of modules is configured to be secured within corresponding one or more pockets provided in the garment. In some examples, at least one of the at least one sensing electrode and the at least one therapy electrode are integrated into the garment.

According to at least one aspect, a wearable cardiac device is provided. The wearable cardiac device includes a garment worn about a torso of a patient, at least one sensing electrode configured to monitor cardiac activity of the patient, at least one therapy electrode configured to provide treatment to the patient, and a controller. The controller includes a plurality of separate and distinct modules distributed about the garment, the plurality of separate and distinct modules includes at least one monitoring module integrated into the garment to detect a cardiac condition of the patient based on the monitored cardiac activity of the patient and at least one treatment module removably secured to the garment to provide treatment to the patient based on the detected cardiac condition.

In some examples, at least two modules of the plurality of modules are electrically coupled by conductive thread integrated into the garment. In some examples, the garment comprises at least one of hook-and-loop fasteners, magnets, and snaps to removably couple the at least one treatment module to the garment. In some examples, the garment is configured to electrically couple to the at least one treatment module using at least one of: conductive thread, conductive snaps, and conductive contacts. In some examples, the garment is configured to operatively couple to the at least one treatment module using at least one of a capacitive coupling, an IR coupling, and an inductive coupling. In some examples, at least one of the at least one sensing electrode and the at least one therapy electrode are integrated into the garment.

In some examples, the at least one treatment module comprises an energy storage module to store energy for at least one therapeutic pulse. In some examples, the energy storage module comprises a plurality of capacitors and at least one non-rechargeable battery to provide power to the plurality of capacitors. In some examples, at least one treatment module further comprises a therapy control module coupled to the energy storage module to control one or more characteristics of the at least one therapeutic pulse.

According to at least one aspect, a wearable cardiac device is provided. The cardiac device includes a garment worn about a torso of a patient, at least one sensing electrode configured to monitor cardiac activity of the patient, at least one therapy electrode configured to provide treatment to the patient, a controller comprising a plurality of separate and distinct modules distributed about the garment. The plurality of modules includes an operations module coupled to the at least one sensing electrode and configured to detect at least one cardiac condition of the patient, an energy storage module coupled to the at least one therapy electrode and configured to store energy for at least one therapeutic shock to be applied to the patient, and a communications module coupled to the operations module to communicate with at least one external device.

In some examples, the plurality of modules further comprises a sensor interface module coupled between the operations module and the at least one sensing electrode, the sensor interface module being configured to receive cardiac data from the at least one sensing electrode, digitize the cardiac data, and communicate the digitized cardiac data to the operations module. In some examples, the plurality of modules further comprises a therapy control module coupled between the energy storage module and the operations module, the therapy control module being configured to control at least one characteristic of the at least one therapeutic shock to be applied to the patient.

In some examples, the plurality of modules is operatively coupled by at least one of conductive thread integrated into the garment, conductive cables, and optical fiber cables. In some examples, one or more modules of the plurality of modules is permanently coupled into the garment. In some examples, one or more modules of the plurality of modules is configured to be removably secured into the garment. In some examples, one or more modules of the plurality of modules is configured to be secured within corresponding one or more pockets provided in the garment.

According to at least one aspect, a wearable cardiac device is provided. The wearable cardiac device includes a garment worn about a torso of a patient, at least one sensing electrode configured to monitor cardiac activity of the patient, at least one therapy electrode configured to provide treatment to the patient, and a controller. The controller may be configured to detect a cardiac condition of the patient based on the monitored cardiac activity of the patient and provide at least one therapeutic pulse to the patient based on the detected cardiac condition, the controller comprising a plurality of separate and distinct capacitor modules integrated into the garment and coupled to the at least one therapy electrode and at least one charger circuit to charge the plurality of capacitors.

In some examples, each of the capacitor modules comprises one or more capacitors encapsulated by an enclosure that is integrated into the garment. In some examples, each of the capacitor modules comprises one or more capacitors integrated into the garment.

In some examples, the plurality of capacitor modules are organized into a plurality of parallel capacitor banks. In some examples, the plurality of parallel capacitor banks are charged by the at least one charger in parallel and are discharged to the at least one therapy electrode in series. In some examples, at least two of the plurality of parallel capacitor banks are coupled by at least one switch that is integrated into the garment.

According to at least one aspect, a wearable cardiac device is provided. The wearable cardiac device includes a garment worn about a torso of a patient, the garment having at least an anterior portion and a posterior portion, at least one sensing electrode configured to monitor a cardiac activity of the patient, at least one therapy electrode configured to deliver a therapeutic shock to the patient based on the monitored cardiac activity, a gel deployment pack removably coupled to the garment and the at least one therapy electrode, the gel deployment pack configured to release conductive gel on the patient's skin substantially proximate to the therapy electrode, and a plurality of modules permanently disposed into and distributed about the garment. The plurality of modules may be configured to detect a cardiac condition of the patient based on the monitored cardiac activity of the patient and cause the release of the conductive gel and the delivery of the therapeutic shock to the patient based on the detected cardiac condition.

According to at least one aspect, there is provided a wearable cardiac monitoring device. The device comprises a garment configured to be worn about a torso of a patient and patient monitoring circuitry disposed in the garment and configured to monitor one or more physiological signals from the patient. The patient monitoring circuitry comprises a plurality of separate and distinct modules communicatively coupled to one another via one or more communication links. The patient monitoring circuitry is configured to monitor at least a cardiac activity of the patient, detect the presence of a cardiac arrhythmia in the patient, and provide one or more notifications regarding the cardiac arrhythmia. The plurality of the separate and distinct modules are integrated into and distributed about the garment for an ergonomic fit on the patient. The device further includes high-voltage circuitry comprising therapy control circuitry and energy storage devices. The high-voltage circuitry is disposed within a treatment module that is configured to be separable from the wearable cardiac monitoring device.

In some examples, the patient monitoring circuitry comprises ECG sensor circuitry configured to sense and process electrocardiogram (ECG) signals of the patient, acoustic sensor circuitry configured to detect and process heart and/or lung sounds of the patient, respiration sensor circuitry configured to sense and process respiration of the patient, and radio-frequency circuitry configured to detect and process fluid levels of the patient. The ECG sensor circuitry, the acoustic sensor circuitry, the respiration sensor circuitry, and the radio-frequency circuitry may be disposed within the separate and distinct modules.

In some examples, the therapy control circuitry is configured to initiate a treatment to the patient based on the one or more notifications regarding the cardiac arrhythmia.

In some examples, the therapy control circuitry is configured to initiate a treatment to the patient, the treatment comprising at least one of a pacing therapy, a defibrillation therapy, and a transcutaneous electrical nerve stimulation (TENS) therapy.

In some examples, the garment comprises at least one of a vest worn about an upper body of the patient, a wrap-around garment, and a one-shoulder garment configured to be worn about one shoulder and wrap around an upper torso of the patient.

In some examples, the garment is configured to be machine washable, water resistant, and permeable to transmission of moisture and water vapor from an inner layer towards an outer layer of the garment, and comprises a low-skin irritation material.

In some examples, the garment is configured to have an average moisture transmission rate of between 100 $g/m^2/day$ to 250 $g/m^2/day$.

In some examples, the garment is configured to have an average moisture transmission rate of between 250 $g/m^2/day$ to 20,000 $g/m^2/day$.

In some examples, the garment is configured to have an average moisture transmission rate of between 20,000 $g/m^2/day$ to 50,000 $g/m^2/day$.

In some examples, the garment is configured to be air permeable to promote ventilation through the garment.

In some examples, the plurality of the separate and distinct modules are distributed by weight about the garment for an even weight distribution.

In some examples, one or more of the plurality of separate and distinct modules is permanently secured into the garment.

In some examples, one or more of the plurality of separate and distinct modules is configured to be removably secured into the garment.

In some examples, one or more of the plurality of separate and distinct modules is configured to be movably secured to the garment.

In some examples, one or more of the plurality of separate and distinct modules is configured to be slidably secured to the garment.

In some examples, the device further comprises one or more sensors configured to monitor one or more of patient activity, patient motion, heart sounds, lung sounds, tissue fluids, lung fluid, blood oxygen levels, and blood pressure.

In some examples, the device further comprises one or more components for delivering a drug therapy to the patient.

In some examples, at least two of the plurality of modules is electrically coupled by conductive thread integrated into the garment.

According to at least one aspect, there is provided a wearable cardiac monitoring device. The device comprises a garment configured to be worn about a torso of a patient, a plurality of cardiac sensing electrodes supported by the garment and configured to monitor a cardiac activity of the patient, at least one therapy electrode supported by the garment and configured to provide treatment to the patient, cardiac monitoring circuitry disposed in the garment and configured to monitor a cardiac activity of the patient. The cardiac monitoring circuitry comprises a plurality of separate and distinct modules that are integrated into and supported by the garment. The device further includes a controller configured to detect a cardiac condition of the patient based on the monitored cardiac activity of the patient. The plurality of separate and distinct modules comprises at least therapy control circuitry and energy storage devices disposed within at least one treatment module. The at least one treatment module is configured to be removably secured to the garment and to provide treatment to the patient based on the detected cardiac condition.

In some examples, the plurality of modules comprises low-voltage circuitry disposed within at least one low-voltage module and high-voltage circuitry disposed within at least one high-voltage module that is separate and distinct from the at least one low-voltage module.

In some examples, the low-voltage circuitry operates at a voltage of below about 100 volts.

In some examples, the high-voltage circuitry includes at least one component that operates at a voltage above about 100 volts.

In some examples, the low-voltage circuitry is configured to control at least one of: user interactions, cardiac signal acquisition and monitoring, cardiac arrhythmia detection, synchronization of defibrillation pulses with cardiac signals, treatment sequence, patient alerts, data communications, and data storage.

In some examples, the high-voltage circuitry comprises at least one of the therapy control circuitry and the energy storage devices.

In some examples, the plurality of modules comprises at least one processor disposed in an operations module separate from other modules to monitor the cardiac data received from the at least one electrode and communicate with the therapy control circuitry to direct administration of treatment to the patient.

In some examples, the plurality of modules comprises communications circuitry disposed in a communications module separate from other modules and configured to communicate with at least one external system.

In some examples, the energy storage devices are configured to store energy for at least one therapeutic pulse.

In some examples, the energy storage devices comprise a plurality of capacitors and at least one non-rechargeable battery to provide power to the plurality of capacitors.

In some examples, the energy storage devices are coupled to the therapy control circuitry and the therapy control circuitry is configured to control at least a discharge of energy from the energy storage module.

In some examples, the plurality of modules comprises a first energy storage device to store energy for a first portion of a therapeutic pulse and a second energy storage device, distinct from the first energy storage device, to store energy for a second portion of the therapeutic pulse.

In some examples, the plurality of modules comprises a first energy storage device integrated into a front portion of the garment and a second energy storage device integrated into a rear portion of the garment.

In some examples, the plurality of modules comprises a plurality of capacitors distributed about and integrated into the garment.

In some examples, at least one of the plurality of modules removably couples to a rechargeable battery.

In some examples, the garment removably couples to a rechargeable battery for powering one or more of the modules.

In some examples, the at least one therapy electrode is permanently integrated into the garment.

In some examples, the device further comprises at least one user interface integrated into the garment.

In some examples, the device further comprises at least one user interface communicatively coupled to at least one of the plurality of modules.

In some examples, the plurality of modules comprises ECG sensor circuitry configured to sense and process electrocardiogram (ECG) signals of the patient, acoustic sensor circuitry configured to detect and process heart and/or lung sounds of the patient, respiration sensor circuitry configured to sense and process respiration of the patient, and radio-frequency circuitry configured to detect and process fluid levels of the patient.

In some examples, the ECG sensor circuitry, the acoustic sensor circuitry, the respiration sensor circuitry, and the radio-frequency circuitry are disposed within the plurality of modules.

In some examples, the therapy control circuitry is configured to initiate a treatment to the patient based on one or more notifications regarding a cardiac arrhythmia.

In some examples, the treatment comprises at least one of a pacing therapy, a defibrillation therapy, and a transcutaneous electrical nerve stimulation (TENS) therapy.

In some examples, the garment comprises at least one of a vest worn about an upper boldy of the patient, a wrap-around garment, and a one-shoulder garment configured to be worn about one shoulder and wrap around an upper torso of the patient.

In some examples, the garment is configured to be machine washable, water resistant, and permeable to transmission of moisture and water vapor from an inner layer towards an outer layer of the garment, and comprises a low-skin irritation material.

In some examples, the garment is configured to have an average moisture transmission rate of between 100 $g/m^2/day$ to 250 $g/m^2/day$.

In some examples, the garment is configured to have an average moisture transmission rate of between 250 $g/m^2/day$ to 20,000 $g/m^2/day$.

In some examples, the garment is configured to have an average moisture transmission rate of between 20,000 $g/m^2/day$ to 50,000 $g/m^2/day$.

In some examples, the garment is configured to be air permeable to promote ventilation through the garment.

In accordance with at least one aspect, a wearable cardiac device is provided. The device comprises a garment configured to be worn about a torso of a patient, at least one sensing electrode disposed in the garment and configured to monitor cardiac activity of the patient, at least one therapy electrode disposed in the garment and configured to provide an electrical therapy to the patient based on the monitored cardiac activity, cardiac monitoring circuitry disposed in the garment and configured to monitor a cardiac activity of the patient and detect a cardiac condition of the patient based on the monitored cardiac activity of the patient and provide at least one therapeutic pulse to the patient based on the detected cardiac condition, the cardiac monitoring circuitry comprising a plurality of separate and distinct modules distributed about the garment, the plurality of separate and distinct modules comprising at least one high-voltage module and at least one low-voltage module, the high-voltage module comprises high-voltage circuitry operating at one or more high-voltage levels and the low-voltage module comprises low-voltage circuitry operating at below the one or more high-voltage levels, and conductive wire integrated into the garment to electrically couple at least two of the plurality of modules.

In accordance with at least one aspect, a wearable cardiac device is provided. The device comprises a garment configured to be worn about a torso of a patient, at least one sensing electrode configured to monitor cardiac activity of the patient, at least one therapy electrode configured to provide treatment to the patient, and cardiac monitoring circuitry comprising a plurality of separate and distinct modules distributed about the garment. The plurality of modules include an operations module coupled to the at least one sensing electrode and configured to detect at least one cardiac condition of the patient, an energy storage module coupled to the at least one therapy electrode and configured to store energy for at least one therapeutic shock to be applied to the patient, and a communications circuitry disposed within a communications module that is separate and independent from the operations module and the energy storage module and coupled to at least one of the operations module and the energy storage module, the communications circuitry configured to communicate with at least one external device.

In accordance with at least one aspect, a wearable cardiac device is provided. The device comprises a garment configured to be worn about a torso of a patient, at least one sensing electrode configured to monitor cardiac activity of the patient, at least one therapy electrode configured to provide treatment to the patient, and cardiac monitoring circuitry configured to detect a cardiac condition of the patient based on the monitored cardiac activity of the patient and provide at least one therapeutic pulse to the patient based on the detected cardiac condition, the controller comprising a plurality of separate and distinct capacitor modules, each capacitor module comprising a capacitor having a form factor adapted to be housed within a corresponding enclosure, the enclosure adapted to conform to a predetermined portion of a patient's body, each capacitor module coupled to the at least one therapy electrode and at least one charger circuit to charge the plurality of capacitors.

Other features and advantages of the invention will be apparent from the drawings, detailed description, and claims. Moreover, it is to be understood that both the foregoing information and the following detailed description are merely illustrative examples of various aspects, and are intended to provide an overview or framework for understanding the nature and character of the claimed subject matter. Any example disclosed herein may be combined with any other example. References to "an example," "some examples," "an alternate example," "various examples," "one example," "at least one example," "this and other examples" or the like are not necessarily mutually exclusive and are intended to indicate that a particular feature, structure, or characteristic described in connection with the example may be included in at least one example. The appearance of such terms herein is not necessarily all referring to the same example.

Furthermore, in the event of inconsistent usages of terms between this document and documents incorporated herein by reference, the term usage in the incorporated references is supplementary to that of this document; for irreconcilable inconsistencies, the term usage in this document controls. In addition, the accompanying drawings are included to provide illustration and a further understanding of the various aspects and examples, and are incorporated in and constitute a part of this specification. The drawings, together with the remainder of the specification, serve to explain principles and operations of the described and claimed aspects and examples.

BRIEF DESCRIPTION OF DRAWINGS

The accompanying drawings are not intended to be drawn to scale. In the drawings, components that are identical or nearly identical may be represented by a like numeral. For purposes of clarity, not every component is labeled in every drawing. In the drawings.

DETAILED DESCRIPTION

Figure 1:
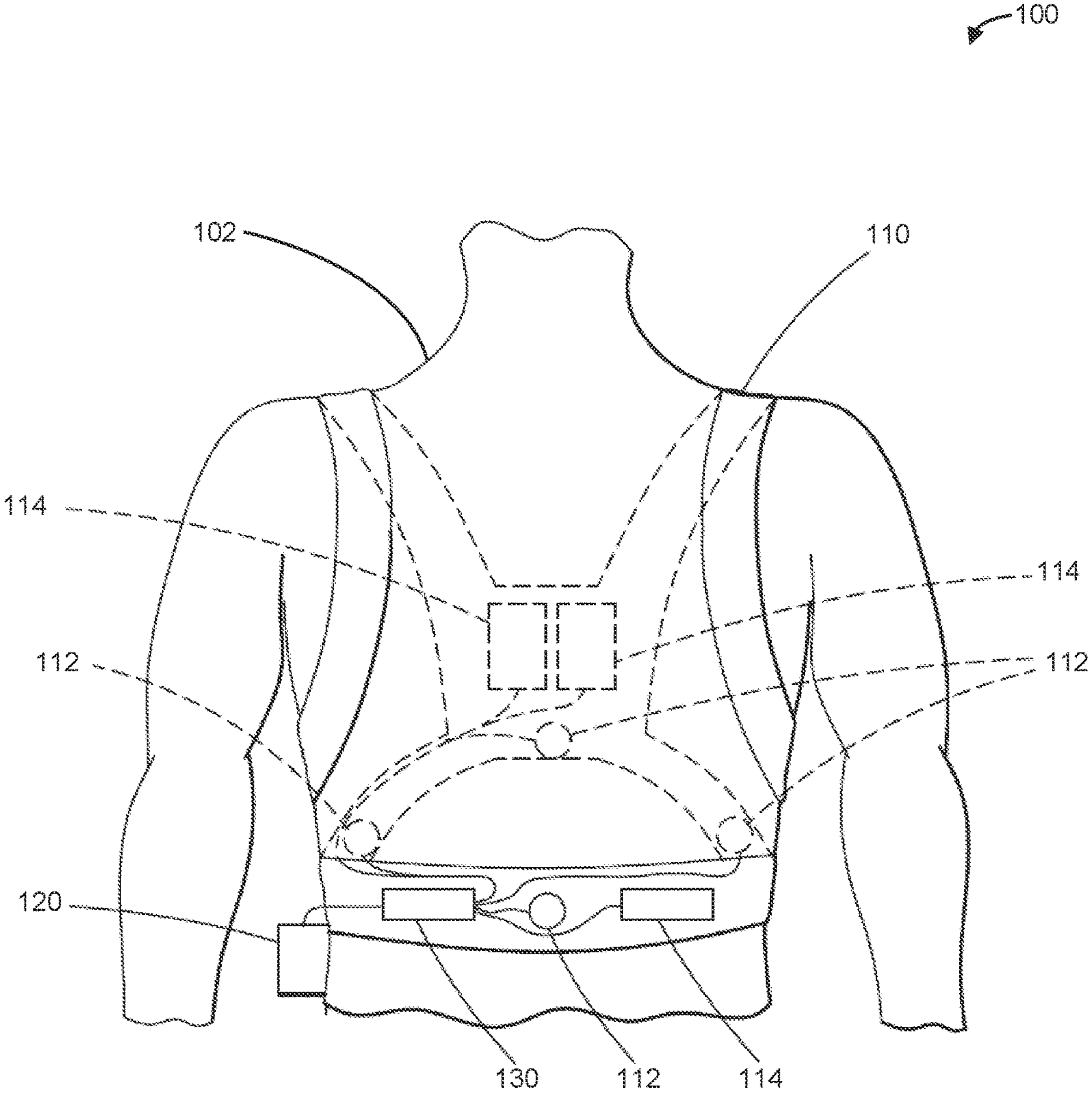
FIG. 1 (Prior Art)
FIG. 1 shows an example wearable defibrillator.

Systems and techniques as disclosed herein are provided to improve the ergonomics of various wearable medical devices. For example, wearable medical devices as disclosed herein may be cardiac devices that monitor a patient's physiological conditions, e.g., cardiac signals, respiratory parameters, patient activity, etc. For example, where such medical devices include cardiac monitors, they can be configured to determine whether the patient may be experiencing a cardiac condition, or allow a patient to report his/her symptoms and associating the patient's physiological data with such reports. The medical devices can include at least one or a plurality of sensing electrodes that are disposed at one or more locations of the patient's body and configured to detect or monitor the cardiac signals of the patient. In some implementations, the medical device can be configured to monitor other physiological parameters as described in further detail below. For example, such devices can be used as cardiac monitors in certain cardiac monitoring applications, such as mobile cardiac telemetry (MCT) and/or continuous event monitoring (CEM) applications. In addition to or instead of cardiac monitoring, such devices may also monitor respiratory parameters (e.g., to monitor congestion, lung fluid status, apnea, etc.), patient activity (e.g., posture, gait, sleep conditions, etc.) and other physiological conditions.

In some implementations, a medical device as disclosed herein can be configured to determine an appropriate treatment for the patient based on the detected cardiac signals (and/or other physiological parameters) and provide a therapy to the patient. For example, the device may cause one or more therapeutic shocks (e.g., defibrillating and/or pacing shocks) to be delivered to the body of the patient as described in further detail below. Accordingly, the medical device can include one or more therapy electrodes that are disposed at one or more locations of the patient's body and configured to provide treatment to the patient, for example, to deliver the therapeutic shocks.

A medical device as described herein can be configured to monitor a patient for a cardiac arrhythmia condition such as bradycardia, ventricular tachycardia (VT) or ventricular fibrillation (VF). In addition, while the detection methods and systems described hereinafter are disclosed as detecting VT and VF, this is not to be construed as limiting the invention as other arrhythmias, such as, but not limited to, atrial arrhythmias such as premature atrial contractions (PACs), multifocal atrial tachycardia, atrial flutter, and atrial fibrillation, supraventricular tachycardia (SVT), junctional arrhythmias, tachycardia, junctional rhythm, junctional tachycardia, premature junctional contraction, and ventricular arrhythmias such as premature ventricular contractions (PVCs) and accelerated idioventricular rhythm, may also be detected. In the case of treatment devices, such as, pacing and/or defibrillating devices, if an arrhythmia condition is detected, the device can automatically provide a pacing, defibrillation, and/or transcutaneous electrical nerve stimulation (TENS) pulses or shocks, as needed, to treat the condition. Defibrillation devices as described herein can include the capability of providing, in addition to defibrillating pulses, pacing pulses, TENS pulses, and other types of therapies.

Example Wearable Medical Device

The external medical device can be an in-facility continuous or substantially continuous monitoring defibrillator (e.g., for patients that are confined to a limited space within a facility, such as, a patient's room within a hospital environment) or outpatient wearable defibrillators. In some implementations, the medical device can be used in certain specialized conditions and/or environments such as in combat zones or within emergency vehicles. The medical device can be an ambulatory device (e.g., a device that is capable of and designed for moving with the patient as the patient goes about his or her daily routine).

For example, such an ambulatory medical device may be a wearable defibrillator (e.g., the LifeVest® wearable defibrillator available from ZOLL® Medical Corporation of Chelmsford, MA). FIG. 1 illustrates an example wearable medical device 100. The wearable medical device 100 includes a plurality of sensing electrodes 112 that can be disposed at various positions about the patient's body. The sensing electrodes 112 are electrically coupled to a medical device controller 120 through a connection pod 130. As shown in FIG. 1, the controller 120 can be mounted on a belt portion of the garment worn by the patient. The sensing electrodes 112 and connection pod 130 can be assembled into the garment 110 as shown. The sensing electrodes 112 are configured to monitor the cardiac function of the patient (e.g., by monitoring one or more cardiac signals of the patient) and thus may be referred to herein as cardiac sensing electrodes. For example, the connection pod 130 may include ECG signal acquisition circuitry for acquiring the sensed ECG signals from the sensing electrodes 112. The ECG signal acquisition circuitry also filters, amplifies, and digitizes the sensed ECG signals before sending them to the controller 120.

The wearable medical device 100 also includes a plurality of therapy electrodes 114 that are electrically coupled to the medical device controller 120 through the connection pod 130. The therapy electrodes 114 are configured to deliver one or more therapeutic defibrillating shocks to the body of the patient if it is determined that such treatment is warranted.

The controller 120 includes one or more user interface elements such as a response buttons and a touch screen that the patient can interact with in order to communicate with the medical device 100. The controller 120 also includes a speaker for communicating information to the patient and/or a bystander. In some examples, when the controller 120 determines that the patient is experiencing cardiac arrhythmia, the speaker can issue an audible alarm to alert the patient and bystanders to the patient's medical condition. In some examples, the controller 120 can instruct the patient to press and hold both response buttons on the medical device controller 120 to indicate that the patient is conscious, thereby instructing the medical device controller 120 to withhold the delivery of one or more therapeutic defibrillating shocks. If the patient does not respond to an instruction from the controller 120, the medical device 100 may determine that the patient is unconscious and proceed with the treatment sequence, culminating in the delivery of treatment (e.g., one or more defibrillating shocks) to the body of the patient.

Figure 2A:
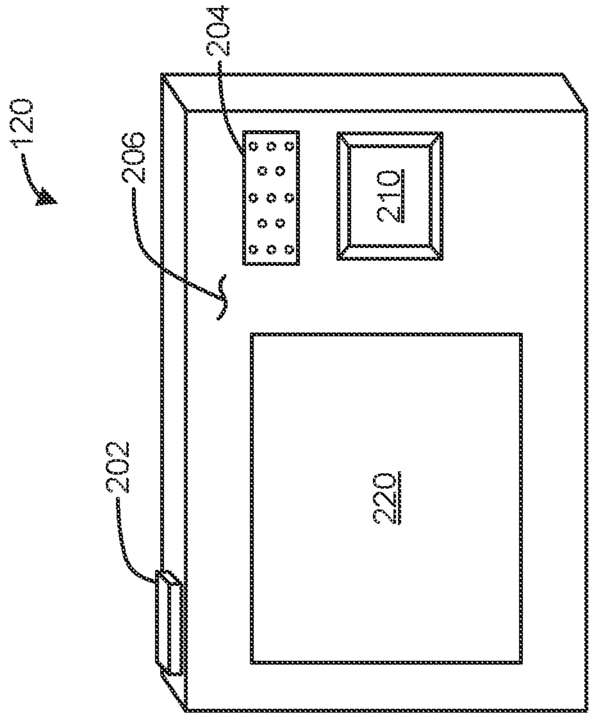
FIG. 2A (Prior Art)
FIGS. 2A and 2B show an example medical device controller.
Figure 2B:
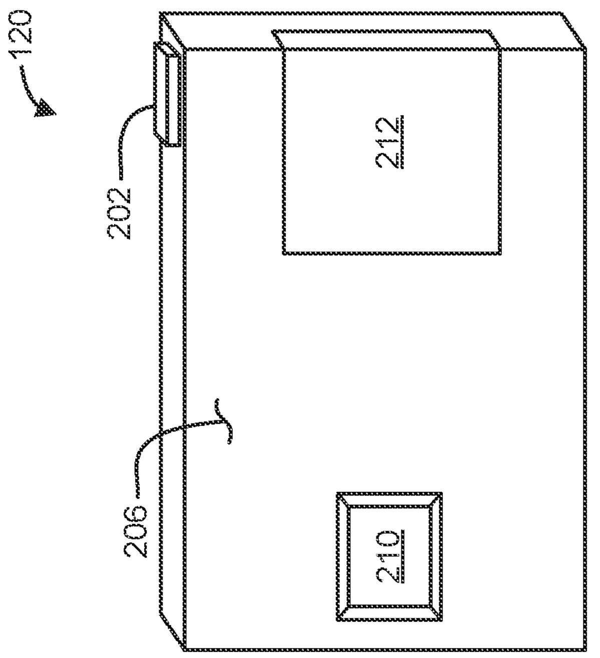
FIG. 2B (Prior Art)

FIGS. 2A-2B show an example of the medical device controller 120. The controller 120 may be powered by a rechargeable battery 212. The rechargeable battery 212 may be removable from a housing 206 of the medical device controller 120 to enable a patient and/or caregiver to swap a depleted (or near depleted) battery 212 for a charged battery. The controller 120 includes a user interface such as a touch screen 220 that can provide information to the patient, caregiver, and/or bystanders. The patient and/or caregiver can interact with the touch screen 220 to control the medical device 100. The controller 120 also includes a speaker 204 for communicating information to the patient, caregiver, and/or the bystander. The controller 120 includes response buttons 210. In some examples, when the controller 120 determines that the patient is experiencing cardiac arrhythmia, the speaker 204 can issue an audible alarm to alert the patient and bystanders to the patient's medical condition. The medical device controller 120 further includes a port 202 to removably connect sensing devices (e.g., ECG sensing electrodes 112) and/or therapeutic devices (e.g., therapy electrodes 114) to the medical device controller 120.

Example Integrated Garments

Advancements for the purpose of ambulatory (e.g., wearable) medical devices include garments that are constructed such that some or all of the device electronics are distributed as separate modules and integrated into the garment worn by the patient. The separate modules may be divided into sub-modules or modular components that are separate and distinct from one another. Groups of modular components may communicate with one another and collectively form or perform functions of respective modules as described herein. The separate modules may communicate with one another and collectively form or perform the function of a wearable medical device as described herein. For example, the device controller and connection pod described above (e.g., controller 120 and connection pod 130 of FIG. 1) may be divided into a plurality of modules and distributed and integrated into the garment in a variety of ways. For example, the controller 120 may comprise a plurality of separate and distinct capacitor modules or modular components. The integration into the garment can provide a number of benefits, for example, enhancing patient comfort and promoting modular use of the device. Such modules may be integrated, for example, by being permanently coupled to the garment such that the modules become an undetachable portion of the garment. The modules may then be coupled to each other by conductive threads or other communication and/or power transfer mechanisms as described below. Other techniques for integrating the modules into the garment may be employed. For example, one or more modules may be removably attached to the garment using one or more coupling mechanisms or fasteners such as Velcro® brand hook-and-loop fasteners, snaps (including conductive snaps), and zip fasteners.

In some implementations, a wearable cardiac monitoring/treatment device comprises a garment configured to be worn about a torso of a patient and patient monitoring circuitry disposed in the garment and configured to monitor one or more physiological signals from the patient. The patient monitoring circuitry comprises a plurality of separate and distinct modules or modular components communicatively coupled to one another via one or more communication links. The patient monitoring circuitry is configured to monitor at least a cardiac activity of the patient, detect the presence of a cardiac arrhythmia in the patient, and provide one or more notifications regarding the cardiac arrhythmia. The plurality of the separate and distinct modules or modular components are integrated into and distributed about the garment for an ergonomic fit on the patient. The patient monitoring circuitry may include ECG sensor circuitry configured to sense and process electrocardiogram (ECG) signals of the patient, acoustic sensor circuitry configured to detect and process heart and/or lung sounds of the patient, respiration sensor circuitry configured to sense and process respiration of the patient, and radio-frequency circuitry configured to detect and process fluid levels of the patient. The ECG sensor circuitry, the acoustic sensor circuitry, the respiration sensor circuitry, and the radio-frequency circuitry are disposed within the separate and distinct modules or modular components. The wearable cardiac monitoring/treatment device may further comprise high-voltage circuitry comprising therapy control circuitry and energy storage devices, the high-voltage circuitry being disposed within a treatment module or modular component that is configured to be separable from the wearable cardiac monitoring device.

In an implementation, the patient may select a portion of a multi-component medical device as described herein for certain uses, and the full medical device for other uses. As an example, in the case of a patient deemed low risk for developing cardiac conditions during a certain period, the patient may use the garment comprising only the physiological monitoring components (e.g., with the treatment modules removed) for use during that period. For instance, the period may be during the performance of an activity such as showering. In another example, the patient may remove one or more communications and/or user interface modules (as described in further detail below) from the garment for a period of time, while still being actively monitored for one or more physiological conditions.

Aspects of the present disclosure manifest an appreciation of various challenges for patients to live with a wearable medical device for an extended period of time. For example, a patient may have experienced a recent cardiac event and be at a high risk for sudden cardiac arrest (SCA) in the immediate or substantially immediate future (e.g., as determined by a physician, such risk may be expressed in terms of a heightened likelihood of an event occurring in the next few hours, days, or weeks). The patient may be prescribed a wearable defibrillator by a physician to wear for multiple days or weeks until the risk of SCA subsides or until the patient may be fitted with an implanted defibrillator. The patient may have to go about their daily life with the wearable medical device including, for example, sleeping, attending work, shopping, exercising, and/or operating a motor vehicle. In addition, the patient may not wish for the wearable medical device to be easily visible by others and, thereby, display the patient's condition to the general populace.

The garments as disclosed herein for such wearable medical devices are capable of providing an ergonomic fit on the patient, e.g., capable of providing optimum fit and comfort for an extended period of time and/or to avoiding stress or injury to the patient. For example, such a garment may comprise at least an anterior portion (e.g., a flexible, substantially rigid, or substantially semi-rigid fabric or other material-based element of the garment disposed about the front of the patient) and a posterior portion (e.g., a flexible, substantially rigid, or substantially semi-rigid fabric or other material-based element of the garment disposed about the rear of the patient). In some implementations, the anterior portion may be coupled or connected to the posterior portion through one or more side portions. In some implementations, the anterior portion may be coupled or connected to the posterior portion through one or more shoulder portions or straps. For example, a shoulder portion or strap may include a harness configured to support the rest of the garment and/or the garment components over one or more of the patient's shoulders. One or more of the anterior, posterior, side, and shoulder portions may be a formed of a single continuous wearable garment. In some implementations, one or more of the anterior, posterior, side and/or shoulder portions may be independent and separable from each other. Further, one or more of the above portions may be omitted and/or replaced by an alternative connecting structure without significantly departing from the scope of the principles described herein. Such portions may be configured to removably connect or couple to one other. For example, such an ergonomically fitted garment may evenly distribute the weight of the components of the wearable medical device about the one or more portions of the garment as described herein to make the wearable medical device less cumbersome. Further, in some implementations, loose cables that may be easily snagged on objects may be permanently disposed with the garment and/or snugly secured into the garment in a removable manner. In an example, in addition to dividing up the weight of the wearable medical device, various garment configurations are also disclosed herein to, for example, reduce the visibility of the wearable medical device and/or make the wearable medical device easier to don. These garments may also be washable, for example, machine washable, to allow a user to easily launder the garment and/or water resistant/waterproof to allow a patient to bathe with the wearable medical device.

In various embodiments, the garment may be configured to be worn about a torso of a patient, may be a vest worn about an upper body of the patient, a wrap-around garment, or a one-shoulder garment configured to be worn about one shoulder and wrap around an upper torso of the patient.

Further, the garment may include an exterior surface (e.g., a surface of the garment, including portions thereof, facing away from the patient's skin) and an interior surface (e.g., a surface of the garment, including portions thereof, facing towards the patient's skin) that each have different material characteristics and/or design purposes. For example, the garment can be constructed such that the exterior surface of the garment is water resistant and substantially prevents ingress of water while an interior surface of the garment can be configured to substantially allow moisture vapor (such as generated from the patient's skin) to be transferred away from the patient's skin. The garment may be permeable to transmission of moisture and water vapor from an inner layer towards an outer layer of the garment. Such a garment can be constructed of a single fabric and/or material comprising both the interior and exterior surfaces. In some implementations, the garment can be constructed from a single fabric and/or material that may be laminated and/or coated on one or both sides with other materials. For example, such material may be cotton, nylon, polyester, and/or a blend of such materials, and may be laminated or coated on one or both sides with polytetrafluoroethylene, expanded polytetrafluoroethylene (e.g., Teflon® materials), and/or polyurethane materials. The garment may be constructed of a low-skin irritation material. The garment may be air permeable to promote ventilation through the garment.

In some implementations, the garment may comprise one or more layers of fabric or other material, with at least an outer layer forming the exterior surface of the garment and an inner layer forming the interior surface of the garment. Additional layers may be disposed between the inner and outer layers. Further, the outer, inner, and/or the additional layers may have different material characteristics and/or purposes. For instance, the inner layer of the garment can be breathable, e.g., permeable to moisture and/or water vapor such that moisture and/or water vapor can pass from the inner layer towards the outer layer based on a predesigned moisture transmission rate. For example, the transfer of such moisture may be expressed in terms of an average moisture transmission rate, and may be designed to be greater than about 100 $g/m^2/day$. In some implementations, the average rate may be greater than about 250 $g/m^2/day$. Depending on a material type selected for the one or more layers, the selected average moisture transmission rate may be varied, such that in various implementations, the garment may have an average moisture transmission rate of between about 100 $g/m^2/day$ and about 250 $g/m^2/day$, between about 250 $g/m^2/day$ and about 20,000 $g/m^2/day$, or between about 20,000 $g/m^2/day$ and 50,000 $g/m^2/day$.

The outer layer may be based on hydrophobic and/or super-hydrophobic materials, e.g., materials that repel water or moisture from the outer layer. For example, some materials used in the garment may have an average moisture transmission rate greater than 20,000 $g/m^2/day$ (for example, 20,000 $g/m^2/day$ to 50,000 $g/m^2/day$). Materials for this purpose can include nylon, polyester, and may be laminated or coated based on polytetrafluoroethylene, expanded polytetrafluoroethylene (e.g., Teflon® materials), and/or polyurethane materials.

For example, the moisture transmission rate or moisture vapor resistance through the one or more layers of the garment can be optimized based on subjecting the fabric to tests such as the upright cup method (ASTM E96-80-Procedure B) and the Sweating Hotplate Method (ISO 11092). In brief, the upright cup method determines water loss from a dish covered with a sample of the fabric over a predetermined period of time. The result may be expressed in g/m$^2$/day. The Sweating Hotplate Method determines evaporative heat loss over a gradient of water vapor pressure. The result may be expressed in m$^2$ Pa/W. One or more layers of the garment may be designed to optimize patient comfort and garment durability based on the results of such tests. In addition, one or more layers of the garment may be subject to tests for measuring wicking or water transport properties through fabrics, including longitudinal wicking "strip" tests, transverse or transplanar wicking plate tests, aerial wicking spot tests, and Syphon tests. Details of such tests can be found in Harnett, P. R. and Mehta, P. N., A Survey and Comparison of Laboratory Test Methods for Measuring Wicking, Textile Research Journal, July 1984.

Further, in some implementations, the garment may be configured to be air permeable and configured to promote ventilation through the garment at a predesigned rate to enhance long term patient comfort and garment durability. For instance, materials such as polyethylene, polypropylene, and/or urethane film may be used in constructing the one or more layers of the garment.

In some examples, the weight is distributed about the garment by dividing the various patient monitoring and/or treatment components into a plurality of modules and distributing the plurality of modules about the various portions of the garment. For example, such modules may include device electronics in housings that are constructed to be impermeable to ingress of water. For instance, the modules and/or subsystems described herein can be protected against, for example, condensation or dripping water (e.g., vertically dripping water), water dripping at one or more angles (e.g., between about 15 degrees and about 60 degrees from vertical), water splashing from any angle, low pressure water stream from any angle, high pressure water stream from any angle, water immersion (e.g., immersion for periods of about 30 minutes at a depth of about 1 meter as required for an appropriate Ingress Protection rating, defined by international standard EN 60529, British BS EN 60529: 1992, European IEC 60509:1989), and/or continual water submersion in under water conditions. The garment may be constructed to include one or more of the plurality of modules between one or more layers of the garment (e.g., an inner and outer layer of the garment as described above). The plurality of modules may be coupled by one or more wires, cables, and/or conductive threads to form an assembly that is removable from the garment. In another example, the plurality of modules may be coupled by one or more cables to form an assembly that is permanently disposed within and a part of the garment. For example, one or more of the modules may be permanently held in place within the garment by stitching, riveting, and/or garment fasteners disposed around a periphery and/or over a housing of the one or more modules, thus substantially fastening the one or more modules to the garment.

For example, a first subset of the plurality of modules may be interconnected with each other through a first one or more wires or cables and a second subset of the plurality of modules may be interconnected with each other through a second one or more wires or cables. Each subset and corresponding wires or cables may be removable from the garment. For example, each of the modules in the assembly may attach to the garment by one or more fasteners at various locations on the garment. The fasteners employed to removably secure the assembly to the garment may include, for example, hook-and-loop fasteners, snaps, and zip fasteners.

For example, the garment may operably couple to the modules by conductive hook-and-loop fasteners, conductive snaps, infrared (IR) coupling, capacitive coupling, inductive coupling, and/or conductive magnets. The modules may be removably secured to the garment by the same mechanism employed to operably couple the garment to the module (e.g., by the conductive hook-and-loop fasteners) and/or by a separate mechanism. For example, the garment may include pockets and/or sleeves to receive the modules and secure the modules in place on the garment.

In other examples, the plurality of modules or a subset of the plurality of modules, in addition to associated wires or cables interconnecting the plurality or subset of the plurality of modules, are permanently coupled such that the modules become an undetachable portion of the garment. For example, the components of one or more modules may be coupled to each other by conductive threading, wiring, or cables. It is appreciated that other techniques may be employed to operably couple the plurality of modules. For example, the plurality of modules may wirelessly communicate by various wireless (e.g. radio frequency) communication methods, fiber optics, and/or by a body area network (BAN) standard protocol (IEEE 802.15.6 standard).

The wearable medical device, in some examples, may include various monitoring components to monitor a condition of the patient and treatment components to provide therapy to the patient. In these examples, the treatment components may be separable from the monitoring components to enable a user (e.g., a patient) to re-configure the medical device as a treatment device or a monitoring device as appropriate. Enabling the user to re-configure the wearable medical device may advantageously allow the patient to wear a lighter wearable medical device in situations where the condition of the patient does not necessitate the treatment components. In these examples, the wearable medical device may monitor the condition of the patient and notify the patient of a change in condition that may necessitate the treatment components. In some implementations, the treatment components may have a separate treatment processor for controlling the treatment protocol, and in some cases, for handling the issuance of alarms relating to the treatment protocol. For example, the treatment protocol can include detecting patient response to an alarm regarding an impending treatment, initiating a treatment sequence if no response from the patient is detected, deploying conductive gel substantially proximate to the treatment site (where such gel is used), charging the energy storage devices to get them ready for charge delivery, and issuing one or more shocks to the patient based on the detected condition. Accordingly, when the wearable medical device is worn by the patient without the treatment components, one or more processors (e.g., the main processor in the wearable medical device) can be configured to only monitor for and issue any alerts with respect to cardiac or other physiological conditions detected in the patient. In one example, when the treatment components are included in the garment, the treatment processor may be disabled, and the main processor may automatically re-configure itself to manage the treatment protocol. In another example, when the treatment components are included in the garment, the treatment processor may continue to manage the treatment protocol, and the main processor may be configured to monitor the patient for treatable physiological conditions and if such a condition is detected, the main processor may cause the treatment processor to initiate the treatment protocol.

One or more of the modules may be disposed within a conformal housing or enclosure configured to be included within or integrated into a garment worn by the patient. For example, referring to FIGS. 16A and 16B, in some examples, at least one of the housings or enclosures for the device may be specifically molded to conform to the unique shape of each patient, for example, to the shape between a patient's shoulder blades or to the small of a patient's back. A housing or enclosure shaped as a conventional box may be noticeable and uncomfortable for a patient as compared to a housing or enclosure with the same volume, but which conforms to the patient's anatomical surface. The overall dimensions of the combined package of the inner housing containing the electronics and other components and the outer conformal housing may be larger than what might be obtained with just the inner housing, but because of the conforming features of the outer surface, the housing is configured to be comfortable for the patient, including while the patient is asleep. Because of the conformability as described herein, the wearable device may also be suitable for active use, such as jogging, dancing, or sports. A conformal housing may be configured for reducing shifting of the housing when the patient is engaging in these activities, e.g., through a conforming configuration that is better able to closely fit against the patient.

Figure 16A:
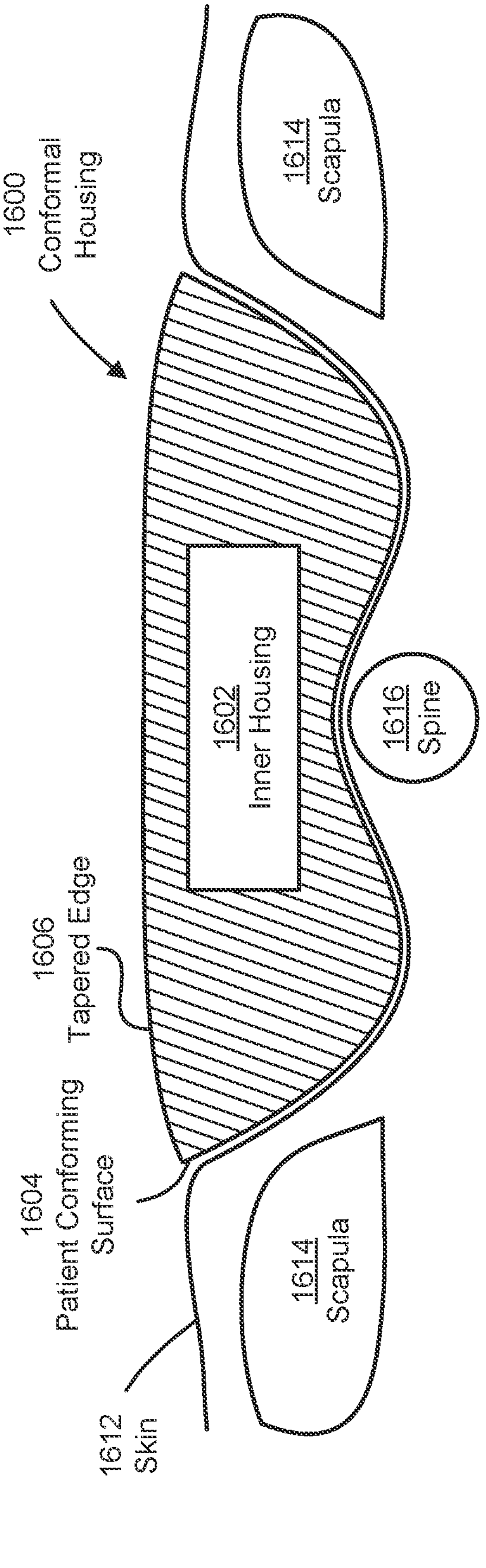
FIGS. 16A and 16B show conformal housings for modules.

For example, as shown in FIG. 16A, a conformal housing 1600 when applied over the inner housing 1602, may have, in addition to a patient conforming surface 1604 facing the patient to conform to the patient's shape, tapered edges 1606 that gradually blend the edges of the device with the surface of the patient. In this fashion, when the patient is lying on top of the conformal housing 1600, for instance when sleeping at night, the sensation of lying on the device will feel more like lying on a pillow rather than lying on a brick. In some examples, the inner housing 1602 contains all the electronics, power supply, among others, and may have a thickness of approximately 12 to 1". In some implementations, the overall size may be designed to fit in between the patient's scapula 1614, with a width of approximately 6 inches. In these implementations, the conformal housing may be constructed with a recess to fit up against the spine 1616 of the patient. Some other examples of possible locations for the conformal housings are in the small of the back, in the region of the axillae, or around the waist.

In some versions, the inner housing 1602 may contain a therapeutic delivery element such as a defibrillation electrode used on a LifeVest® wearable defibrillator from ZOLL® Medical Corporation of Chelmsford, MA. The conformal housing 1600 in such instances may be configured to have at least one hole on the surface facing the patient to allow for a therapeutic agent to be ejected by the therapeutic delivery element. The therapeutic agent may be conductive gel to, for example, reduce the impedance between the therapeutic delivery element and the skin of the patient 1612.

In one example, a flexible, compressible foam outer housing may be molded for each patient based on a three-dimensional representation generated by a 3D surface imaging technology with anatomical integrity, for instance the 3dMDthorax System (3dMD LLC, Atlanta GA). The conformal housing 1600 may be fabricated using a 3D printer system such as the ProJet 4500 full-color plastic printer (3DSystems Rock Hill SC) using, for example, the VisiJet C4 Spectrum plastic material. It is appreciated that the conformal housing 1600 may be constructed using other methods and/or other materials.

Figure 16B:
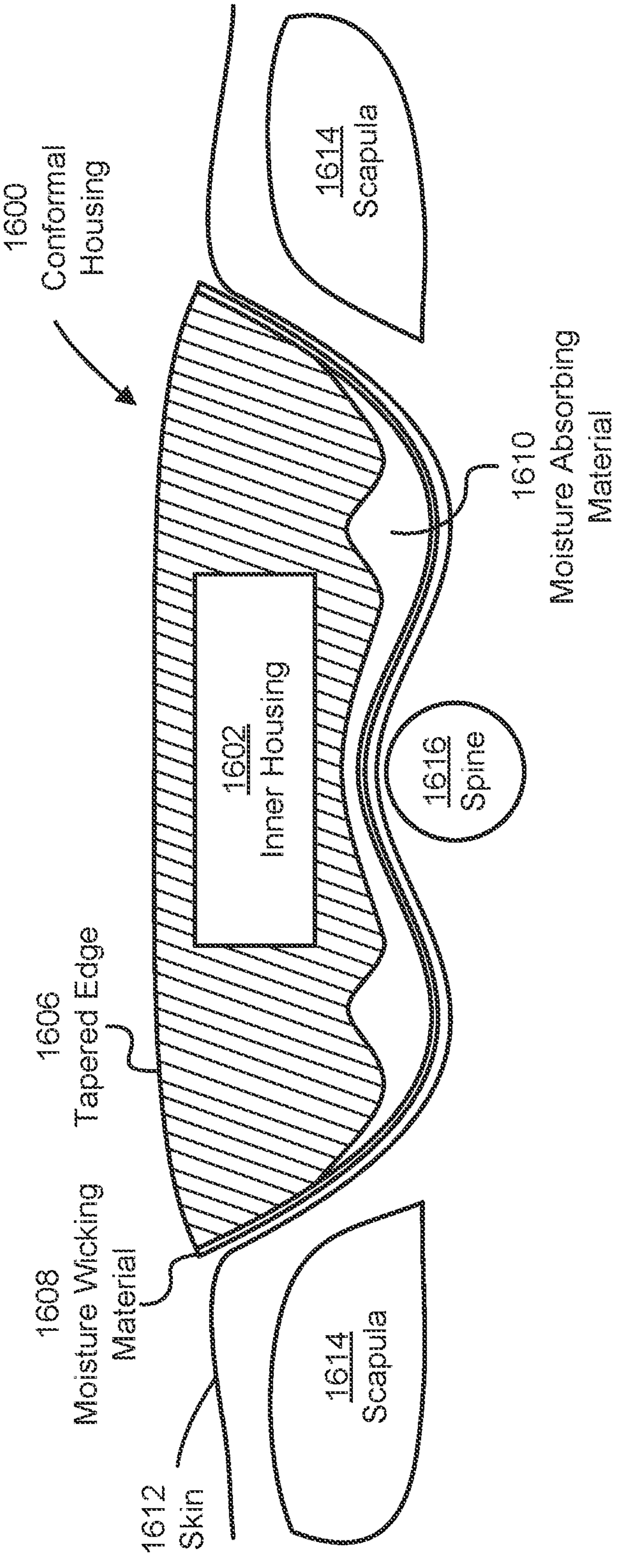

In some examples, as shown in FIG. 16B, a disposable, moisture wicking material 1608 may be interposed between the conformal housing 1600 and the patient's skin 1612. The wicking material may be composed of a material such the Coolmax (Dupont) polyester fabric that has enhanced capillary and wicking action. An additional moisture absorbing layer 1610 in between the moisture wicking material and the conformal housing 1600 may also be added to further enhance the comfort of the system and draw more moisture from sweat away from the patient's skin 1612. The moisture absorbing layer 1610 may contain materials such as powdered sodium polyacrylate, such as is used in commercial diapers or sanitary napkins that can absorb up to, e.g., about 800 times its weight in water.

The wearable devices as described herein may be capable of continuous, substantially continuous, long-term and/or extended use or wear by, or attachment or connection to a patient. For example, devices as described herein may be capable of being used or worn by, or attached or connected to a patient, without substantial interruption, for example, up to hours or beyond (e.g., weeks, months, or even years). In some implementations, such devices may be removed for a period of time before use, wear, attachment, or connection to the patient is resumed, e.g., to change batteries, to change or wash the garment, and/or to take a shower, without departing from the scope of the examples described herein.

In addition to cardiac monitoring, the medical device may be capable of monitoring a patient for other physiological conditions. For example, the device may be configured to monitor blood oxygen, temperature, glucose levels, sleep apnea, snoring, and/or other sleep conditions, heart sounds, lung sounds, tissue fluids, etc. using a variety of sensors including radio frequency (RF) sensors, ultrasonic sensors, electrodes, etc. In some instances, the device may carry out its monitoring in periodic or aperiodic time intervals or times. For example, the monitoring during intervals or times can be triggered by a user action or another event. For example, one or more durations between periodic or aperiodic intervals or times can be user-configurable.

In some implementations, the sensing and/or therapy electrodes are disposed on disposable adhesive electrode patches and coupled to the medical device. In some implementations, the sensing and therapy electrodes are disposed on a single integrated disposable adhesive electrode patch and coupled to the medical device. In some implementations, the medical device as described herein can be configured to monitor a patient presenting with syncope (e.g., by analyzing the patient's cardiac activity for aberrant patterns that can indicate abnormal physiological function).

Example Integrated Garment Subsystems

Figure 3:
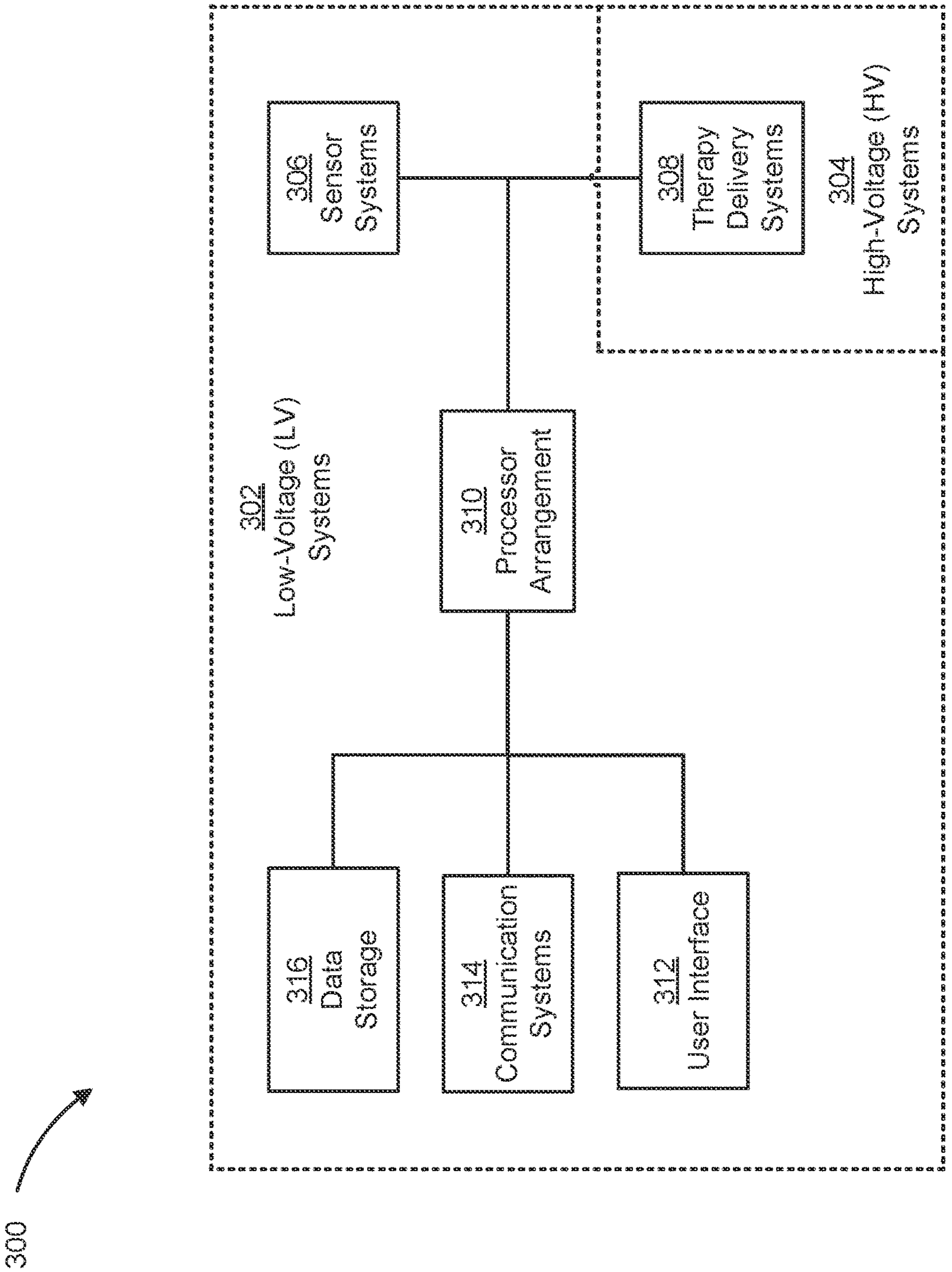
FIG. 3 shows a schematic block diagram of an example wearable medical device.

The various components of a wearable medical device (including, for example, a device controller and/or a connection pod) may be organized into one or more modules or subsystems as illustrated by the schematic block diagram of an example wearable medical device 300 in FIG. 3. The wearable medical device 300 includes sensor systems 306, therapy delivery systems 308 including therapy control circuitry, a processor arrangement 310, a user interface 312, communication systems 314, and data storage 316. The sensor systems 306 are operatively connected to one or more patient sensing elements (e.g., ECG sensors, heart sound sensors, and the like). The therapy delivery systems 308 are operatively connected to one or more therapy electrodes or other therapy delivery elements. Therapy control circuitry in the therapy delivery systems 308 may be configured to initiate a treatment to a patient based on one or more notifications regarding a cardiac arrhythmia detected in the patient. Therapy control circuitry in the therapy delivery systems 308 may be configured to provide at least a pacing therapy, a defibrillation therapy, and a transcutaneous electrical nerve stimulation (TENS) therapy to the patient. It is appreciated that the wearable medical device 300 may include other components that are not illustrated in FIG. 3 including, for example, a power source such as a battery. As described above, each of the subsystems and/or modules may be disposed within a corresponding housing that is shaped and configured to be included within or integrated into a garment worn by the patient.

In some implementations, the various subsystems illustrated in FIG. 3 may be divided into low-voltage (LV) systems 302 and high-voltage (HV) systems 304. Dividing the wearable medical device into LV systems 302 and HV systems 304 may be advantageous to reduce electrical interference between the HV systems 304 and the other components. Thereby, the HV systems 304 may be packaged together and located in modules that are separate (and, in some cases, distal) from the LV systems 302 and/or shielded from the LV systems 302. High-voltage circuitry included in the wearable cardiac monitoring device, for example, in the HV systems, may include therapy control circuitry and energy storage devices. The high-voltage circuitry may be disposed within a treatment module or modular component that is configured to be separable from the wearable cardiac monitoring device. It is appreciated that the below description is based on dividing the wearable medical device based on the operating voltage of the various components of the device (e.g., into LV systems and HV systems); however, there may be other ways to separate the various components of the device. For instance, it may be desirable to divide the device based on one or more functions of the various components of the device. As such, a communications module may include communications circuitry as described below, an energy storage module may include one or more capacitors for storing electric charge, a self-testing module may be configured to oversee periodic and aperiodic self-testing of the various aspects of the device, and a power module for ensuring that the battery is maintained within operating range and ready to charge the one or more capacitors when needed. In some examples, the HV systems 304 may be one or more systems or may include one or more components that operate at voltage levels of about hundreds to thousands of volts. In an implementation, the HV systems 304 may be one or more systems that operate at voltage levels of between 25%-100% of the peak voltage value of one or more therapeutic pulses. For example, the therapy delivery systems 308 may provide therapeutic pulses (e.g., defibrillation pulses) at a peak voltage of approximately 1600 volts. In this example, the HV systems may have one or more components that operate at a voltage above approximately 400 volts (e.g., 25% of the peak voltage) including, for example, a high voltage converter. It is appreciated that other voltage delineations may be employed to separate the HV systems from the LV systems depending upon the particular implementation. For instance, the HV systems 304 may be systems with one or more components that operate at a voltage level in excess of 100 volts. Accordingly, in some implementations, the high-voltage module may include one or more components that operate at voltage levels of between about 100 V and about 2000 V, or between about 400 V and about 2000 V, or between about 500 V and about 2000 V.

The LV systems may be systems with components that operate below (and/or substantially below) the operational voltage level of the HV systems 304, e.g., less than 100 volts. For example, the sensor system 306, processor arrangement 310, user interface 312, communications systems 314, and/or data storage 316 may all operate at voltages that are substantially lower than 100 volts. For example, the LV systems may include components that operate at voltage levels of between about 1 mV and about 5 V. In some examples, the LV systems may include components that operate at voltage levels of between about 5 V and about 100 V. It is appreciated that the 100 volt level delineation between HV systems 304 and LV systems 302 may be adjusted based on the particular implementation. For example, the therapy delivery systems 308 may operate at a voltage level of 500 volts and the delineation between the LV systems and the HV systems may be a voltage level that is between 500 volts and the operating voltage of the remaining components of the wearable medical device. Further, it is appreciated that, in some implementations, the HV systems 304 may include one or more LV components. For instance, such LV components may be associated with implementing and/or controlling some or all of the HV components.

The therapy delivery systems 308 may include systems to provide therapy to the patient via one or more therapy electrodes (e.g., therapy electrodes of FIGS. 10A and 10B) and/or therapy delivery elements. For example, the therapy delivery systems 308 may include various devices to provide therapeutic pulses to the patient including, for example, TENS pulses, pacing pulses, and/or defibrillation pulses. The therapeutic pulses may be generated by charging a capacitor bank and discharging the energy stored in the capacitor bank into the patient. For example, the therapy delivery systems 308 can include one or more power converters for controlling the charging and discharging of the capacitor banks. In some implementations, the discharge of energy from the capacitor bank may be controlled by, for example, an H-bridge circuit as described in U.S. Pat. No. 6,280,461, titled "PATIENT-WORN ENERGY DELIVERY APPARATUS," issued on Aug. 28, 2001 (hereinafter the "'461 Patent"), and U.S. Pat. No. 8,909,335, titled "METHOD AND APPARATUS FOR APPLYING A RECTILINEAR BIPHASIC POWER WAVEFORM TO A LOAD," issued on Dec. 9, 2014 (hereinafter the "'335 patent"), each of which is hereby incorporated herein by reference in its entirety.

In some examples, the therapy delivery systems 308 may include one or more therapy delivery mechanisms including various drug delivery devices or one or more components for delivering a drug therapy to a patient. For example, the therapy delivery systems 308 may include devices for intravenous delivery and/or patch absorption of a drug. The patch absorption devices may include a micro-needle array including dozens of microscopic needles (e.g., each far thinner than a strand of hair) that are coated and/or filled with a drug to administer to the patient. Employing a micro-needle array for drug delivery may be advantageous in some examples because the needles are so small that they don't reach nerves in the skin and, thereby, deliver a drug with minimal pain experienced by the patient. In some implementations, the therapy delivery mechanisms may include a microneedle array based electrode patch for delivering therapeutic electrical energy through the patient's skin. It is appreciated that the therapy delivery systems 308 may, in some implementations, include one or more therapy delivery mechanisms that do not require a high voltage including, for example, some drug delivery devices.

The therapy delivery systems 308 may include gel deployment circuitry configured to cause the delivery of conductive gel substantially proximate to a treatment site (e.g., a surface of the patient's skin in contact with the therapy electrode) prior to delivering therapeutic shocks to the treatment site. The gel deployment circuitry may be configured to cause the delivery of conductive gel immediately before delivery of the therapeutic shocks to the treatment site, or within a short time interval, for example, within about 1 second, 5 seconds, 10 seconds, 30 seconds, or one minute before delivery of the therapeutic shocks to the treatment site. Such gel deployment circuitry may be coupled to or integrated within a therapy electrode or other therapy delivery device as a single unit. When a treatable cardiac condition is detected and no patient response is received after device prompting, the gel deployment circuitry can be signaled to deploy the conductive gel. In some examples, the gel deployment circuitry may be constructed as one or more separate and independent gel deployment modules. Such modules may be configured to receive removable and/or replaceable gel cartridges (e.g., cartridges that contain one or more conductive gel reservoirs). As such, the gel deployment circuitry may be permanently disposed in the garment as part of the therapy delivery systems, while the cartridges may be removable and/or replaceable.

In some implementations, the gel deployment modules may be implemented as gel deployment packs and include at least a portion of the gel deployment circuitry along with one or more gel reservoirs within the gel deployment pack. In such implementations, the gel deployment pack, including the one or more gel reservoirs and associated gel deployment circuitry may be removable and/or replaceable, e.g., in a manner shown below in connection with FIGS. 10A and 10B. In other examples, the gel deployment pack, including the one or more gel reservoirs and associated gel deployment circuitry, and the therapy electrode can be integrated into a therapy electrode assembly that can be removed and replaced as a single unit either after use, or if damaged or broken.

The sensor systems 306 include systems to sense various physiological parameters of the patient. For example, the sensor systems 306 may include ECG electrodes to monitor an ECG of the patient, acoustic sensors to monitor the heart and/or lung sounds of the patient, respiration monitors to monitor the respiration of the patient, such as during a sleep study or when monitoring for sleep apnea, and/or radio-frequency based fluid monitoring sensors. Other example physiological parameters that may be monitored by the sensor systems 306 include patient movement, patient's body state (such as standing, supine, etc.), patient's posture, lung sounds, tissue fluids, lung fluid, oxygen levels, and/or blood pressure level. The sensor systems 306 may further include various sensor acquisition circuits to, for example, filter and/or pretreat the sensor signals prior to providing the sensor signals to the processor arrangement 310.

The sensor system 306 can include a sensor in one or more locations in the garment for monitoring patient heart and/or lung sounds, patient sleep, activity, and other types of body sound or patient activity. For example, the sensor can comprise a three axis multiple-channel MEMS accelerometer, e.g., a three-channel accelerometer. A first channel can be configured to monitor sounds produced by the patient's heart, a second channel can be configured to monitor a respiration of the patient, and a third channel can be configured to monitor patient movements. For example, such a sensor is described in U.S. Patent Publication No. 2015/0005588, titled "THERAPEUTIC DEVICE INCLUDING ACOUSTIC SENSOR," published on Jan. 1, 2015 (hereinafter the "'588 publication"), which is hereby incorporated herein by reference in its entirety. The sensor can be configured to be in communication with a recording system (e.g., a local storage module or a remote server) for storage and analysis. In some implementations, the sensor system 306 can be configured to be coupled to at least one of the communications module 408 and the user interface module 410 for providing alerts to the patient, patient's caregiver, a loved one and/or other alert mechanisms. For example, the sensor system 306 can be configured to analyze the signals indicative of the sounds produced by the patient's heart and be further configured to warn the patient and/or another entity in the event sounds are detected that are indicative of an abnormal cardiac or other condition of the patient. In some implementations, the sensor system 306 can be configured to include a processor for performing the above analysis based on one or more software modules stored on the processor. For example, such a processor can be physically coupled substantially proximate to the one or more sensors of the sensor systems 306. In another example, the processor can be within the processor arrangement 310 described below.

In some examples, the processor arrangement 310 can perform a series of instructions that control the operation of the other components of the wearable medical device 300. The processor arrangement 310 may execute one or more software components stored in, for example, data storage 316. These software components may include cardiac monitoring components configured to identify cardiac arrhythmias. In some implementations, the software components may include acoustic sensors for monitoring heart sounds and movement and/or lung sounds during a sleep study or sleep apnea monitoring. In some implementations, the software components may operate and monitor acoustic sensors for monitoring heart sounds and movement and/or lung sounds and may combine information from such sensors with ECG information for processing and analysis.

The sensor system 306 can include a pulse oximetry sensor configured to monitor the patient's oxygen saturation. For example, the sensor can be disposed in a pocket or other receptacle within the garment, and can be removed and coupled to one or more of the integrated modules in the garment. For example, the sensor can be removed from the pocket in the garment and placed on a finger, and communicatively coupled (e.g., electrically coupled via a cord, wirelessly coupled, optically coupled, etc.) to a processor disposed in the garment. For example, the processor may be part of the processor arrangement 310 as described in further detail below. For example, the sensor can be coupled to a handheld device (e.g., a smartphone or tablet) or a wrist mounted device such as a watch. The handheld device may include software components configured to receive the signals from the sensor and store and/or process such signals for analysis.

The processor arrangement 310 may include a plurality of processors and/or multi-core processors coupled to a shared memory (e.g., a memory module accessible for read and/or write by any of the plurality of processors or processor cores). In some implementations, each processor and/or processor core may be configured to operate with a corresponding independent memory module. In some examples, each processor of the plurality of processors in the processor arrangement may be configured to perform a sub-set of the tasks performed by the processor arrangement 310. For example, the processor arrangement 310 may include a digital signal processor (DSP) that receives and analyzes the sensor data to identify medical conditions that require treatment and a general purpose processor that controls the user interface components as described in U.S. Pat. No. 8,904,214, titled "SYSTEM AND METHOD FOR CONSERVING POWER IN A MEDICAL DEVICE," issued on Dec. 2, 2014 (hereinafter the "'214 patent"), which is hereby incorporated herein by reference in its entirety.

In some examples, the processor arrangement 310 includes a LV processor to manage the LV systems 302 and a HV processor to manage the HV systems 304. The LV and HV processors may be located within, for example, a processor module and in communication with the HV and LV systems or located within the module (or one of the modules) that the respective processor controls.

In some implementations, the LV processor may be configured to, for example, acquire data from the sensor systems 306, initiate communication with an external system via the communication systems 314, provide notifications to external entities via the user interface 312, and/or store sensor data in the data storage 316. The HV processor may be configured to, for example, control charging of the capacitor bank and/or the administration of therapeutic pulses to the patient. It is appreciated that the HV processor may operate at a low voltage and need not operate at the same voltage as the HV systems that the HV processor controls.

In some examples, the LV processor may be a multi-core processor with a first core configured to handle sensor data acquisition from various sensors and a second core configured to perform ECG monitoring to detect arrhythmias, control the user interface, control the treatment sequencing, provide data storage, and/or manage data storage. In these examples, the first core of the LV processor may be a digital signal processor core and the second core may be a general purpose processor core including, for example, an ARM core.

As noted above, the LV processor and the HV processor may have a shared memory to share information. For example, the LV processor may store at least a portion of the data from the sensor systems 306 in the shared memory for the HV processor to access. It is appreciated that other processor arrangements 310 may be employed. For example, multiple distinct single core processors may be employed and/or a single multi-core processor including any number of cores.

The communication systems 314 may include various systems to communicate with external devices including, for example, a central server and/or a remote base station. An example base station in addition to various remote devices that may be in communication with the wearable medical device are described in U.S. Patent Publication No. 2012/0112903 titled "REMOTE MEDICAL DEVICE ALARM," published on May 10, 2012 (hereinafter the "'903 Publication"), which is hereby incorporated herein by references in its entirety. The communication systems 314 may include, for example, transmitters, receivers, transceivers, and or antennas to wirelessly communicate. With respect to wireless communication, wireless communication links may be implemented through any one or combination of wireless communication standards and protocols including, for example, BLUETOOTH®, Wireless USB, ZigBee, and Wireless Ethernet.

Example Module Configurations

As described above, the components of the wearable medical device may be organized into a plurality of LV systems 302 and/or HV systems 304. The various components in the LV systems 302 and/or the HV systems 304 may be packaged into a plurality of LV modules and/or HV modules. The plurality of LV modules and/or HV modules may be separate and distinct modules. At least two of the plurality of modules may be electrically coupled by conductive thread, wiring, or cables integrated in to the garment. At least one user interface may be communicatively coupled to at least one of the modules or modular components. The modules may be distributed about the garment to provide an even weight distribution. These modules may be created by, for example, mounting one or more components to a printed circuit board (PCB) or other substrate and housing the PCB in an enclosure.

In some implementations, the plurality of module or modular components comprises low-voltage circuitry disposed within at least one low-voltage module or modular component and high-voltage circuitry disposed within at least one high-voltage module or modular component that is separate and distinct from the at least one low-voltage module or modular component. The low-voltage circuitry may be configured to control at least one of user interactions, cardiac signal acquisition and monitoring, cardiac arrhythmia detection, synchronization of defibrillation pulses with cardiac signals, treatment sequence, patient alerts, data communications, and data storage. The high-voltage circuitry may comprise at least one of the therapy control circuitry and the energy storage devices.

Figure 4A:
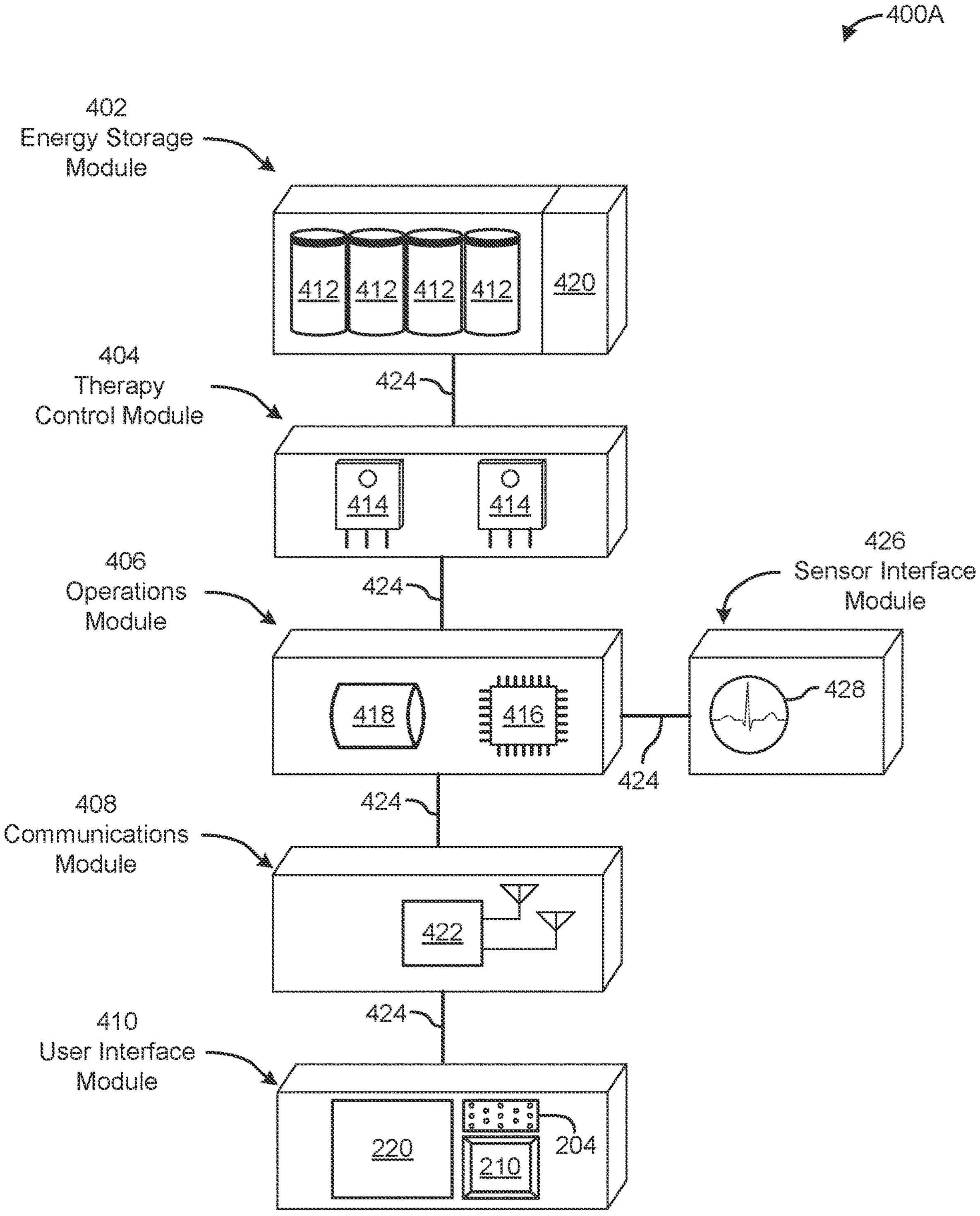
FIGS. 4A-4C show example sets of modules for a wearable medical device.

FIG. 4A illustrates an example set of modules 400A including LV modules and HV modules. As illustrated, the set of modules 400A includes an energy storage module 402, a sensor interface module 426, a therapy control module 404, an operations module 406, a communications module 408, and a user interface module 410. The set of modules 400A may be operably coupled by links 424. The links 424 may include, for example, communication over a BAN, wireless communication links, fiber optics, cables, and/or conductive thread woven into the garment. The links 424 may be wire or conductive thread woven into the garment, and may be flexible or stretchable, or configured in a pattern, for example, a coiled arrangement or a zig-zag pattern that allows the links to stretch with a portion of the garment in which they are integrated or attached to. The links 424 may be capable of supporting communication, power transfer, or both. In examples in which the links 424 are conductive thread, wires, or cables, different ones of the links 424 may be differently sized, for example, having a different thickness, diameter, or cross-sectional area than other of the links 424. The cross sectional area of the different links 424 may be selected based on a voltage, current, or power that the different links are configured to transmit. Links 424 configured to transfer higher amounts of power, for example, links 424 to the therapy electrodes 114 may have larger cross sectional areas than links 424 to the sensing electrodes 112. For example, the cross sectional area or gauge of the links 424 may be selected based on the maximum current ratings as indicated in the following table:

TABLE 1

| Link gauge v. maximum current rating | | |
|---|---|---|
| Link Gauge | Link Diameter (mm) | Maximum current Rating (amps) |
| 40 | 0.079 | 0.014 |
| 35 | 0.142 | 0.044 |
| 30 | 0.254 | 0.142 |
| 25 | 0.455 | 0.457 |
| 20 | 0.813 | 1.5 |
| 15 | 1.45 | 4.7 |
| 10 | 2.59 | 15 |
| 5 | 4.62 | 47 |

Table 1 assumes conductive wires/threads formed of single strands of copper. If conductive wires/threads of other materials or with a different number of strands are used, different maximum current ratings may apply to different gauges.

A conductive wire integrated into the garment and configured to deliver one or more therapeutic pulses to the patient (e.g., via one or more therapy electrodes) can be selected based on a maximum current to be carried in the wire for a transient duration of the current. For example, assuming a therapy pulse in a range of about 1200 V to about 1800 V, a typical maximum current through the conductive wire can be between 60-80 A for a transient duration of about 5-50 ms. The transient duration for determining an appropriate gauge of the conductive wire can be, e.g., less than 10 ms, less than 20 ms, less than 30 ms, less than 50 ms, and less than 100 ms. For example, gauges of between 15 and 35 can meet these requirements. As an illustration, a 28 gauge wire can be used to support a transient duration current in a range of 60-80 A. In some implementations, the various modules may be disposed in the garment. For example, the modules may be constructed to be a permanent part or portion of the garment. For instance, the modules may be permanently disposed within or coupled to the garment. The various modules may be separate and distinct modules wherein one or more of the separate and distinct modules is permanently secured into the garment. In other examples, the modules may be constructed to be removably secured to the garment. The various modules may be separate and distinct modules wherein one or more of the separate and distinct modules is configured to be removably secured into the garment or movably, for example, slidably secured to the garment. For example, the operations module 406 may be permanently coupled into the garment and the therapy control module 404 may be removably secured by conductive hook-and-loop fasteners to the garment. It is appreciated that one or more of the modules may be separate from the garment portion of the wearable medical device. For example, the user interface module 410 may be implemented as a wrist-mounted device (e.g., similar to a watch) as described in the '903 publication.

The energy storage module 402 may store energy for therapeutic pulses including, for example, defibrillation pulses, pacing pulses, and/or TENS pulses. The energy for these pulses may be stored in energy storage devices, for example, capacitors 412 for rapid discharge to a patient. The energy storage devices may comprise a plurality of capacitors and at least one battery, for example, a non-rechargeable battery to provide power to the plurality of capacitors. The energy storage devices may be configured to store energy for at least one therapeutic pulse. The energy storage devices may be coupled to therapy control circuitry in, for example, the therapy control module 404 that is configured to control at least a discharge of energy from the energy storage module. In some examples, the energy storage module 402 may be an HV module due to the charging voltage of the capacitors. The energy storage devices may be disposed in modules or modular components. The energy storage devices may include a first energy storage device to store energy for a first portion of a therapeutic pulse and a second energy storage device, distinct from the first energy storage device, to store energy for a second portion of the therapeutic pulse. The plurality of modules or modular components of the wearable cardiac monitoring device may include a first energy storage device integrated into a front portion of the garment and a second energy storage device integrated into a rear portion of the garment and/or a plurality of capacitors distributed about and integrated into the garment. The energy storage module may be divided into a plurality of separate and distinct capacitor modules or modular components. Each capacitor module or modular component may comprise a capacitor having a form factor adapted to be housed within a corresponding enclosure adapted to conform to a predetermined portion of a patient's body. Each capacitor module or modular component may be coupled to at least one therapy electrode and at least one charger circuit to charge the plurality of capacitors. In some implementations, a single capacitor may be included in one or more distinct and separate capacitor modules or modular components and may be electrically connected with other capacitor modules or modular components.

In some implementations, a plurality of separate and distinct modules or modular components of the wearable cardiac monitoring device may include at least therapy control circuitry and energy storage devices disposed within at least one treatment module or modular component. The at least one treatment module or modular component may be configured to be removably secured to the garment and to provide treatment to the patient based on a detected cardiac condition of the patient.

In some examples, the energy storage module 402 may include a battery 420 to charge the capacitors. Locating the battery 420 proximate the capacitors 412 and/or charging circuit for the capacitors 412 may be advantageous because it reduces the distance that the charging current from the battery needs to travel to reach the capacitors. Similarly, the therapeutic pads (e.g., therapy pads 114) may be coupled to the energy storage module 402 to minimize the distance that the energy must travel from the capacitors to the therapeutic pads. For example, the links coupling the capacitors to the therapeutic pads may be capable of withstanding 1,600 volts and a 15,000 volt electrostatic discharge (ESD). Thereby, electrical pathways that need to support the large charging current and/or discharge energy may be avoided or at least minimized in length. The energy storage module 402 may be separate and distinct from other modules of the wearable cardiac device and may be coupled to at least one therapy electrode and may be configured to store energy for at least one therapeutic shock to be applied to the patient.

In some examples, the battery 420 is a non-rechargeable battery. Making the battery 420 a non-rechargeable battery may be advantageous in some examples for multiple reasons. For example, non-rechargeable batteries generally have a greater energy density than rechargeable batteries allowing a lighter battery to be employed and, thereby, reducing the weight of the wearable medical device. Employing non-rechargeable batteries may have other advantages including a battery capacity that does not fade over time as the battery experiences more charge and discharge cycles, and/or an internal impedance that does not increase as the battery experiences more charge and discharge cycles. The increased internal impedance and/or the diminished capacity of older rechargeable batteries may render the rechargeable battery incapable of providing a sufficient amount of energy to charge the capacitors and provide therapy to the patient.

It is appreciated that, in some examples, the battery 420 is a rechargeable battery. The disadvantages of the rechargeable batteries discussed above may be mitigated by, for example, introducing a battery test sequence that tests a condition of the battery. The battery test may include an impedance test to determine whether the internal impedance of the battery has exceeded a threshold. If the internal impedance of the battery has exceeded the threshold, the wearable medical device may issue an alert to the user via the user interface to notify the user that the rechargeable battery should be changed.

At least one of the modules or modular components of the wearable cardiac monitoring device may removably couple to the rechargeable battery 420 or to a different rechargeable battery. The garment may removably couple to the rechargeable battery 420 or to a different rechargeable battery for powering one or more of the modules or modular components.

In some examples, the wearable medical device monitors a state of charge (SoC) of the battery 420. The wearable medical device may, for example, issue a notification when the SoC transgresses a minimum threshold to swap out the battery 420 and/or seek service for the wearable medical device. The SoC of the battery 420 may be monitored by, for example, monitoring the number of shocks and/or the amount of energy applied to the patient in therapeutic pulses and/or monitoring a voltage of the battery.

The sensor interface module 426 (e.g., similar to sensor systems 306) can, for example, include circuitry to sense various physiological parameters of the patient via one or more sensors 428. The sensors 428 of the sensor interface module 426 may include, for example, ECG electrodes to monitor an ECG of the patient, acoustic sensors to monitor the heart and/or lung sounds of the patient, respiration monitors to monitor the respiration of the patient, such as during a sleep study or when monitoring for sleep apnea, and/or radio-frequency based fluid monitoring sensors. The sensors 428 may further include one or more sensors configured to monitor one or more of patient activity, patient motion, tissue fluids, lung fluid, blood oxygen levels, or blood pressure of the patient. Each of the ECG sensor circuitry, the acoustic sensor circuitry, the respiration sensor circuitry, and the radio-frequency circuitry can be disposed within separate and distinct modules or modular components that are physically set apart from one another and, e.g., distributed about the garment for even weight distribution. Each of the modules can include one or more memory buffers to store the sensed raw data locally or include communications circuitry, e.g., a low-power radio frequency transmitter, for wirelessly communicating the raw sensed data to another module (e.g., the operations module) or to a remote location for further processing. For example, the operations module or operations modular component may be separate and distinct from other modules of the wearable cardiac device and may be coupled to at least one sensing electrode configured to monitor cardiac activity of the patient and may be configured to detect at least one cardiac condition of the patient. Communications circuitry may be disposed within a communications module or modular component that is separate and distinct from the operations module or modular component and the energy storage devices and may be coupled to at least one of the operations module or modular component and the energy storage devices and may be configured to communicate with at least one external device. Each of the modules can include one or more processors for deriving one or more metrics from the raw sensed data prior to storing or transmitting the data. For example, a local ECG processor within the ECG sensor module may process the raw ECG data to derive heart rate information and transmit the heart rate information to another location.

The ECG sensor circuitry can be disposed within a module comprising ECG processing and communications circuitry, such as, amplifiers to amplify a received ECG signal from one or more ECG sensors, filters, analog-to-digital converts, and one or more processors configured to receive the ECG signals and detect one or more ECG metrics from the received ECG signal. For example, such detected ECG metrics can include the QRS waveform, P and T waveforms, and further ECG metrics such as heart rate, heart rate variability, atrial fibrillation, and other cardiac arrhythmias, among others.

The acoustic sensor circuitry can be disposed within a module comprising an acoustic sensor and associated processing and communications circuitry, such as, amplifiers to amplify the heart sounds signals from one or more acoustic sensors (e.g., microphones), filters, analog-to-digital converts, and one or more processors configured to receive the heart sounds signals and detect one or more heart sounds metrics from the received heart sounds signal. For example, such detected heart sounds metrics can include S1, S2, S3, and S4 sounds, as well as further heart sound metrics. Such derived heart sound metrics can be based on heart sounds alone or a combination of heart sounds and ECG information such as electromechanical activation time (EMAT), e.g., a systolic time interval from a QRS-wave onset to a peak of the first heart sound (S1), and left ventricular systolic time (LVST), e.g., a systolic time from the peak of the first heart sound (S1) to the peak of the second heart sound (S1), making the end of the systole phase.

The respiration sensor circuitry can be disposed within a module comprising a respiration sensor and associated processing and communications circuitry. For example, the respiration sensor can include an accelerometer disposed within the garment and positioned at a predetermined location on the patient's torso. For example, one or more accelerometers can be positioned about the patient's thorax or chest and the respiration rate and associated data can be estimated using digital signal processing circuitry. For example, the accelerometer can include an ADXL204 biaxial accelerometer (+/−1/7 g type), having a sensitivity of around 620 mV/g. For example, the accelerometer can be located in the sagittal plane, and on the left side of the anterior portion of the patient's torso. The patient's breathing can cause a periodical movement of the patient's thorax and thus changes an inclination and/or displacement of the accelerometer placed on the patient's chest in the horizontal and vertical directions. For example, a breathing signal may be detected along a direction perpendicular to the direction of gravity as a most sensitive direction for measuring thorax movement. Accordingly, the processing circuitry associated with the respiration sensor can be configured to process signals in the sagittal place.

In some examples, the respiration sensor can include ECG sensing electrodes and an associated circuitry that can extract, e.g., a patient's respiration rate based on signal amplitude changes in body surface potential differences between two electrodes disposed on the patient's torso. For example, the electrodes can be configured to pick up changes in the transthoracic impedance as the lungs of the patient fill and empty during a breathing cycle. In another method of measurement, beat to beat variations in the duration of the RR intervals can be recorded as being correlated to respiration.

In various examples, the respiration sensor can implement other respiration monitoring techniques. For example, the sensor can be based on devices that measure motion, volume, or tissue changes (e.g., trans-thoracic impedance techniques, rib inductance plethysmography), devices that measure airflow (e.g., thermistors for measurement of oro-nasal airflow) that can be removably secured to an attachment point (e.g., via hook and loop fasteners, snap fasteners, or pockets) on the garment and used by the patient to measure respiration data, and devices that measure blood gas changes, such as, pulse oximetry or end-todal $O_2$ changes. Respiration data can include estimates of respiratory rate, and quantitative information about tidal volume, and gas exchange parameters.

The radio-frequency (RF) circuitry for detecting tissue fluid changes can include an RF sensor and associated circuitry for transmitting ultra-wide band RF signals to an underlying tissue, e.g., a portion of the patient's lung, and receive reflected RF signals, and processing one or more of a change in an amplitude and phase of the RF signals.

The sensor interface module 426 may include various sensor acquisition circuits to, for example, filter and/or pretreat the sensor signals prior to providing the sensor signals for analysis to identify one or more patient conditions as described in U.S. Pat. No. 8,600,486 titled "METHOD OF DETECTING SIGNAL CLIPPING IN A WEARABLE AMBULATORY MEDICAL DEVICE," issued on Dec. 3, 2013 (hereinafter the "'486 patent"), which is hereby incorporated herein by reference in its entirety. In some examples, the sensor signals can be provided to one or more processors in the operations module 406 (described below). For example, the sensor interface module 426 may include a cardiac monitoring module that receives ECG and/or heart sounds data and performs analysis on the data to determine the existence of one or more cardiac conditions. For example, based on ECG signals and/or the heart sounds data, the cardiac monitoring module may detect one or more cardiac arrhythmias and alert the patient via the user interface module 410. In at least one example, the sensor interface module 426 is a LV module and only includes LV components.

It is appreciated that one or more functions of the sensor interface module 426 may be included as functions of the operations module 406. For example, the circuitry to pretreat the sensor signals may be included in the circuitry for the operations module 406 and the sensors 428 may be directly coupled to the operations module 406.

The therapy control module 404 controls the delivery of therapeutic pulses to the patient from energy stored in, for example, one or more capacitors 412 of the energy storage module 402. For example, the therapy control module 404 may control various characteristics of the therapeutic pulses including, for example, the magnitude, shape, and/or duration of the therapeutic pulses provided to the patient. The characteristic of the pulses may be controlled by various power control devices including, for example, by insulated-gate bipolar transistors (IGBTs) 414. It is appreciated that other types of power control devices may be employed (e.g., a silicon controlled rectifiers, thyristors, etc.) and any number of power control devices may be employed. In some examples, the therapy control module 404 may be an HV module due to the high voltage controlled by, for example, the IGBTs. In at least one example, the battery 420 and/or therapeutic pads 114 may be coupled to the therapy control module 404. As discussed above, it may be advantageous to locate the battery 420 proximate the capacitor charging circuitry (e.g., circuitry in therapy control module 404) to reduce the distance that the charging current needs to travel from the battery 420 to the capacitors 412 and/or the distance the discharging current needs to travel from the capacitors 412 to the therapy pads 114. In some implementations, the components of the therapy control module 404 may be powered by the therapy control module's own battery power source that is separate from the battery 420.

The operations module 406 includes devices to control the operation of the medical device. For example, the operations module 406 may include one or more processors 416 coupled to a data storage element 418 to monitor sensed cardiac data, identify cardiac arrhythmias based on the cardiac data, initiate the delivery of conductive gel to the patient's skin via the gel deployment circuitry, and/or direct the administration of treatment to the patient. The sensing systems may be coupled to the operations modules 406 to provide the processors 416 direct access to the sensor data. In at least one example, the operations module 406 may be an LV module and only includes LV components. The operations module 406 may comprise at least one processor disposed in an operations module or modular component separate from other modules or modular components to monitor the cardiac data received from at least one electrode and communicate with therapy control circuitry to direct administration of treatment to the patient.

In some examples, the processor 416 may include one or more processors from the processor arrangement 310 described above with reference to FIG. 3. For example, the general purpose processor from the processor arrangement 310 may be housed in the operations module 406. The high-voltage processor in the processor arrangement 310 may be housed in, for example, the operations module 406 or the therapy control module 404.

The communications module 408 may include communication circuitry 422 to enable the wearable medical device to communicate with external systems. For example, the communications module 408 may employ one of a variety of methods to communicate with a base station and/or external systems including, for example, BLUETOOTH®, Wireless USB, ZigBee, and Wireless Ethernet. In at least one example, the communications module 408 is a LV module and only includes LV components. The communications module 408 may comprise communications circuitry disposed in a communications module or modular component separate from other modules or modular components and configured to communicate with at least one external system.

The user interface module 410 may enable the wearable medical device to communicate with external entities including, for example, a patient, a physician, an emergency responder, a bystander, and/or a caregiver of the patient. For example, the user interface module 410 may emit alarms to notify the patient of various medical conditions as described in U.S. Pat. No. 9,135,398 titled "SYSTEM AND METHOD FOR ADAPTING ALARMS IN A WEARABLE MEDICAL DEVICE," issued on Sep. 15, 2015 (hereinafter the "'398 patent"), which is hereby incorporated herein by reference in its entirety. The user interface module 410 may include one or more of the user interface elements described above with regard to the wearable medical device 100 including, for example, the display 220, the speaker 204, and/or the response button (or a plurality of buttons such as two response buttons to be held down together) 210. In some implementations, the application of treatment to the patient may be delayed responsive to detecting multiple response buttons 210 being depressed simultaneously and/or to detecting one response button 210 being depressed in a particular sequence as described in U.S. Patent Publication No. 2015/0039053, titled "SYSTEMS AND METHODS OF DELIVERYING THERAPY USING AN AMBULATORY MEDICAL DEVICE," published on Feb. 5, 2015 (hereinafter the "'053 publication"), which is hereby incorporated herein by reference in its entirety. In at least one example, the user interface module 410 is an LV module and only includes LV components.

The user interface module 410 may be implemented in any of a variety of form factors. For example, in some examples, the user interface module 410 may be implemented as a computer-enabled watch with display 220 and/or speaker 204 to provide visual and/or audible notifications to the user. The display 220 may be a touch-screen display to more easily allow an external entity to navigate the user interface. It is appreciated that other devices may be included in the computer-enabled watch, or any other implementation of the user interface module 410, to communicate with external entities including, for example, a tactile vibrator. The computer-enabled watch may further include a response button 210 mounted, for example, on a side of the computer-enabled watch, or elsewhere, to delay the administration of treatment. The computer-enabled watch may wirelessly communicate with one or more modules of the set of modules 400A and receive power from a rechargeable battery built into the computer-enabled watch. In some examples, the watch may include an adjustable strap to secure the computer-enabled watch to a wrist of the patient. In other examples, the watch may include a larger strap to secure the device to a bicep of the patient. The larger strap may be an elastic strap to flex to account for bicep contractions as the patient moves about during daily activity.

The user interface module 410 may also be implemented as an application on a computer-enabled portable electronic device including, for example, smart phones, smart watches, personal digital assistants, and tablet computers. For example, the portable electronic device may be in communication with one or more modules of the set of modules 400A by various wireless communication methods including, for example, BLUETOOTH®. The application on the portable electronic device may leverage the existing hardware on the portable electronic device to operate as the various user interface elements. For example, the application may display a virtual response button 210 on a touch screen of the portable electronic device that the user can activate by touching the touch screen at the appropriate location. In some examples, the touch screen may identify whether the person touching the screen is the patient associated with the device, or another, by fingerprint analysis, voice analysis, or other analyses.

In some implementations, one or more of the functions of the operations module 406 may be included among the functions of the user interface module 410. For example, the user interface module 410 may be implemented as a computer-enabled wearable device and/or as an application on a computer-enabled portable electronic device as described above. In this example, the user interface module 410 may leverage the processing capabilities of the computer-enabled device to receive the sensor data from the sensor interface module 426 and monitor the medical condition of the patient. Thereby, the size, weight, and/or bulkiness of the operations module 406 in the garment may be reduced and/or eliminated.

The operations module 406, the communications module 408, and/or the user interface module 410 may receive power from the battery 420 and/or from an additional battery (not illustrated). For example, the operations module 406, the communications module 408, and/or the user interface module 410 may removably couple to one or more rechargeable batteries. In some examples, these rechargeable batteries may be swapped out periodically by the patient and/or charged by various energy sources, for example, a renewable energy source. For example, the operations module 406 may include a solar panel affixed to an external surface of the module to generate power for charging the rechargeable battery. The garment may also be employed to harvest solar energy for charging the rechargeable battery by integrating solar fabric into the garment. In other examples, piezoelectric elements may be incorporated in to the garment to transform energy from movement of the patient into electrical energy.

Figure 4B:
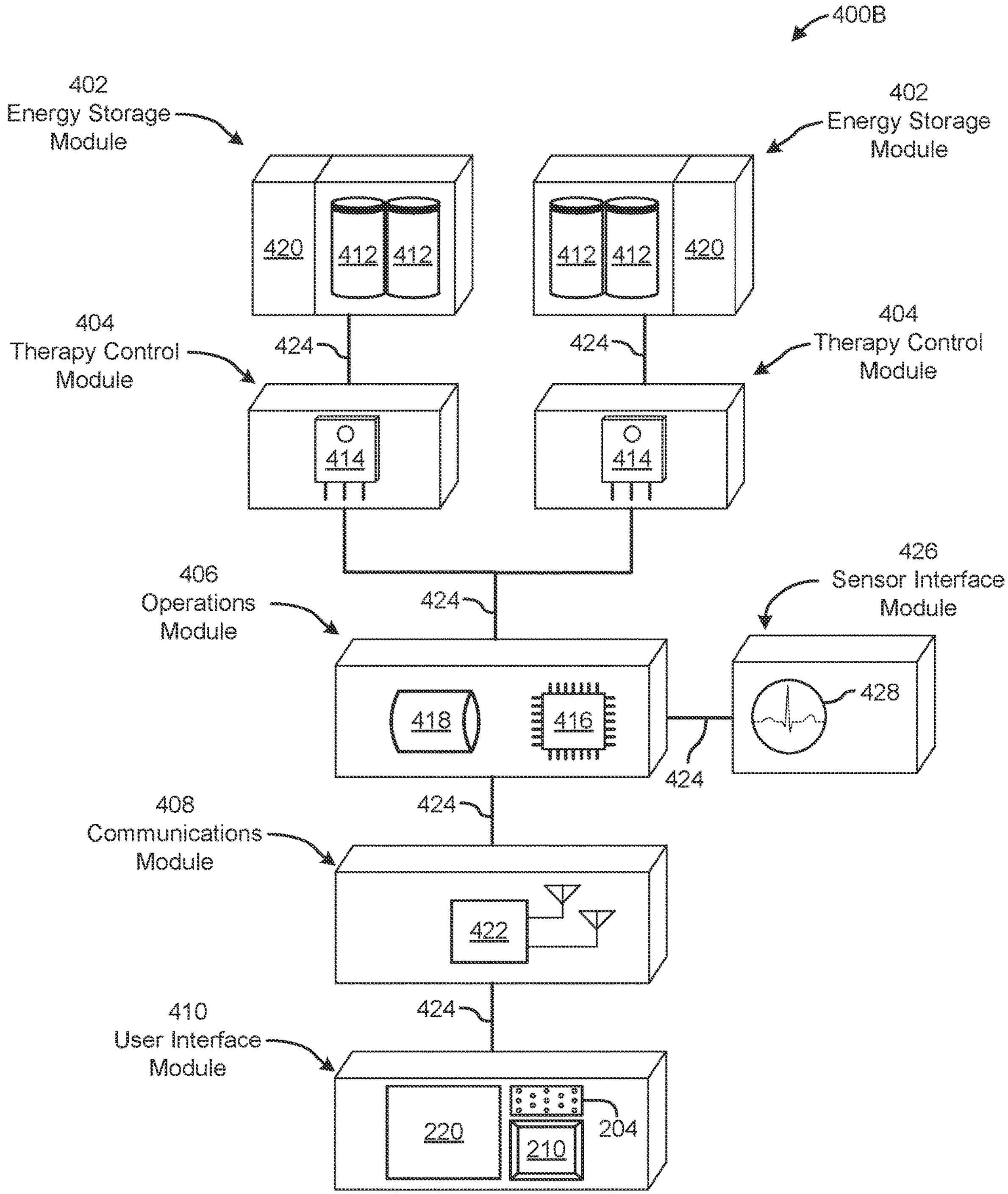

FIG. 4B illustrates another set of modules 400B including the operations module 406, the communication module 408, and the user interface module 410 in addition to two energy storage modules 402 and two therapy control modules 404. In some examples, each energy storage module 402 and therapy control module 404 pair provides a portion of the therapeutic pulses. For example, the wearable medical device may be configured to provide bi-phasic defibrillation pulses to the patient. In this example, the first energy storage module and therapy control module pair may provide the energy for the first phase of the pulse and the second energy storage module and therapy control module pair may provide the energy for the second phase of the pulse. In another implementation, the first energy storage module and therapy control module pair may provide the energy for a first pulse and the second energy storage module and therapy control module pair may provide the energy for a second pulse. Along these lines, the delivery of subsequent pulses may be shared between the pairs in a predetermined arrangement. For instance, such an arrangement may be that the two pairs alternate in energy delivery until the pulses are no longer needed. In another implementation, the first energy storage module and therapy control module pair may provide the energy for a positive portion of a pulse waveform and the second energy storage module and therapy control module pair may provide the energy for a negative portion of the pulse waveform. In some examples, a controller coupled to the two pairs may intelligently control the pulse characteristics and energy delivery from the two pairs. Dividing the energy storage and therapy control modules as illustrated may balance the weight distribution of the wearable medical device. For example, each of the energy storage modules 402 illustrated in FIG. 4B may be smaller in size and lighter than the single energy storage module 402 in FIG. 4A. Further, these smaller lighter modules may be spaced apart on the garment to improve weight distribution.

It is appreciated that any module described herein (e.g., the energy storage module 402) may be divided into a plurality modules and/or sub-modules. For example, the set of modules may include an energy storage module 402 for each therapy pad. Similarly, the therapy control modules 404 may be divided into any number of modules. For example, the two therapy control modules 404 illustrated in FIG. 4B may be combined into a single therapy control module 404 that is coupled to both energy storage modules 402.

Figure 4C:
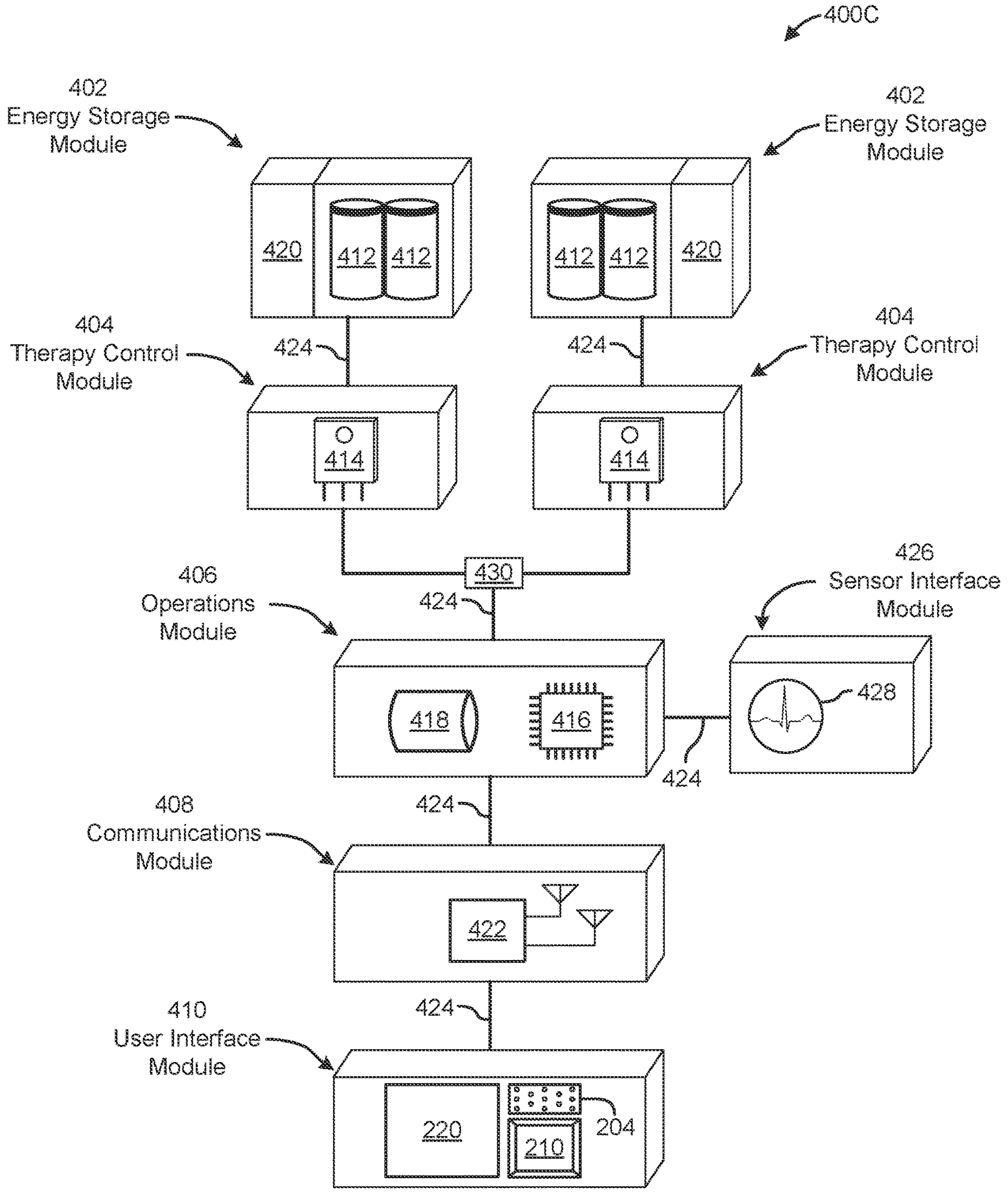

In some examples, the therapy delivery systems may be separable from the monitoring systems. For example, the wearable medical device may operate as a medical monitoring device when the therapy delivery systems are not installed in the wearable medical device. Making the therapy delivery systems separable from the monitoring systems may, in some examples, advantageously reduce the weight of the wearable medical device for patients that do not need the treatment components (e.g., modules 402 and 404) or that do not have a current need for them. FIG. 4C illustrates another example set of modules 400C with separable treatment components. As illustrated in FIG. 4C, the energy storage modules 402 and the therapy control modules 404 are separable from the remaining modules by a connection element 430 (e.g., an electrical connector). Thereby, the patient can disconnect the energy storage modules 402 and/or the therapy control modules 404 and remove the modules from the assembly 400C. The wearable medical device may further automatically detect the installation of the therapy delivery systems and operate as a wearable treatment device and may similarly detect the separation from the therapy delivery systems and operate as a wearable monitoring device. Responsive to detecting the installation of the therapy delivery systems, the wearable medical device may initiate and perform a self-test to check, for example, that the therapy delivery systems have been properly attached and electrically or otherwise coupled to other portions of the wearable medical device and/or to check that the components of the therapy delivery systems are in working order, for example, that conductive gel in conductive gel deployment modules has not reached its expiration date, that the battery or batteries included in components of the wearable medical device have sufficient charge, etc.

It is appreciated that the treatment components may be separable by other mechanisms separate and apart from the connection element 430. For example, the links 424 coupling the operations module 406 to the therapy control modules 404 may be wireless communication links. In this example, the wearable medical device may configure itself as a wearable treatment device when modules 404 and 402 are within range of the operations module 406 for wireless communication. Thereby, the patient can configure the wearable medical device as a treatment device by attaching the treatment components to the garment and, conversely, configure the wearable medical device as a monitoring device by detaching the treatment components from the garment. In some implementations, the user interface may prompt the patient to confirm whether the wearable medical device is to be configured as a treatment device or as a monitoring device responsive to the detected proximity or lack of proximity of the modules 404/402 and 406. It is appreciated that the treatment components (e.g., modules 402 and 404) may be wired together as a single assembly that can be removed or added to the garment as a single unit.

In some implementations, the operations module 406 may receive signals from one or more patient monitor detectors, accelerometers and/or sensors indicative of patient activity. In addition to receiving input from the patient (e.g., via the response buttons) or to correlate such input, one or more processors in the operations module 406 may analyze such signals for patient activity and determine based on the signals whether treatment is appropriate. For instance, if the patient is unconscious, signals from one or more patient monitor detectors, accelerometers and/or sensors may indicate that there is no patient activity. The operations module 406 may cause the treatment sequence to proceed, culminating in the delivery of treatment to the body of the patient. The one or more motion detectors, accelerometers, and/or sensors may be included in a separate module or subsystem or disposed within one or more of the other modules or subsystems described herein. For example, motion detectors, accelerometers, and/or sensors for use in the present application may include those described in U.S. Pat. No. 7,974,689, titled "WEARABLE MEDICAL TREATMENT DEVICE WITH MOTION/POSITION DETECTION," issued on Jun. 5, 2011, which is hereby incorporated herein by reference in its entirety.

In some implementations, the operations module 406 may also receive signals indicative of audio input from the patient in determining whether to suspend treatment to the patient. For example, such audio input may include one or more sounds, such as one or more spoken words or phrases, made by the patient that the operations modules 406 is configured to recognize. Example implementation of such audio input elements are described in U.S. Pat. No. 8,369,944, titled "WEARABLE DEFIBRILLATOR WITH AUDIO INPUT/OUTPUT," issued on Feb. 5, 2013 (hereinafter the "'944 patent"), which is hereby incorporated herein by reference in its entirety. A microphone for receiving the patient's audio input may be disposed on one or more of the garment, a housing of the communications module 408, or a housing of any of the other modules. In some implementations, the microphone may be disposed in the garment, e.g., substantially proximate to the patient's upper body. In some implementations, the microphone maybe integrated into a shoulder or anterior portion of the garment and electrically coupled, e.g., coupled using conductive threads, wires, or cables embedded in the garment, or wirelessly connected (e.g., using BLUETOOTH® technology) to the operations module 406.

Example Integrated Garments with One or More Removably Attached Modules

Dividing the various components of the wearable medical device into a module assembly as illustrated by FIGS. 4A-4C enables the weight of, for example, the medical device controller to be distributed about the garment. The modules may be distributed about the garment so as to evenly distribute the weight of the garment. For example, the weight of a left side of the garment may be equal (or substantially equal) to the weight of the right side of the garment to provide an even distribution of weight on the shoulders of the patient.

Figure 5A:
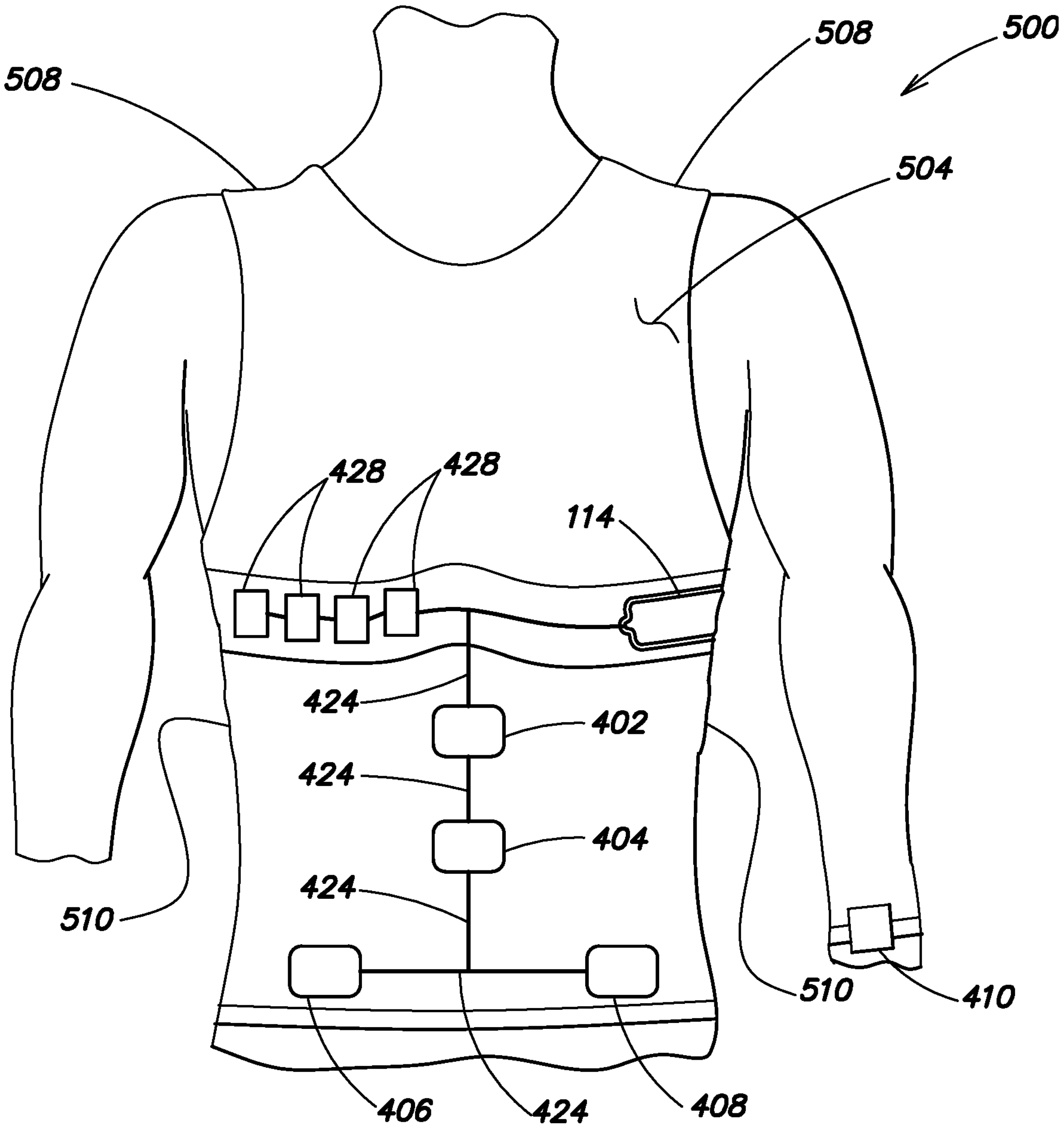
FIGS. 5A and 5B show an example garment for a wearable medical device with a module assembly.
Figure 5B:
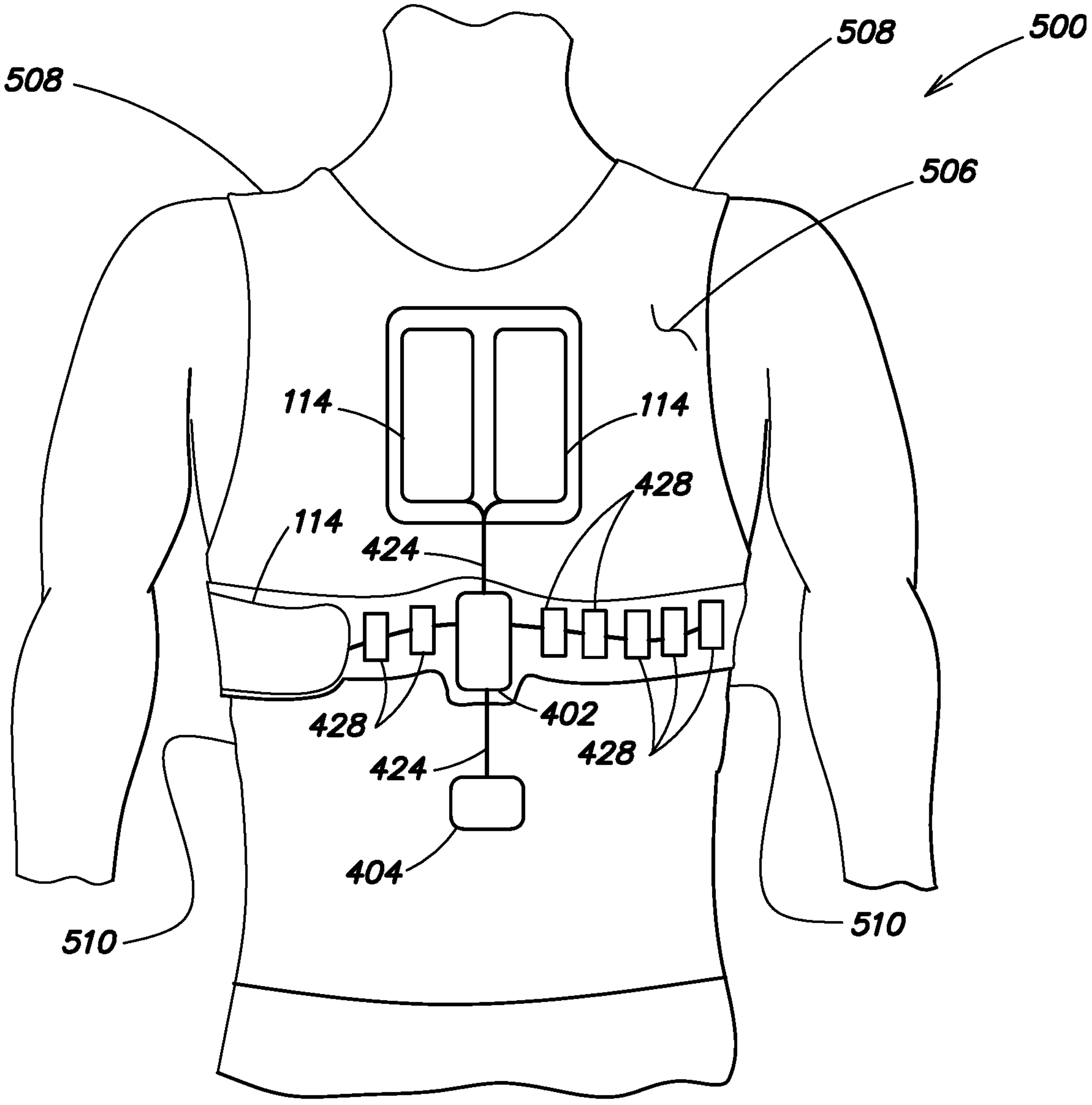

FIGS. 5A and 5B illustrate an example garment 500 with a set of modules 400B from FIG. 4B distributed about the garment 500. The garment 500 includes a front portion 504 and a rear portion 506 that cover both an upper portion of the torso and a lower portion of the torso of the patient. As shown, the garment 500 includes shoulder portions 508 and side portions 510 that connect the front portion 504 to the rear portion 506 of the garment 110. The side portions 510 may extend from under the arms to near the waist line (e.g., to the bottom of the torso) in a similar fashion to a vest or a T-shirt. The shoulder portions 508 may be narrow strips of fabric constructed in a similar fashion to shoulder portions of vests. For example, the garment may be comprised of stretchable, anti-microbial, breathable, and/or moisture-wicking fabric.

In one example, the shoulder portions or other portions of the garment may include an expansion mechanism configured to shorten or lengthen the straps and/or other portions of the garment. In one example implementation, the shoulder portions or other portions of the garment may include one or more adjustable buckle straps. The adjustable buckle strap may include a first and a second end, two substantially non-elastic portions, and a substantially short elastic portion. The substantially short elastic portion may be located between the two substantially non-elastic portions and provide lengthwise expansion to the strap up to a predetermined limit. The buckle can be attached to the first end of the strap to secure a portion of the strap adjacent to the second end of the strap.

The garment 500 includes a plurality of sensors 428 that may be permanently disposed in the garment and/or removably coupled to the garment. In some examples, the sensors 428 are ECG sensors that are constructed from conductive thread and/or metallic surfaces sewn into the garment as discussed in U.S. Pat. No. 9,008,801, titled "WEARABLE THERAPEUTIC DEVICE," issued on Apr. 14, 2015 (hereinafter the "'801 Patent"), which is hereby incorporated herein by reference in its entirety. Similarly, the therapy pad 114 may be permanently and/or removably coupled to the garment. For example, the sensors 428 can be capacitance-based dry sensing electrodes. In one example, the sensors 428 may include ECG sensing electrodes that can be permanently or removably coupled to the garment at predetermined locations and supported by the garment and can include an oxide layer, e.g., a tantalum pentoxide insulating layer or dielectric layer formed on a substrate as described in U.S. Pat. No. 6,253,099, titled "CARDIAC MONITORING ELECTRODE APPARATUS AND METHOD," issued on Jun. 26, 2001 (hereinafter the "'099 patent"), which is hereby incorporated herein by reference is its entirety. In some embodiments, the sensors 428 may be removably secured to the garment at the predetermined locations in one or more conductive mating configurations. For example, the conductive mating configurations can include electrically connected receptacles that are interconnected via conductive threads, wires, or cables woven into the garment and connected to an ECG acquisition module (e.g., part of the sensor interface module 426).

In some implementations, the sensors 428 include ECG sensing electrodes that can be disposed at various predetermined locations including different axial positions around the body of the patient as shown and described in, for example, FIGS. 1A-F of U.S. Pat. No. 8,706,215, titled "WEARABLE AMBULATORY MEDICAL DEVICE WITH MULTIPLE SENSING ELECTRODES," issued on Apr. 22, 2014 (hereinafter the "'215 patent"), which is hereby incorporated herein by reference in its entirety. In some examples, the sensor interface module 426 and/or the operations module 406 may include a multiplexer to control which ECG sensing electrode pairings are being monitored. For example, the sensor interface module 426 and/or the operations module 406 may identify one or more optimal pairings (e.g., the pairings with the best signal quality) and control a state of the multiplexer so as to receive ECG signals from the identified pairing(s). It is appreciated that the electrodes may be multiplexed manually. For example, the garment may include multiple predetermined locations to receive ECG electrodes and a pairing may be selected by only connecting ECG sensing electrodes at a subset of the predetermined locations.

The modules 402, 404, 406, and 408 are distributed about the garment so as to evenly distribute the weight of the medical device on the left shoulder and the right shoulder of the patient. As illustrated, the user interface module 410 is implemented as a computer-enabled watch as previously described. It is appreciated that other implementations of the user interface module 410 may be employed. For example, the user interface may be permanently disposed with or removably attached to the garment and accessible by the patient.

In some examples, one or more of the modules 402, 404, 406, and 408 are removable from the garment. For example, the links 424 may be cables (e.g., conducting cables and/or optical fiber cables) that are attached to each of the modules to form a single removable assembly. The cables may be covered in a jacket to protect the cables from the environment. In these examples, the assembly may be attached to the garment by one or more of hook-and-loop fasteners, snaps, buttons, or by other various techniques.

The locations for each part of the assembly to attach to the garment may be color-coded to help the patient (or physician) attach the assembly to the garment. For example, the communications module 408 may include a red hook-and-loop fastener and the appropriate location to attach the communications module 408 to the garment may also include a red hook-and-loop fastener. To aid in assembly, certain components may include one type of attachment mechanism (e.g., snaps) and others may include a different type (e.g., hook-and-loop fasteners, magnets, or buttons). Thereby, the user of the wearable medical device may be encouraged to attach each module at the correct location. It is appreciated that the assembly may also be a two-piece assembly as discussed above with reference to FIG. 4C that includes a monitoring assembly and a treatment assembly that is separable by, for example, a connection element 430.

It is appreciated that the links 424 between the modules 402, 404, 406, and 408 may not be uniform. For example, the link between the communications module 408 and the user interface module 410 may be a wireless link while the link between the communications module 408 and the operations module 406 may be a wired link (e.g., by a cable). Further, the wired links (if any) between the modules 402, 404, 406, and 408 may not be uniform. For example, the link 424 coupling the energy storage module 402 to the therapy pad 114 may support 1,600 volts and a 15,000 volt ESD while the link 424 between the operations module 406 and the communications module 408 may have a lower voltage and ESD rating. In some examples, one or more of the links 424 may be integrated into the garment. In some examples, one or more of the links 124 may be disposed between two layers of fabric of the garment. For example, the links 424 may be constructed from conductive thread, wires, cables, and/or fiber optical cables integrated into the garment. In these examples, the garment may be configured to receive each of the modules and operably couple the modules to the links 424 integrated into the garment when the modules are attached to the garment. In these examples, a user (e.g., a patient, physician, or caregiver) can configure the wearable medical device for monitoring or treatment based on the modules that are removably coupled to the garment. For example, the wearable medical device may be configured as a wearable monitoring device by not installing the treatment modules. In this example, the treatment functionality of the wearable medical device may be restored by attaching the appropriate treatment modules to the garment.

Figure 6A:
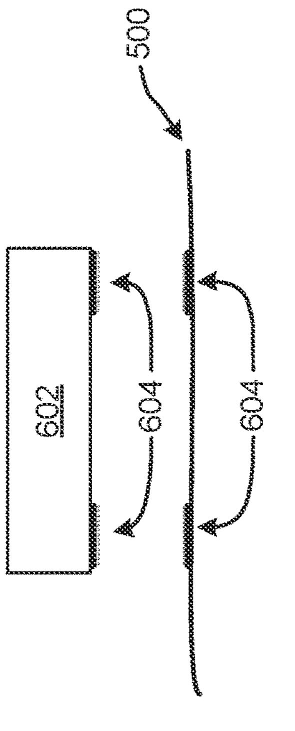
FIGS. 6A-6F show various communication and/or power transfer methods to operably couple a module to a garment for a wearable medical device.

FIGS. 6A-6F illustrate a number of different techniques that may be employed to operably couple modules to one or more links 424 integrated into the garment 500. FIG. 6A, for example, illustrates conductive hook-and-loop fasteners 604 operably coupling the module 602 to the conductive thread in the garment. The conductive hook-and-loop fasteners may be constructed by, for example, employing conductive thread in various portions of the hook-and-loop fasteners. It is appreciated that any number of individual conductive hook-and-loop fasteners 604 may be employed. For example, the number of individual hook-and-loop fasteners for a given module may be equal to the number of channels required between the garment and the module. For example, a module may couple to the garment by four individual conductive hook-and-loop fasteners where the first fastener is used for power, the second fastener is used for ground, and the remaining two fasteners are used for data transfer.

Figure 6B:
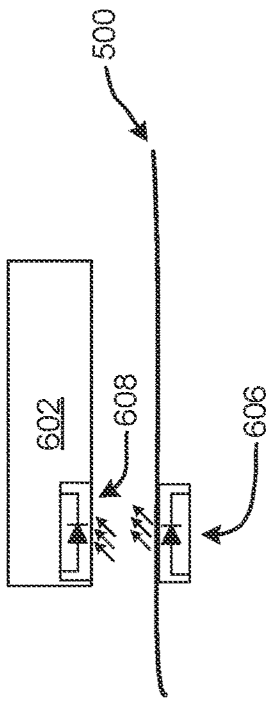

FIG. 6B illustrates an optical coupling between the module and the garment. For example, the garment may include an infrared (IR) transmitter 606 that sends information to an IR receiver 608 in the module and/or vice-versa. The IR transmitter 606 may include, for example, a light-emitting diode capable of emitting light in the IR spectrum that is intermittently pulsed. The IR receiver 608 may include, for example, a photo-sensitive device that detects the IR light pulses from the IR transmitter. It is appreciated that the module 602 may include IR transmitters 606 in addition to IR receivers 608 for bi-directional communication with the garment.

Figure 6C:
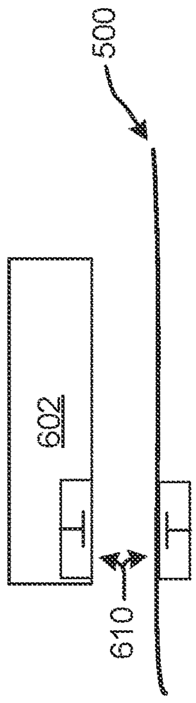
Figure 6D:
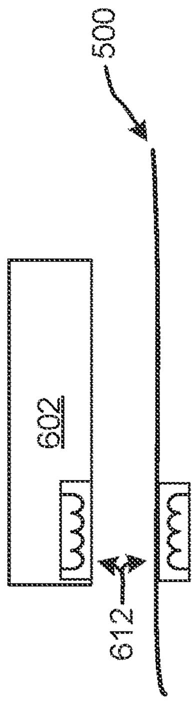
Figure 6E:
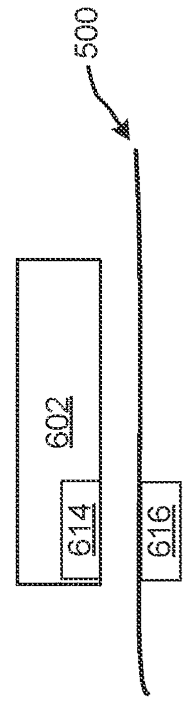
Figure 6F:
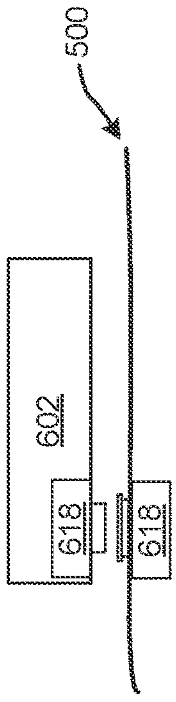

FIGS. 6C and 6D illustrate a capacitive coupling 610 and an inductive coupling 612 between the module 602 and the garment. Other techniques may be employed based on changing electrical and/or magnetic fields to transmit information and/or power. FIG. 6E illustrates a module 602 including a conductive magnet 614 that is attracted to a conductive contact 616. The conductive contact 616 may include at least a portion of a ferrous material including, for example, steel. The conductive magnet 614 may be sufficient to hold the module in place on the garment. FIG. 6F illustrates an example conductive snap 618. The conductive snap 618 may secure the module 602 in place in addition to establishing a connection between the garment 500 and the module 602.

It is appreciated that the modules may use any combination of the above described techniques to operably couple the modules to conductive thread, wiring, or cables, integrated into the garment and/or hold the module in place on the garment. For example, a module may include a steel magnet in addition to one or more IR receivers.

Figure 7A:
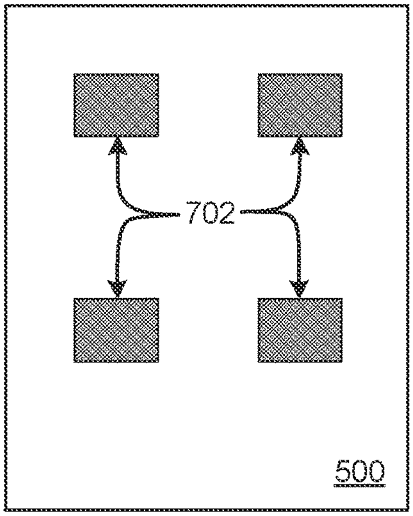
FIGS. 7A-7D show various techniques to removably secure a module to a garment for a wearable medical device.
Figure 7B:
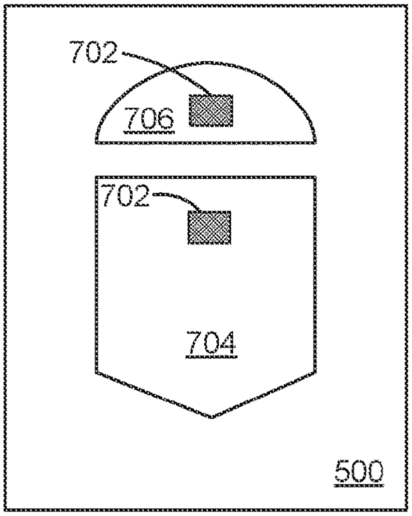
Figure 7C:
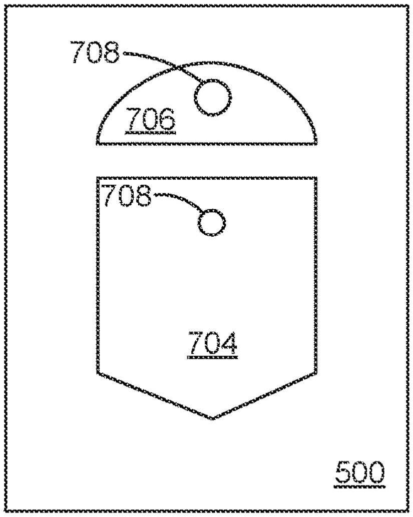
Figure 7D:
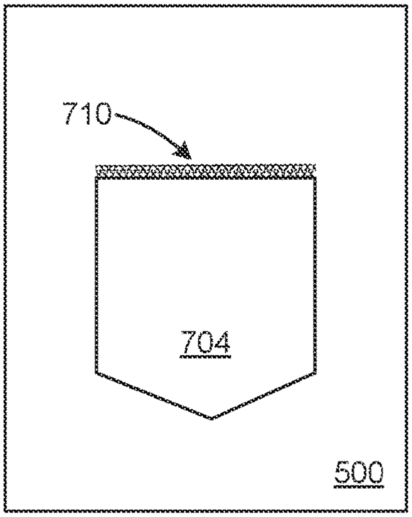

In some examples, the modules may use one or more techniques to hold the modules in place on the garment. FIGS. 7A-7D, for example, illustrate various techniques to removably secure a module to the garment. As shown in FIG. 7A, the module may be secured to the garment 500 by hook-and-loop fasteners 702. FIG. 7B illustrates a pocket 704 to receive the module and a flap 706 that is secured to cover the opening of the pocket 704 by hook-and-loop fasteners 702. FIG. 7C illustrates another example pocket 704 to receive the module with a flap 706 that is secured by a snap fastener 708. FIG. 7D illustrates another example pocket 704 to receive a module that secures the module in place by a zip fastener 710. It is appreciated that the pockets 704 illustrated in FIGS. 7B-7D may include one or more of the communication and/or power transfer devices described above with references to FIGS. 6A-6F including, for example, an IR transmitter.

In some examples, the pockets 704 may be shaped to receive certain modules and not others. For example, a given pocket 704 may be shaped to allow insertion of one particular module and discourage the insertion of other types of modules. Thereby, the user of the wearable medical device may be encouraged to attach the modules at the correct location. The pockets 704 may further be shaped, for example, tapered to facilitate or ensure that intended modules are inserted into the pockets 704 in a correct orientation. It is appreciated that the pockets 704 may also be similarly shaped and the location of each module may be interchangeable. For example, the energy operations module may be inserted into any of the pockets 704 and operate correctly. Thereby, the user of the wearable medical device can insert any module into any pocket 704.

Figure 8A:
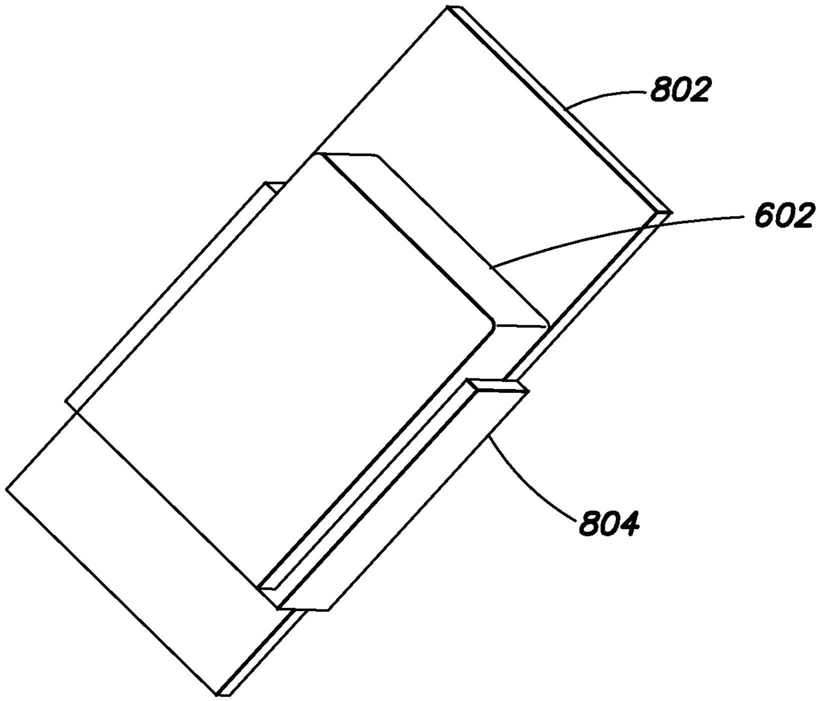
FIGS. 8A and 8B show various techniques for adjusting a location of a module on a garment for a wearable medical device.
Figure 8B:
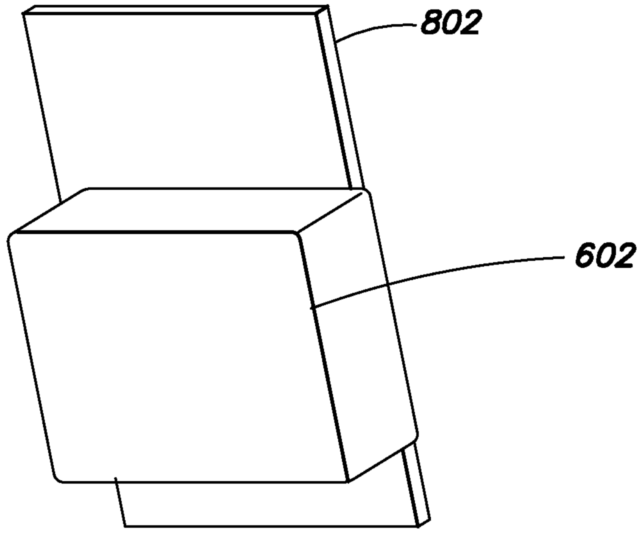

In at least one example, the modules may be movable by the patient about the garment. Thereby, the patient can readjust the location of one or more modules to fit their particular preference. FIGS. 8A and 8B illustrate an example strap 802 of a garment along which the module 602 can slide. In FIG. 8A, the module is removably secured to a guide 804 that slides along the strap 802. In FIG. 8B, the module 602 directly connects to the strap 802 and slides along the strap 802.

In some examples, the strap 802 includes conductive thread or wiring that may be engaged by the guide 804 in FIG. 8A and/or the module 602 in FIG. 8B. The module 602 may communicate with other modules removably secured in the garment by the conductive thread or wiring sewn into the garment (e.g., the strap 802).

Figure 9A:
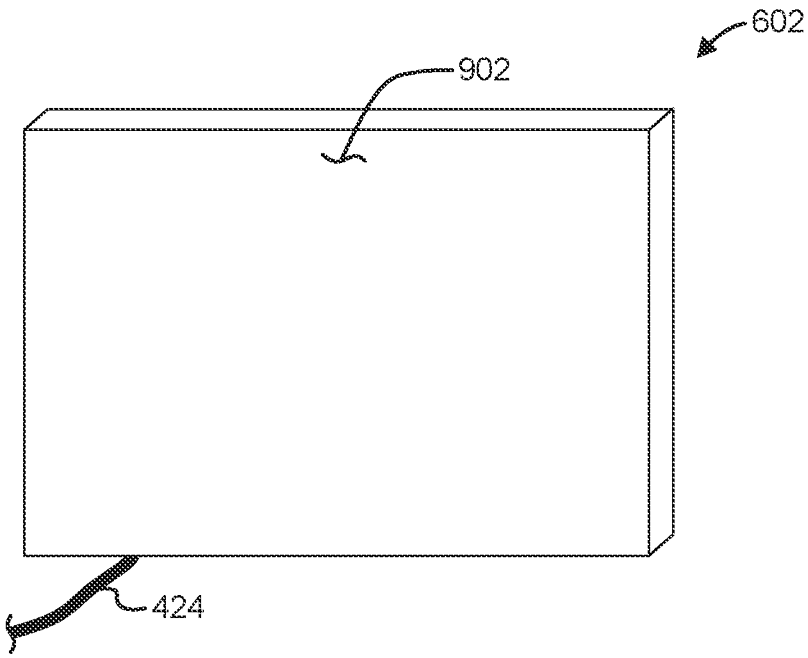
FIGS. 9A and 9B show example modules for a wearable medical device.
Figure 9B:
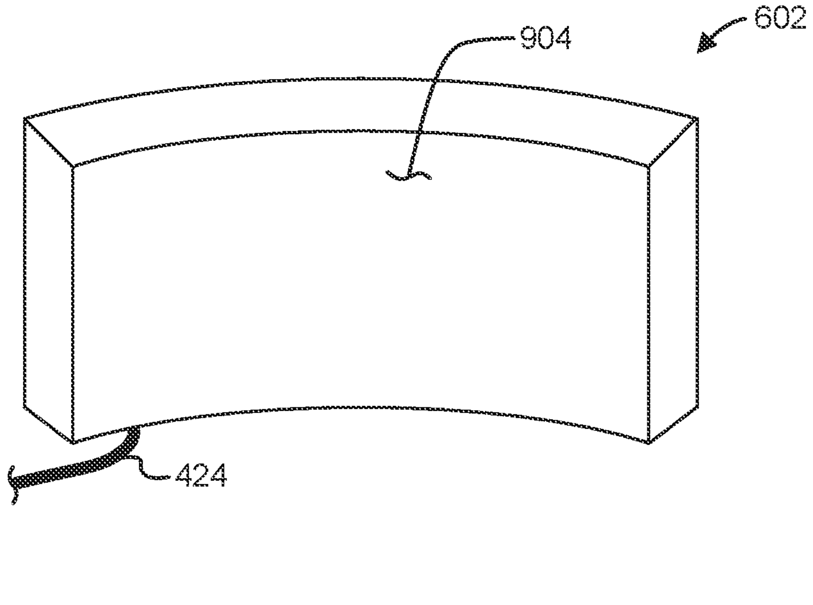

It is appreciated that the module 602 may be constructed in a variety of configurations and is not limited to any single configuration. FIGS. 9A and 9B illustrate two example configurations of an example module 602. The module 602 connected to the link 424 in FIG. 9A has an enclosure with a flat surface 902 that encapsulates one or more electronic devices similar to the modules previously illustrated. The enclosure may be constructed from a rigid plastic including, for example, acrylonitrile butadiene styrene (ABS) plastic. FIG. 9B illustrates another configuration of a module 602 with a contoured surface 904 that may better conform to the body of a patient. The particular shape of the contoured surface 904 may be pre-configured or uniquely designed for the patient. For example, various body size measurements may be obtained from the patient and a uniquely tailored enclosure may be 3D printed from, for example, any suitable thermoplastic (e.g., ABS plastic).

Example Integrated Garments with One or More Permanently Attached Modules

As discussed above, the functional components of a wearable monitoring and/or treatment device may be divided into various modules and distributed about the garment. In at least one example, one or more of the modules in the set of modules are integrated into the garment 500 and coupled by links 424 that are integrated into the garment (e.g., by conductive thread). The modules may be integrated into the garment by, for example, permanently affixing the modules to the garment as described in more detail below. For example, the rigid enclosure of one or more of the modules may be permanently affixed to the garment by rivets and/or studs. Integrating one or more modules into the garment 500 in this manner may reduce the bulkiness of the modules and make the wearable medical device easier for the patient to conceal. For example, the integrated garment may appear as a normal garment (e.g., a shirt) to the general populace and/or be easily concealable under a normal garment (e.g., a button-down shirt).

Figure 10A:
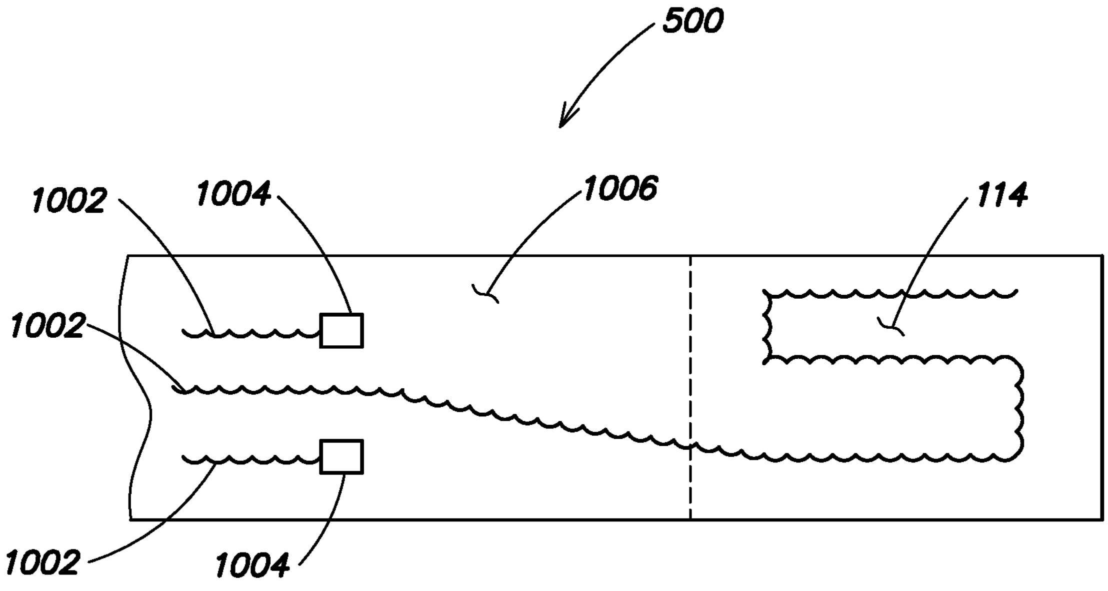
FIGS. 10A and 10B show an example integrated therapy electrode with a receptacle to receive a replaceable gel pack.
Figure 10B:
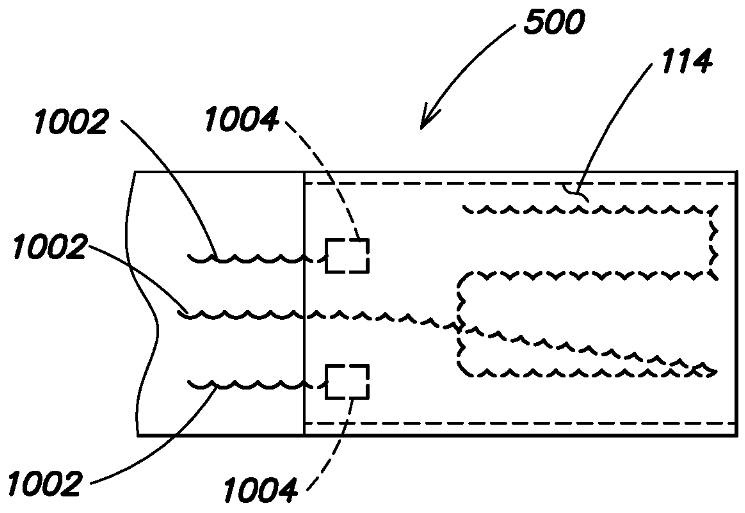

In some examples, at least one therapy electrode is permanently integrated into the garment. In some examples, at least one therapy electrode is supported by the garment. In some examples, one or more therapy electrodes may be integrated into the garment 500 and constructed to receive a gel deployment pack as described in the '801 Patent. For example, the gel deployment pack may be operatively coupled or connected to gel deployment circuitry as described above, and may receive operational signals from such circuitry. FIGS. 10A and 10B illustrate such an integrated therapy electrode. FIG. 10A illustrates an open receptacle 1006 on a garment 500 for a gel deployment pack. The gel deployment pack is installed in the receptacle 1006 by attachment to the connection points 1004. The connection points 1004 both hold the gel deployment pack in place and operably couple the gel deployment pack to conductive thread 1002 or wiring that is integrated into the garment. The connection points 1004 may employ similar techniques as those described above with reference to FIGS. 6A-6E. After the gel deployment pack is installed, a flap housing the integrated therapy electrode 114 may be folded over the gel deployment pack as illustrated in FIG. 10B. In some implementations, the gel pack can include a control unit configured to release conductive gel through the flap including the therapy electrode and onto a surface of the patient's skin. The control unit may be operatively connected to gel deployment circuitry to determine the appropriate timing to initiate the delivery of the gel. For example, the gel deployment circuitry may initiate gel delivery prior to or in connection with delivering an electric shock, thus lowering impedance between the subject's skin and the therapy electrode 114. After the conductive fluid is deployed, the external defibrillator administers an electric shock to the subject via the therapy electrode 114 and conductive fluid. Spent gel packs can be removed from the wearable therapeutic device and replaced with another gel pack that contains at least one dose of conductive fluid. In some implementations, the garment and/or integrated therapy electrode may comprise perforations and/or holes for passing the conductive gel from the gel pack through the garment and/or integrated therapy electrode on to the patient's skin.

In some examples, one or more therapy electrodes may deliver one or more therapeutic shocks to a patient without conductive gel. In some examples, instead of deploying conductive gel, the therapy electrode 114 can be adhesively coupled to the patient's skin and include hydrogel layers to promote conductivity. For example, a long term (e.g., 7 days or more) hydrogel based electrode may be disposed on the patient's skin on a patient facing side, and coupled to the garment by a Velcro® brand hook-and-loop fastener on a non-patient facing side. An example long term adhesive electrode for such use is described in U.S. Patent Publication No. 2013/0325096 entitled "LONG TERM WEAR MULTIFUNCTION BIOMEDICAL ELECTRODE," published on Jan. 1, 2015 (hereinafter the "'096 publication") which is hereby incorporated herein by reference in its entirety.

Figure 11:
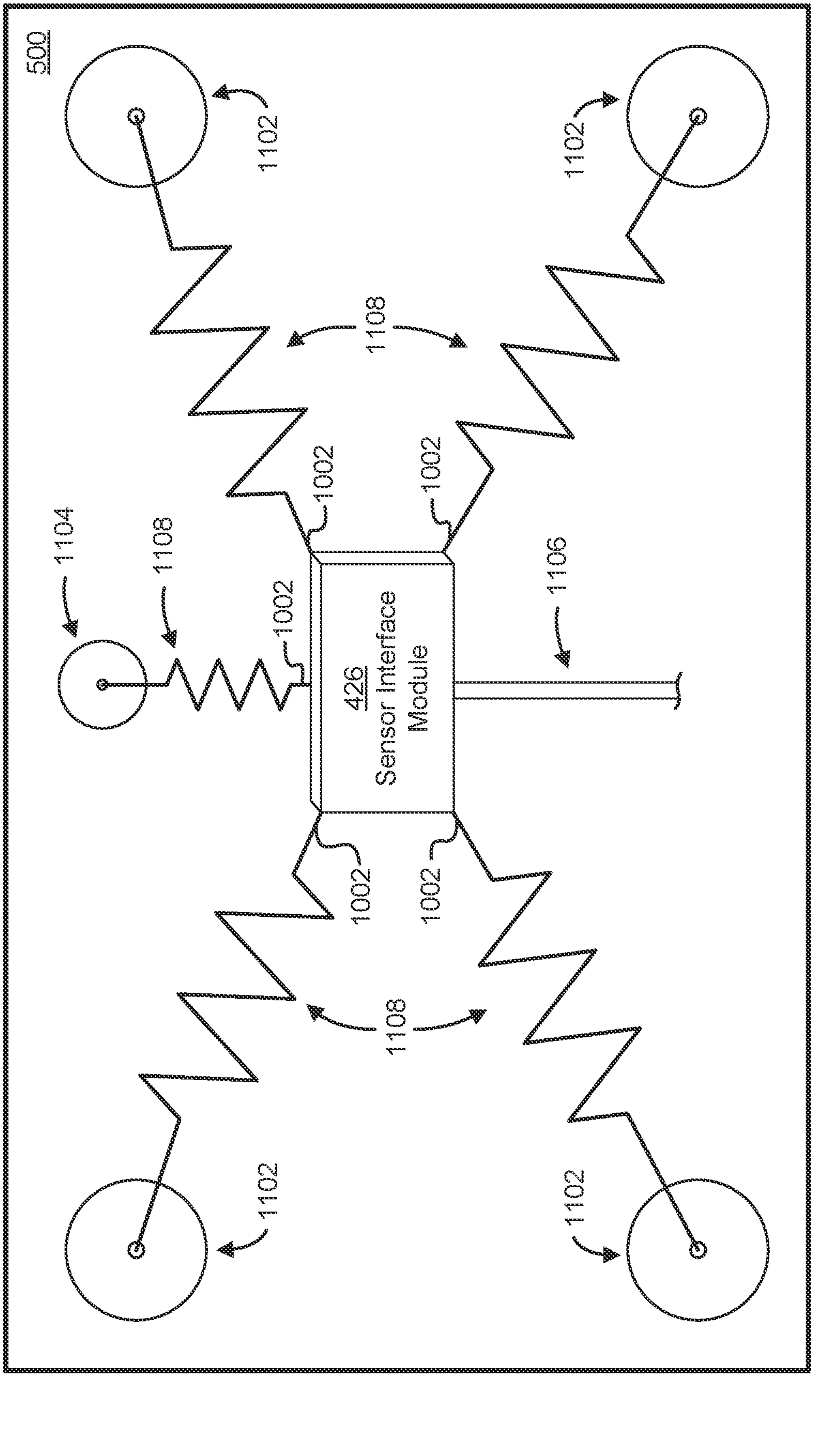
FIG. 11 shows an example sensor interface module integrated into a garment for a wearable medical device.

FIG. 11 illustrates an example sensor interface module 426 integrated into the garment 500. The sensor interface module 426 may include cardiac monitoring circuitry that is disposed in the garment and is configured to monitor cardiac activity of the patient. In some implementations, the cardiac monitoring circuitry is disposed in the garment and configured to monitor a cardiac activity of the patient and detect a cardiac condition of the patient based on the monitored cardiac activity of the patient and provide at least one therapeutic pulse to the patient based on the detected cardiac condition. The cardiac monitoring circuitry may comprise a plurality of separate and distinct modules or modular components distributed about the garment. As illustrated, the sensor interface module 426 receives signals from ECG electrodes 1102 and ground electrode 1104 via the conductive thread 1002 or wiring woven into the garment 500. The conductive thread 1002 or wiring may be woven into the garment 500 with one or more expansion sections 1108 between the sensor interface module 426 and the ECG electrodes 1102 and/or ground electrode 1104. The expansion sections 1108 may enable the garment 500 to expand and contract. For example, the conductive thread 1002 or wiring may include inelastic conductive thread or wire while the garment 500 may comprise an elastic thread. In this example, the expansion sections 1108 allow the garment 500 to stretch without breaking the inelastic conductive thread or wiring or the connections between various devices (e.g., the ECG electrode 1102) and the conductive thread or wiring. It is appreciated that the expansion sections 1108 in the conductive thread 1002 or wiring do not need to be constructed in a zigzag design as illustrated in FIG. 11. For example, the expansion sections 1108 may be woven into the garment 500 as smoothed peaks-and-valleys.

In some implementations, the conductive thread 1002 or wiring may be routed through a non-critical dimension, e.g., instead of the conductive thread 1002 or wiring stretching around the torso of the patient, the conductive thread 1002 or wiring may be configured to route over the shoulder of the patient. In this regard, the conductive thread 1002 or wiring that is disposed along the non-critical dimension may not be subject to expansion and contraction changes of the garment.

The sensor interface module 426 may, for example, pre-treat and/or digitize the received signals from the ECG electrodes 1102 and the ground electrode 1104 before providing the information to other components (e.g., operations module 406). For example, the operations module 426 may reduce and/or remove common mode noise in the signals received from the ECG electrodes 1102 with the signal from the ground electrode to improve the quality of the ECG signals. The ECG signal may be digitized, for example by a digital-to-analog converter, and communicated via the bus 1106 to other components. For example, the bus 1106 may be a controller area network (CAN) bus. In this example, the sensor interface module 426 may communicate the digitized ECG signal to other components via the CAN bus. For example, a controller of the wearable cardiac monitoring device may be configured to detect a cardiac condition of the patient based on the monitored cardiac activity of the patient. The CAN bus may be integrated into the garment 500 with two or more strands of conductive thread or wiring. It is appreciated that the bus 1106 may also support power transfer and, for example, provide power to the operations modules 426.

In some implementations, patient monitoring circuitry of the sensor interface module may comprise a plurality of separate and distinct modules or modular components that are integrated into and supported by the garment. For example, the patient monitoring circuitry of the sensor interface module may include one or more filters, amplifiers, signal analysis units, signal multiplexers or de-multiplexers, etc. that may be included in separate and distinct modules or modular components.

Figure 12A:
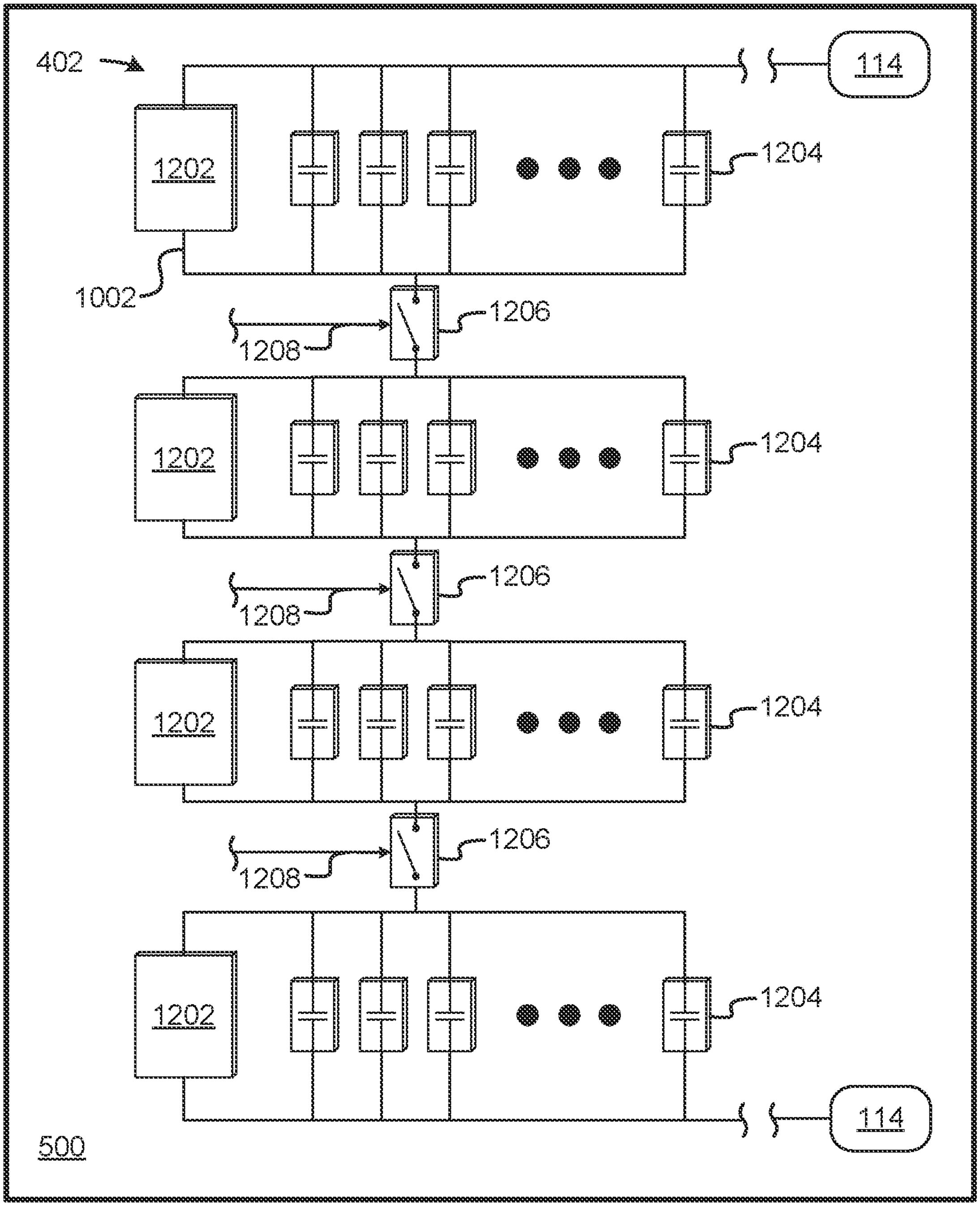
FIGS. 12A and 12B show example energy storage modules integrated into a garment for a wearable medical device.
Figure 12B:
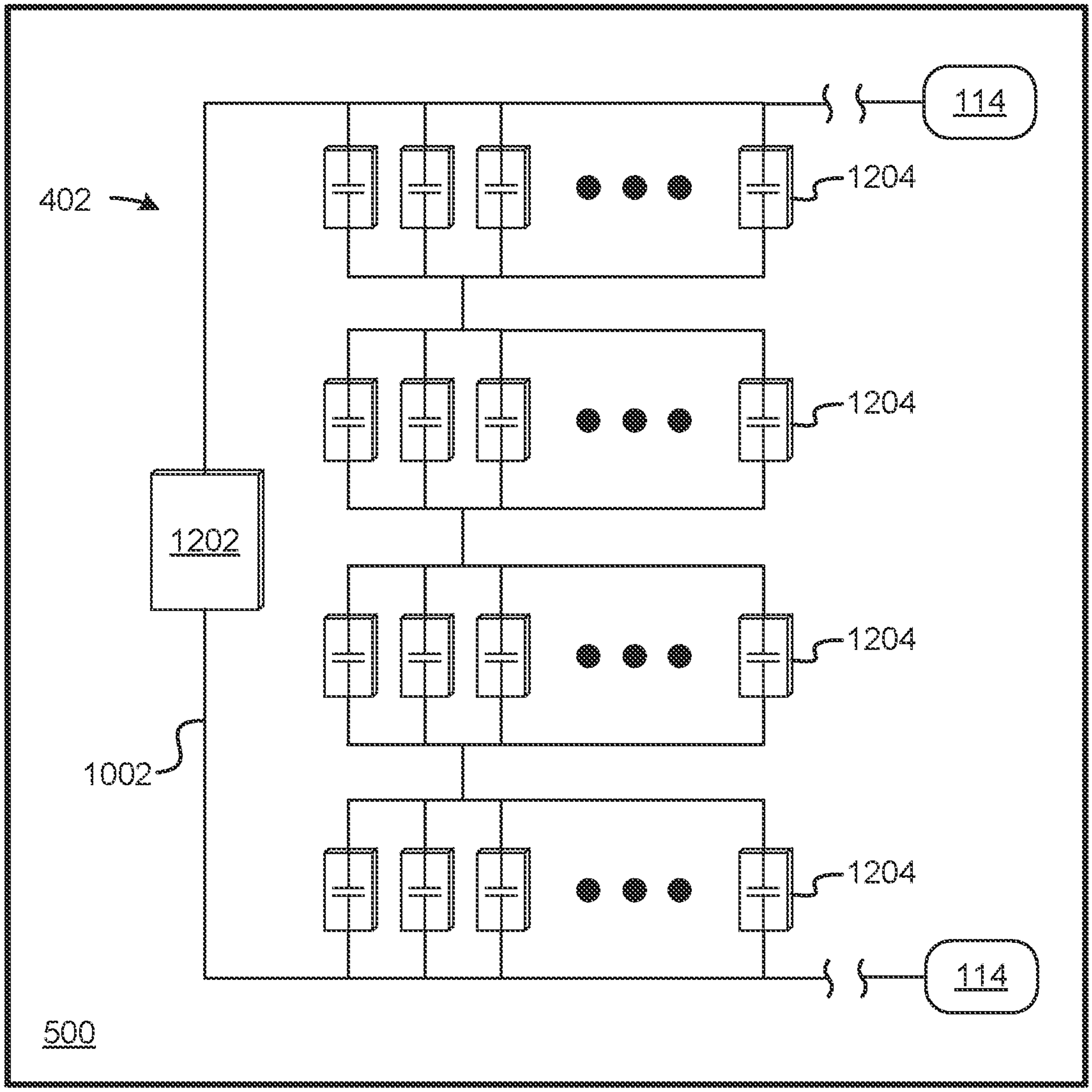

In some examples, the energy storage module 402 may be integrated into the garment 500 as illustrated in FIGS. 12A and 12B. For example, the charge capacity of the energy storage module 402 may be divided over a network of small capacitors 1204 that are each integrated into the garment 500 at various locations and coupled by conductive threading 1002 or wiring. The capacitors 1204 may be integrated into various locations so as to evenly distribute the weight of the energy storage module 402. Dividing the capacitance of the capacitor bank across a plurality of smaller capacitors 1204 advantageously allows the size of each capacitor 1204 to be shrunk. For example, the capacitors 1204 may be small ceramic capacitors each with a volume less than one centimeter cubed, a capacitance under 100 μF, and a breakdown voltage rating between 200 volts and 500 volts. Thereby, the capacitors 1204 may be easily integrated into the garment 500 without interfering with the mobility of the patient. It is appreciated that one or more battery sources may be similarly divided into a plurality of cells and integrated into the garment.

Referring to FIG. 12A, the capacitors 1204 may be organized into a plurality of capacitor banks (e.g., 4 capacitor banks) each coupled to a charger 1202. The capacitor banks may be coupled to each other by one or more switches 1206 that control the connection between the capacitor banks based on a control signal 1208 from, for example, the therapy control module 404. Thereby, each of the capacitor banks may be charged in parallel by a charger 1202 (e.g., by opening the switch(es) 1206) and discharged in series with one another (e.g., by closing the switch(es) 1206). It is appreciated that the number of capacitor banks employed and/or the particular number of capacitors 1204 in each bank may be altered based on the particular implementations. Further, a single charger 1202 may be employed to charge multiple capacitor banks. For example, the four chargers 1202 illustrated in FIG. 12A may be replaced by a single charger connected to all four of the capacitor banks.

In some implementations, each capacitor bank may have a total capacitance rating (e.g., 650 μF) that is divided up among the plurality of capacitors 1204 connected in parallel. The total capacitance of the capacitor bank is equal to the sum of the capacitance of each capacitor in the bank. Thereby, a target total capacitance rating may be achieved by matching the sum total of the capacitances of the capacitors 1204 in the bank to the target. For example, the capacitor bank may be designed to have a capacitance of 650 μF and the capacitor bank may be constructed from 100 capacitors each with a capacitance of 6.5 μF (6.5 μF*100=650 μF). It is appreciated that other capacitor configurations may be employed including, for example, 130 capacitors each with a capacitance of 5 μF (5 μF*130=650 μF). Although FIGS. 12A and 12B illustrate four capacitor banks each including a plurality of capacitors where each capacitor bank may have a total capacitance of about 650 μF, it is to be appreciated that other examples may include capacitor banks having different capacitances or capacitor backs having only a single capacitor each. For example, in one implementation a wearable monitoring and/or treatment device may include four capacitors each with a capacitance of about 650 μF.

Referring to FIG. 12B, the capacitors may be organized in a plurality of banks that are coupled in series without the switch 1206. In these implementations, the capacitor banks may be charged in series by a charger 1202. Both charging and discharging the capacitor banks in a series configuration may omit one or more components (e.g., the switch(es) 1206), but may require a higher charging voltage to store the same amount of energy relative to the parallel charging configuration illustrated in FIG. 12A.

It is appreciated that the capacitors 1204 may be constructed in a variety of form factors. For example, each capacitor 1204 may be constructed as a capacitor module comprising a capacitor (e.g., a ceramic capacitor) encapsulated in a rigid enclosure that is integrated into the garment. The capacitor modules may also be custom capacitors created by packing a dielectric between two conductive plates and attaching conductive thread or wiring to the conducting plates. In some implementations, the capacitors 1204 may be small capacitors that are directly integrated into the garment and coupled by conductive thread or wiring.

In some examples, the capacitors 1204 may be integrated into other components of the wearable medical device. For example, the wearable medical device may include one or more flat or contoured surfaces including, for example, a back-side of a gel deployment pack and/or a back-side of a therapy electrode. In these examples, a capacitor may be integrated into these flat or contoured surfaces by placing a dielectric between two conductors.

The electrical circuitry in the therapy control module 404, the operations module 406, the communications module 408, and/or at least one user interface 410 may also be integrated into the garment. For example, the various circuitry components of the modules may be mounted to a flexible substrate that can bend to the contours of the body of a patient. The flexible substrates with various circuit components may be permanently affixed to the garment and sandwiched between two pieces of fabric. It is appreciated that the electrical components mounted to the flexible substrate may be made waterproof and/or water-resistant by, for example, covering the components in a waterproof coating (e.g., an epoxy coating). The electrical components may also be encapsulated in a waterproof and/or water resistant housing that is permanently disposed within the garment. Thereby, the garment may be washed without damaging the electrical components that are permanently disposed into the garment.

Additional Example Garments

Having described various techniques for distributing various components about a garment and/or integrating various components into the garment, it is appreciated that these techniques may be applied to a variety of garments. FIGS. 13A, 13B, 14 and 15 illustrate various examples of such garments.

Figure 13A:
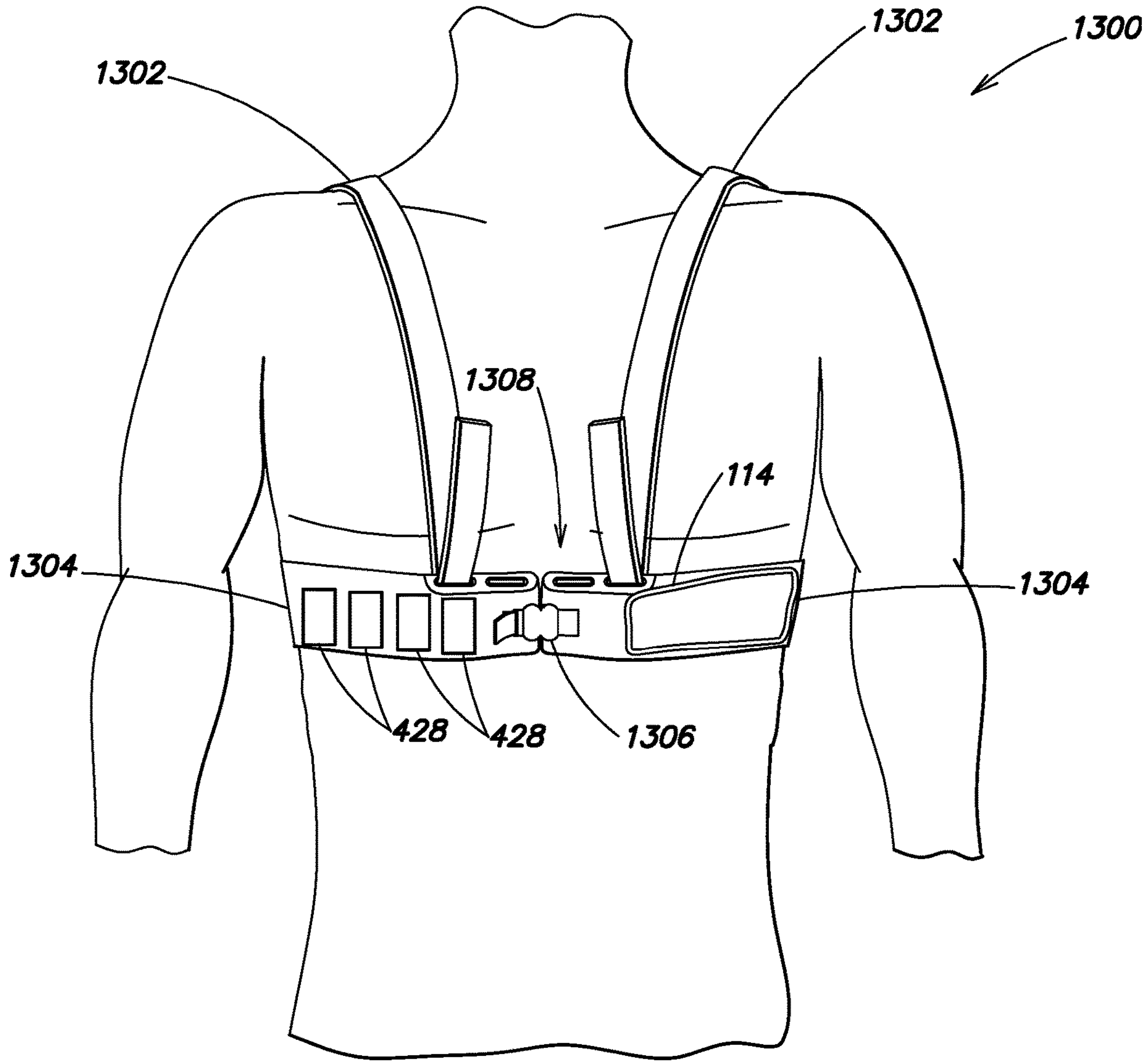
FIGS. 13A and 13B show an example garment for a wearable medical device.
Figure 13B:
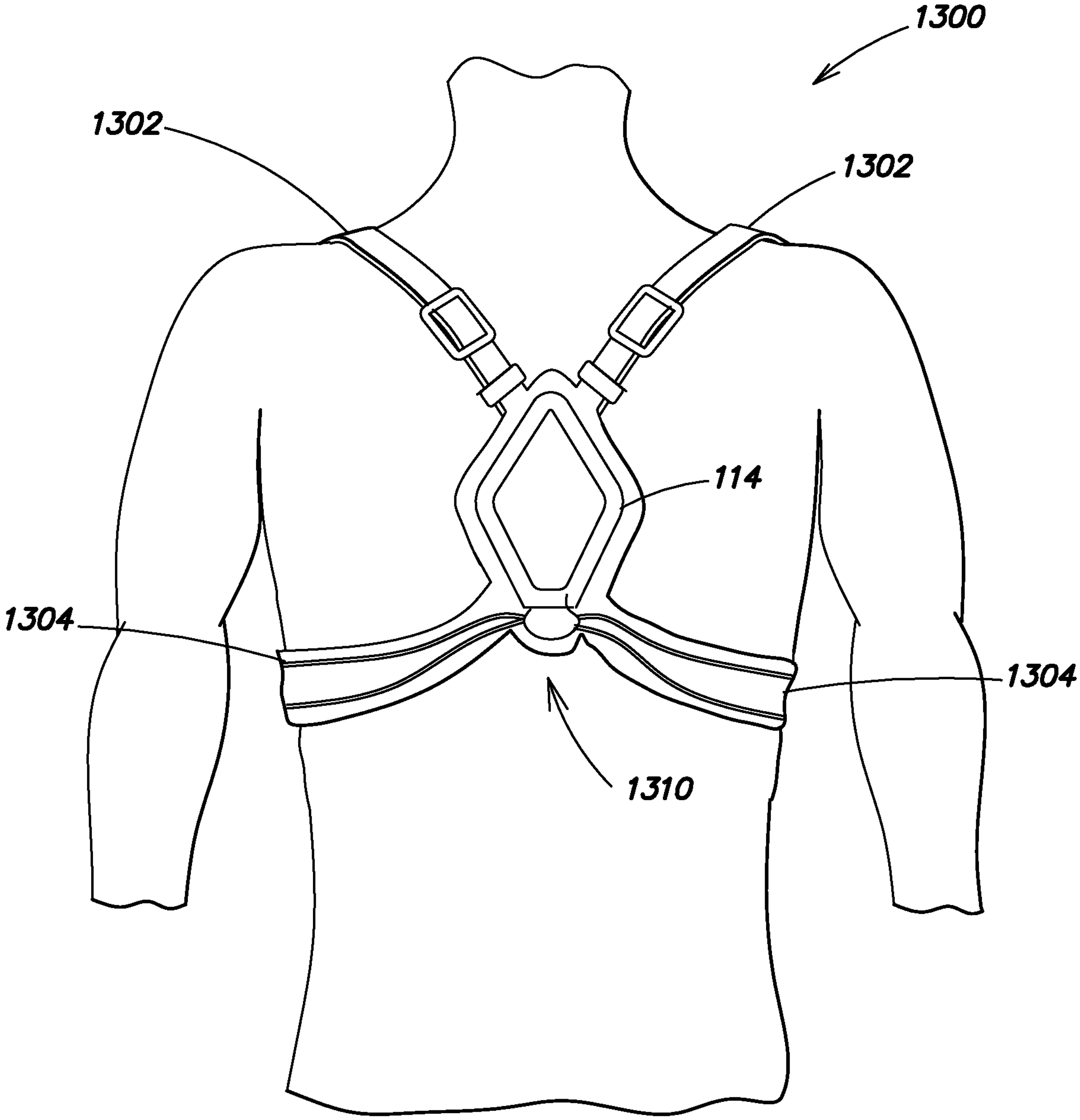

FIGS. 13A and 13B show a garment 1300 for a wearable medical device. The garment 1300 includes a front portion 1308 and a rear portion 1310 connected by side portions 1304 and adjustable straps 1302. The garment 1300 further includes a buckle 1306 to removably secure the side portions 1304 of the garment. The garment wraps around an upper torso of the patient and includes a therapy electrode 114 and sensors 428 on the front portion 1308 in addition to another therapy electrode 114 on the rear portion 1310.

Figure 14:
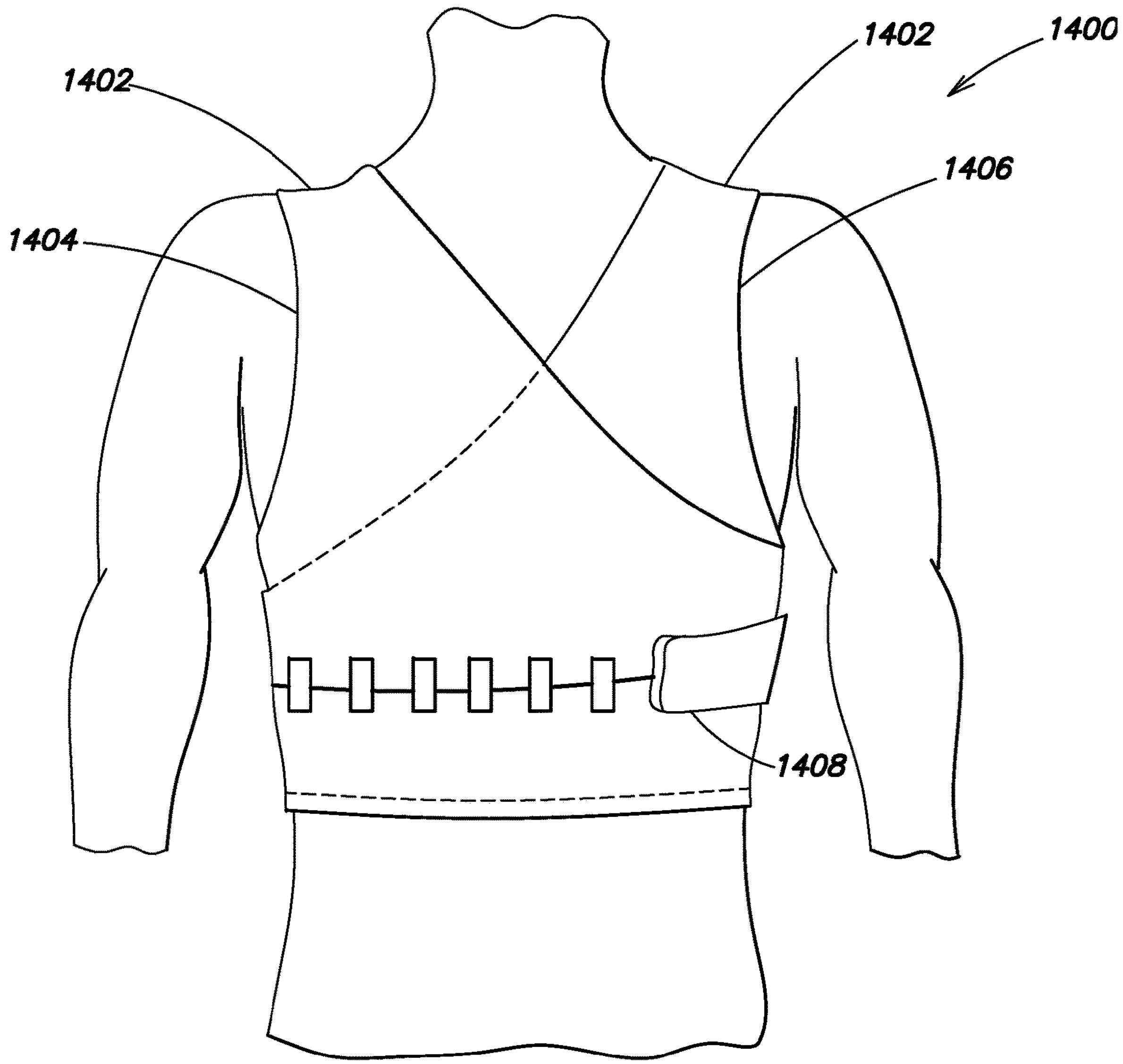
FIG. 14 shows another example garment for a wearable medical device.

FIG. 14 shows another example garment 1400 for a wearable medical device. The garment 1400 may be constructed to wrap around an upper torso of the patient. For example, the first portion 1404 may wrap around both the patient and the second portion 1406 (similar to a bath robe) to be secured in place by hook-and-loop fasteners on flap 1408. The garment 1400 extends over the shoulders with two shoulder straps 1402.

Figure 15:
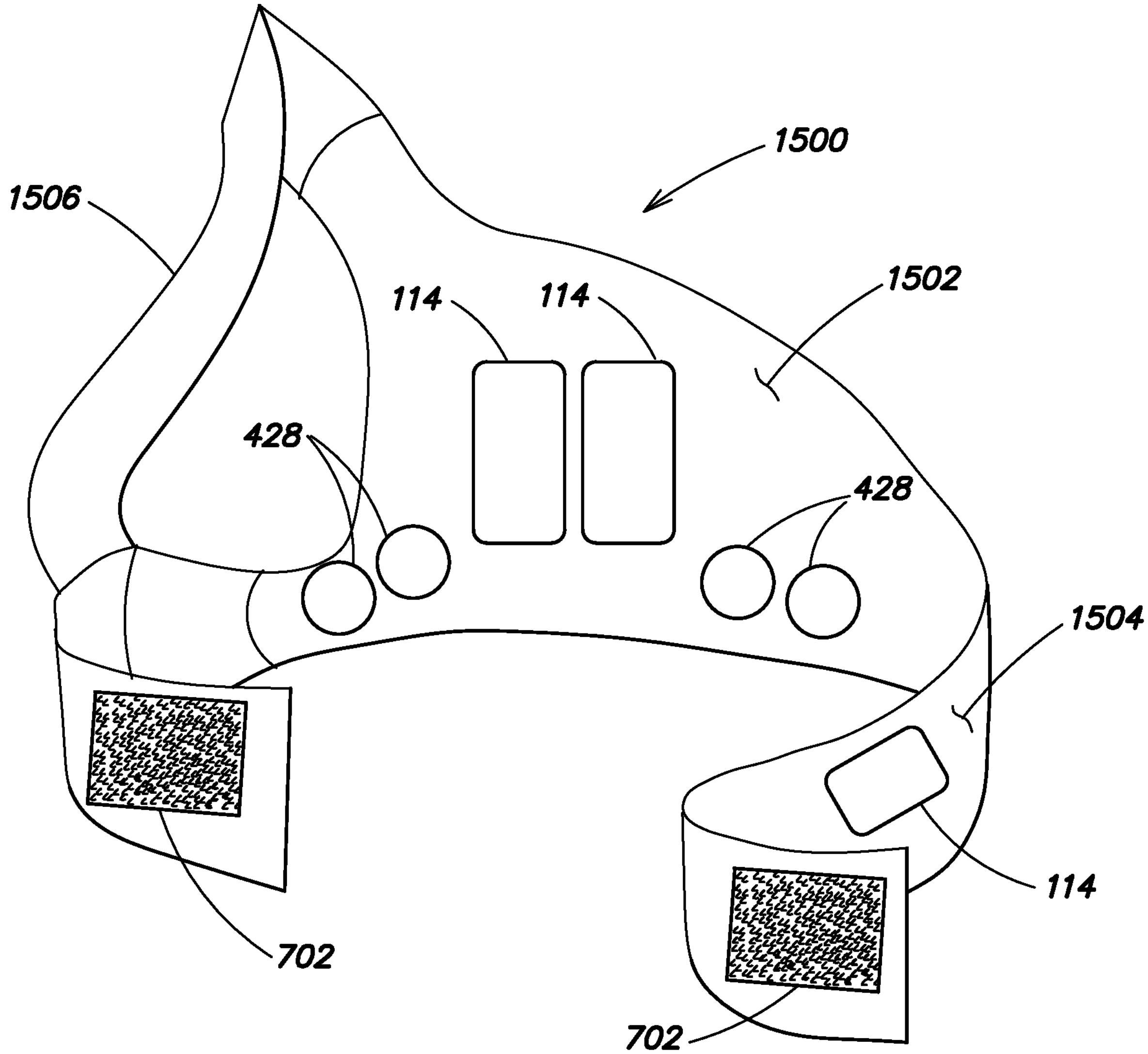
FIG. 15 shows another example garment for a wearable medical device.

FIG. 15 shows another example garment 1500 for a wearable medical device. The garment 1500 includes a front portion 1504 to wrap around an upper torso of the subject that is secured in place by hook-and-loop fasteners 702. The garment 1500 further includes a rear portion 1502 that connects to the front portion by a single shoulder strap 1506. The front portion 1504 includes a therapy electrode and the rear portion 1502 includes additional therapy electrodes and multiple sensors 428.

It is appreciated that any of the garments descried herein may include multiple parts. For example, the garment may include a vest worn about an upper torso of the patient and a separate belt that is detachable from the vest. In this example, the sensors 428 and/or therapy pads 114 may be integrated into the vest and the various modules (e.g., modules 402, 404, 406, 408 described above) may be integrated into the belt. The belt may be detachable from the vest by, for example, a buckle, a hook-and-loop fastener, and/or a snap. In addition, one or more pieces of the garment may be designed to be inexpensive and/or disposable. For example, the vest portion of the garment may be disposable while the belt (including the various modules) may be laundered and redeployed to a new patient with a new garment.

Having thus described several aspects of at least one example of this disclosure, it is to be appreciated various alterations, modifications, and improvements will readily occur to those skilled in the art. Such alterations, modifications, and improvements are intended to be part of this disclosure, and are intended to be within the scope of the disclosure. Accordingly, the foregoing description and drawings are by way of example only.

What is claimed is:

1. An improved modular wearable medical device for monitoring a patient's electrocardiogram (ECG) signals and providing therapeutic shocks in the event of a cardiac arrhythmia, comprising:

a garment configured to be worn around a torso of a patient, a plurality of ECG sensing electrodes that are permanently coupled at first predetermined locations on the garment, the plurality of ECG sensing electrodes configured to sense the patient's ECG signals, a pocket or receptacle disposed on the garment and configured to removably secure a module comprising device electronics within a housing to the garment, wherein the pocket or receptacle is configured to allow for insertion of one particular type of module and discourage insertion of other types of modules, wherein the pocket or receptacle comprises a conductive connector configured to establish a connection between the module comprising device electronics within the housing and at least the plurality of permanently coupled ECG sensing electrodes on the garment, a sensor interface module configured as the module comprising the device electronics within the housing and further configured to snap into the conductive connector of the pocket or receptacle, wherein the sensor interface module is configured to receive the ECG signals from the patient via the conductive connector of the pocket or receptacle, pretreat and/or digitize the ECG signals for detecting the cardiac arrhythmia, and provide the pretreated and/or digitized ECG signals to at least one other component of the wearable medical device, a plurality of wires or cables permanently integrated into the garment, wherein the plurality of wires or cables permanently integrated into the garment is configured to operably couple at least the plurality of permanently coupled ECG sensing electrodes on the garment with the sensor interface module on the garment via the conductive connector of the pocket or receptacle such that the sensor interface module receives the ECG signals from the patient further via the plurality of wires or cables permanently integrated into the garment, a user interface configured to enable the wearable medical device to communicate with the patient, and therapy delivery systems comprising a plurality of therapy electrodes removably coupled to second predetermined locations on the garment, gel deployment circuitry configured to deliver conductive gel substantially proximate skin of the patient in contact with the plurality of therapy electrodes prior to the therapeutic shocks being provided to the patient, a plurality of a capacitor modules, each capacitor module comprising one or more capacitors configured to store energy for the therapeutic shocks to be provided to the patient, and an enclosure encapsulating the one or more capacitors, wherein the enclosure is integrated into the garment and adapted to conform to a predetermined portion of the patient's body, and a therapy control module configured to control the provision of the therapeutic shocks to the patient via the plurality of therapy electrodes from the stored energy in the event of the cardiac arrhythmia;

wherein the therapy delivery systems are configured to be separable from monitoring components comprising at least the plurality of ECG sensing electrodes and the sensor interface module such that the wearable medical device is re-configurable as a monitoring device configured to monitor a condition of the patient using the pretreated and/or digitized ECG signals or as a treatment device configured to monitor the condition of the patient using the pretreated and/or digitized ECG signals and initiate a treatment protocol comprising the provision of the therapeutic shocks to the patient;

wherein the wearable medical device is configured to perform a self-test to check that the therapy delivery systems have been properly attached and electrically or otherwise coupled to other portions of the wearable medical device; and wherein the user interface is further configured to detect a presence or a lack of the therapy delivery systems and prompt the patient to confirm whether the wearable medical device is configured as the monitoring device or as the treatment device based on the detected presence or lack of the therapy delivery systems.

2. The device of claim 1, wherein the garment comprises a flexible material configured to provide an ergonomic fit on the patient.

3. The device of claim 2, wherein the garment comprises a stretchable fabric and is configured to cover both an upper portion and lower portion of the torso of the patient.

4. The device of claim 1, wherein at least one of the plurality of wires or cables is at least one of flexible and/or stretchable.

5. The device of claim 4, wherein the at least one of the plurality of wires or cables is configured in a pattern comprising at least one of a coiled arrangement and a zig zag pattern so that the at least one of the plurality of wires or cables stretches with a portion of the garment.

6. The device of claim 4, wherein the at least one of the plurality of wires or cables is at least one of integrated with and/or attached to the garment.

7. The device of claim 1, wherein the garment comprises an interior fabric layer and an exterior fabric layer, the interior fabric layer and exterior fabric layer comprising different materials characteristics.

8. The device of claim 7, wherein interior fabric layer comprises a material permeable to moisture and/or water vapor so that the moisture and/or water vapor can pass from the interior fabric layer towards the exterior fabric layer.

9. The device of claim 8, wherein the interior fabric layer has an average moisture transmission rate of between about 100 $g/m^2/day$ to 50,000 $g/m^2/day$.

10. The device of claim 7, wherein the exterior fabric layer comprises at least one of a hydrophobic and/or super-hydrophobic material.

11. The device of claim 7, wherein the exterior fabric layer comprises at least one of nylon, polyester, and/or a lamination or coating of at least one of polytetrafluoroethylene, expanded polytetrafluoroethylene and/or polyurethane materials.

12. The device of claim 1, wherein the garment is configured to be machine washable.

13. The device of claim 1, wherein the garment comprises a belt portion and a back portion, the belt portion being configured to be detachable from the back portion by at least one of a buckle, a hook and loop fastener, and/or a strap.

14. The device of claim 13, wherein the belt portion comprises an adjustable fastener configured to secure a first end adjacent to a second end.

15. The device of claim 13, wherein the garment comprises one or more adjustable shoulder straps connected to the back portion and the belt portion.

16. The device of claim 1, wherein the conductive connector comprises a conductive snap.

17. The device of claim 1, wherein the conductive connector comprises a securing means configured to secure the module in place on the garment.

* * * * *